US006379945B1

(12) United States Patent
Jepson et al.

(10) Patent No.: US 6,379,945 B1
(45) Date of Patent: *Apr. 30, 2002

(54) GENE SWITCH

(75) Inventors: Ian Jepson, Maidenhead; Alberto Martinez, Binfield; Andrew James Greenland, Maidenhead, all of (GB)

(73) Assignee: Zeneca Limited, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/653,648

(22) Filed: May 24, 1996

(30) Foreign Application Priority Data

| May 26, 1995 | (GB) | ............................................. 9510759 |
| Jul. 7, 1995 | (GB) | ............................................. 9513882 |
| Aug. 24, 1995 | (GB) | ............................................. 9517316 |
| Mar. 18, 1996 | (GB) | ............................................. 9605656 |

(51) Int. Cl.⁷ ............................ C12N 5/10; C12N 1/15; C12N 5/04; C12N 15/12

(52) U.S. Cl. ............... 435/243; 435/254.1; 435/254.11; 435/325; 435/410; 435/419; 536/23.5

(58) Field of Search ....................... 536/23.5; 435/326, 435/69.1, 320.1, 325, 410, 419, 243, 254.1, 254.11

(56) References Cited

U.S. PATENT DOCUMENTS 5,424,333 A    6/1995   Wing .......................... 514/615

FOREIGN PATENT DOCUMENTS

| EP | 0 218 571 | 4/1987 |
| EP | 0 293 358 | 11/1988 |
| EP | 0 615 976 | 9/1994 |
| WO | 90/08826 | 8/1990 |
| WO | 90/14000 | 11/1990 |
| WO | 91/04323 | 4/1991 |
| WO | 91/13167 | 9/1991 |
| WO | 92/00377 | 1/1992 |
| WO | 92/04449 | 3/1992 |
| WO | 92/06201 | 4/1992 |
| WO | 93/03162 | 2/1993 |
| WO | 93/09237 | 5/1993 |
| WO | 93/23431 | 11/1993 |
| WO | 96/27673 | 9/1996 |

OTHER PUBLICATIONS

Bowie et al. (1990) Science 247: 1307–1310.*
George et al. (1988) Macromolecular Sequencing and Synthesis, (Ed. P.H. Schlesinger) Alan R. Liss Inc., New York, pp. 127–149.*

Allan, George F. et al., Ligand–dependent conformational changes in the pro–gesterone receptor are necessary for events that follow DNA binding, Proc. Natl. Acad. Sci., USA, Biochemistry, vol. 89, Dec. 1992, pp. 11750–11754.

Allan, George F. et al., "Hormone and Antihormone Induce Distinct Conforma–tional Changes Which Are Central to Steroid Receptor Activation", The Journal of Biological Chemistry, vol. 267, No. 27, Sep. 1992, pp. 19513–19520.

Ashburner, Michael, "Puffs, Genes, and Hormones Revisited", Cell, vol. 61, Apr. 6, 1990, pp. 1–3.

Beato, Miguel, "Gene Regulation by Steroid Hormones", Cell, vol. 56, Feb. 10, 1989, pp. 335–344.

Becker, Claudia et al., "PCR cloning and expression analysis of cDNAs encoding cysteine proteinases from germinating seeds of Vicia sativa L.", Plant Molecular Biology, vol. 26, 1994, pp. 1207–1212.

Cammue, Bruno P.A. et al., "Isolation and Characterization of a Novel Class of Plant Antimicrobial Peptides from Mirabilis jalapa L. Seeds", The Journal of Biological Chemistry, vol. 267, No. 4, Feb. 1992, pp. 2228–2233.

Calberg, Carsten et al., "Two nuclear signalling pathways for vitamin D", Nature, vol. 361, Feb. 18, 1993, pp. 657–660.

Cho, Wen–Long et al., "Mosquito Ecdysteroid Receptor: Analysis of the cDNA and Expression During Vitellogenesis", Insect Biochem. Molec. Biol., vol. 25, No. 1, 1995, pp. 19–27.

Christopherson, Karen S. et al., "Ecdysteroid–dependent regulation of genes in mammalian cells by a Drosophila ecdysone receptor and chimeric transactiva–tors", Proc. Natl. Acad. Sci., USA, Genetics, vol. 89, Jul. 1992, pp. 6314–6318.

Evans, Ronald M., "The Steroid and Thyroid Hormon Receptor Superfamily", Science, vol. 240, May 13, 1988, pp. 889–895.

Goetting–Minesky, M.P. et al., "Differential gene expression in an actinorhizal symbiosis: Evidence for a nodule–specific cysteine proteinase", Proc. Natl. Acad. Sci., USA, Plant Biology, vol. 91, Oct. 1994, pp. 9891–9895.

Green, Stephen et al., "Nuclear receptors enhance our understanding of trans–cription regulation", TIG, vol. 4, No. 11, Nov. 1988, pp. 309–314.

Heyman, Richard A. et al., "9–Cis Retinoic Acid Is a High Affinity Ligand for the Retinoid X Receptor", Cell, vol. 68, Jan. 24, 1992, pp. 397–406.

(List continued on next page.)

*Primary Examiner*—Michael Pak
(74) *Attorney, Agent, or Firm*—Jenkins & Wilson, P.A.

(57) ABSTRACT

The invention relates to an insect steroid receptor protein which is capable of acting as a gene switch which is responsive to a chemical inducer enabling external control of the gene.

14 Claims, 56 Drawing Sheets-

OTHER PUBLICATIONS

Hirst, M.C. et al., "Preparation of radiolabelled hybridization probes by STS labelling", Trends In Genetics, vol. 8, No. 1, Jan. 1992, pp. 6–7.

Hollenberg, Stanley M. et al., "Primary structure and expression of a functional human glucocorticoid receptor cDNA", Nature, vol. 318, No. 19, Dec. 16, 1985, pp. 635–641.

Imhof, Markus O. et al., Cloning of a *Chironomus tentans* Cdna Encoding a Protein (cEcRH) Homologous to the *Drosophila melanogaster* Ecdysteroid Receptor (dEcR), Insect Biochem. Molec. Biol., vol. 23, No. 1, Jan. 1993, pp. 115–124.

Jiang, Binghua et al., "Association of a 33–Kilodalton Cysteine Proteinase Found in Corn Callus with the Inhibition of Fall Arymworm Larval Growth", Plant Physiol., vol. 108, 1995, pp. 1631–1640.

Jindra, Marek et al.,"Isolation and Developmental Expression of the Ecdysteroid–induced GHR3 Gene of the Wax Moth *Galleria mellonella*", Insect Biochem. Molec. Biol., vol. 24, No. 8, 1994, pp. 763–773.

Kliewer, Steven A. et al., "Retinoid X receptor interacts with nuclear receptors in retinoic acid, thyroid hormone and vitamin $D_3$ signalling", Nature, vol. 355, Jan. 30, 1992, pp. 446–449.

Koelle, Michael R. et al., "The Drosophila EcR Gene Encodes an Ecdysone Receptor, a New Member of the Steroid Receptor Superfamily", Cell, vol. 67, Oct. 4, 1991, pp. 59–77.

Kothapalli, Ravi et al., "Cloning and Developmental Expression of the Ecdysone Receptor Gene From the Spruce Budworm, *Choristoneura fumiferana*", Developmental Genetics, vol. 17, 1995, pp. 319–330.

Krust, Andrée et al., "The chicken oestrogen receptor sequence: homology with v–erbA and the human oestrogen and glucocorticoid receptors", The EMBO Journal, vol. 5, No. 5, 1986, pp. 891–897.

Leid, Mark et al., "Multiplicity generates diversity in the retinoic acid signally path–ways", TIBS, vol. 17, Oct. 1992, pp. 427–433.

Leid, Mark et al., "Purification, Cloning, and RXR Identity of the HeLa Cell Factor with Which RAR or TR Heterodimerizes to Bind Target Sequences Efficiently", Cell, vol. 68, Jan. 24, 1992, pp. 377–395.

Linthorst, Huub J. et al., "Circadian expression and induction by wounding of tobacco genes for cysteine proteinase", Plant Molecular Biology, vol. 21, 1993, pp. 685–694.

Manglesdorf, David J. et al., "Characterization of three RXR genes that mediate the action of 9–cis retinoic acid", Genes & Development, vol. 6, 1992, pp. 329–344.

Oro, Anthony E. et al., "Relationship between the product of the *Drosophila ultraspiracle* locus and the vertebrate retinoid X receptor", Nature, vol. 347, Sep. 20, 1990, pp. 298–301.

Riddihough et al., "An ecdysone response element in the Drosophila hsp27 promoter", The EMBO Journal, vol. 6, No. 12, 1987, pp. 3729–3734.

Schena, Mark et al., "A steroid–inducible gene expression system for plant cells", Proc. Natl. Acad. Sci., USA, Genetics, vol. 88, Dec. 1991, pp. 10421–10425.

Segraves, William A., "Something Old, Some Things New: The Steroid Receptor Superfamily in Drosophila", Cell, vol. 67, Oct. 18, 1991, pp. 225–228.

Segraves, William A. et al., "The E75 ecdysone–inducible gene responsible for the 75B early puff in Drosophila encodes two new members of the steroid receptor superfamily", Genes & Development, vol. 4, 1990, pp. 204–219.

Smagghe, Guy et al., "Action of a Novel Nonsteroidal Ecdysteroid Mimic, Tebufenozide (RH–5992), on Insects of Different Orders", Pestic. Sci., vol. 42, 1994, pp. 85–92.

Smagghe, Guy et al., "Biological activity and receptor-binding of ecdysteroids and the ecdysteroid agonists RH–5849 and RH–5992 in imaginal wing discs of *Spodoptera exigua* (Lepidoptera:Noctuidae)", Eur. J. Entomol., vol. 92, 1995, pp. 333–340.

Smart, Catherine M. et al., "The timing of maize leaf senescene and characteri–sation of senescene–related cDNAs", Physiologia Plantarum, vol. 93, 1995, pp. 673–682.

Stemmer, Willem P.C., "Rapid evolution of a protein in vitro by DNA shuffling", Nature, vol. 370, Aug. 4, 1994, pp. 389–391.

Terras, Franky R.G. et al., "A new family of basic cysteine–rich plant antifungal proteins from Brassicaceae species", FEBS Letters, vol. 316, No. 3, pp. 233–240.

Thummel, Carl S. et al., "Spatial and Temporal Patterns of E74 Transcription during Drosophila Development", Cell, vol. 61, Apr. 6, 1990, pp. 101–111.

Vegeto, Elisabetta et al., "The Mechanism of RU486 Antagonism Is Dependent on the Conformation of the Carboxy–Terminal Tail of the Human Progesterone Receptor", Cell, vol. 69, May 15, 1992, pp. 703–713.

Yao, Tso–Pang et al., "Drosophila ultraspiracle Modulates Ecdysone Receptor Function via Heterodimer Formation", Cell, vol. 71, Oct. 2, 1992, pp. 63–72.

Yao, Tso–Pang et al., "Functional ecdysone receptor is the product of EcR and Ultraspiracle genes", Nature, vol. 366, Dec. 2, 1993, pp. 476–479.

Yu, Victor C. et al., "RXRβ: A Coregulator That Enhances Binding of Retinoic Acid, Thyroid Hormone, and Vitamin D receptors to Their Cognate Response Elements", Cell, vol. 67, Dec. 20, 1991, pp. 1251–1266.

Hogness, D.S., Talbot, W.S., Bender, M.T. and Koelle, M. [1992] X Ecdysone Workshop, Liverpool. Abstract).

* cited by examiner

Fig.1.

Sequence ID 1

1   TGCG AGG GGT GCA AGG AGT TCT TCA GGC GGA GTG TAA CCA AAA ATG
    ACGC TCC CCA CGT TCC TCA AGA AGT CCG CCT CAC ATT GGT TTT TAC

46  CAG TGT ACA TAT GCA AAT TCG GCC ATG CTT GCG AAA TGG ATA TGT
    GTC ACA TGT ATA CGT TTA AGC CGG TAC GAA CGC TTT ACC TAT ACA

91  ATA TGC GGA GAA AAT GCC AAG AGT A
    TAT ACG CCT CTT TTA CGG TTC TCA T

Fig.2.

Sequence ID 2

```
              3           9          15          21          27          33          39          45
              |           |           |           |           |           |           |           |
  1   TCC ACT GGT GTT TTC ACC ACA GAA AAG GCC TCT GCT CAT TTA
      AGG TGA CCA CAA AAG TGG TGT CTT TTC CGG AGA CGA GTA AAT
 46   GAG GGT GGT GCT AAG AAG GTC ATC ATC TCC TGC CCA GCG CTG
      CTC CCA CCA CGA TTC TTC CAG TAG TAG AGG ACG GGT CGC GAC
 91   ACC CAT GTT CGT CGT TGG TGT CAA CCT TGA AGC AGT ATG ACC CCT
      TGG GTA CAA GCA GCA ACC ACA GTT GGA ACT TCG TCA TAC TGG GGA
136   CTT ACA AGG TCA TCT CCA ACG CCT GCA CAA CCA ACT GCC TCG
      GAA TGT TCC AGT AGA GGT TGC GGA CGT GTT GGT TGA CGG AGC
181   CTC CTC TCG CTA AGG TCA TCC ATG ACA ACT TCG AGA TCA TTG AAG
      GAG GAG AGC GAT TCC AGT AGG TAC TGT TGA AGC TCT AGT AAC TTC
226   GTC TGA TGA CCA CTG TAC ACG CCA CTG CCA AGA AGA CAG
      CAG ACT ACT GGT GAC ATG TGC GGT GAC TCT TCT GTC
271   TGG ATG GAC CCT CTG GTA AAC TGT ACA CCG ATG GCC GTG GTG CTC
      ACC TAC CTG GGA GAC CAT TTG ACA TGT GGC TAC CGG CAC CAC GAG
316   AGC AGA ATA TCA TTC CCG CGG AAT TCC CCA GCC GCA GCT TAA
      TCG TCT TAT AGT AAG GGC GCC TTA AGG GGT CGG CGT CGA ATT
```

Fig. 2 i.

```
361  CCT GCA GAC ACA ACC CCT ACC TTC CAT GCC GTT ACC AAT GCC
     GGA CGT CTG TGT GGA TGG AAG GTA CGG CAA TGG TTA CGG

406  ACC GAC AAC ACC CAA ATC AGA AAA CGA GTC AAT GTC ATC AGG TCG
     TGG CTG TTG TGG GTT TAG TCT TTT GCT CAG TTA CAG TAG TCC AGC

451  TGA GGA ACT GTC TCC AGC TTC GAG TGT AAA CGG CTG CAG CAC AGA
     ACT CCT TGA CAG AGG TCG AAG CTC ACA TTT GCC GAC GTC GTG TCT

496  TGG CGA GGC GAG GCG GCA GAA AGG CCC AGC GCC GAG GCA GCA
     ACC GCT CCG CTC CGC CGT CTT TCC GGG TCG CGG CTC CGT CGT

541  AGA AGA GCT ATG TCT TGT CTG CGG CGA CAG AGC CTC CGG ATA TCA
     TCT TCT CGA TAC AGA ACA GAC GCC GCT GTC TCG GAG GCC TAT AGT

586  CTA CAA CGC GCT CAC ATG TGA AGG GTG TAA AGG TTT CTT CAG GCG
     GAT GTT GCG CGA GTG TAC ACT TCC CAC ATT TCC AAA GAA GTC CGC

631  GAG TGT AAC CAA AAA TGC AGT CAT GTA CAA ATT CGG CCA TGC
     CTC ACA TTG GTT TTT ACG TCA CAT CAT GTT TAA GCC GGT ACG

676  TTG CGA AAT GGA TAT CTA TAT GCG AAA ATG CAA ATG TCA GAA GTG TCG
     AAC GCT TTA CCT GAT ATA CGC TTT TAC GTT TAC AGT CTT CAC AGC

721  GTT GAA GAA ATG TCT TGC GGG CAT GAG GCC CGA GTG CGT GGT
     CAA CTT CTT TAC AGA ACG CCC GTA CTC CGG GCT CAC GCA CCA

766  GCC GGA GAA CCA GTG TGC AAT GAA ACG GAA AGA AAA GGC GCA
     CGG CCT CTT GGT CAC ACG TTA CTT TGC CTT TCT TTT CCG CGT
```

Fig. 2 ii.

```
 811  GAG GGA AAA AGA CAA ATT GCC CGT CAG TAC GAC GAC AGT AGA CGA
      CTC CCT TTT TCT GTT TAA CGG GCA GTC ATG CTG CTG TCA TCT GCT

856  TCA CAT GCC TCC CAT GCA ATG TGA ATG CCC TCC GCC AGA GGC
      AGT GTA CGG AGG GTA CGT TAC ACT TAC GGG AGG CGG TCT CCG

901  CGC TAG AAT TCT GGA ATG TGT GCA GCA CGA GGT GGT GCC ACG ATT
      GCG ATC TTA AGA CCT TAC ACA CGT CGT GCT CCA CCA CGG TGC TAA

946  CCT GAA TGA GAA GCT AAT GGA ACA GAA CAG GAA GAA CGT GCC
      GGA CTT ACT CTT CGA TTA CCT TGT CTT GTC CTT CTT GCA CGG

991  CCC CCT CAC TGC CAA GAA GTC GAT CGC AAG GCT CGT GTG
      GGG GGA GTG ACG GTT CTT CAG CTA GCG TTC CGA GCA CAC

1036  GTA CCA GGA AGG CTA TGA ACA ACC TTC CGA GGA AGA CCT GAA GAG
      CAT GGT CCT TCC GAT ACT TGT TGG AAG GCT TCT GGA CTT CTC

1081  GGT TAC ACA GTC GGA CGA CGA GAT GAT TCT AGA AGT GCA GCT GCC GTT
      CCA ATG TGT CAG CCT GCT GCT CTA CTG AGA TCA CGT CGA CGG CAA

1126  CCG TCA GAT TAC CGA CTC AGA CTC GAA AGT GCA GCT CAT CGT
      GGC AGT CTA ATG GCT GAG TCT ATA GTC ACT CGA GTA GCA

1171  AGA ATT CGC TAA GGG CCT CAA GAT CGG GTT CTC GCA GTC
      TCT TAA GCG ATT CCC GGA GTT CTA GGG CCC GAA CGT CAG

1216  GGA CCA GAT CAC GTT ATT AAA GGC GTG TGA TGA GAG GAT GAT
      CCT GGT CTA GTG CAA TAA TTT CCG CAC ACT TTC ACT CCA CTA CTA

1261  GCT CCG AGT GGC TCG GCG TGA GTA CGC GGC CAC CGA CAG CGT ACT
      CGA GGC TCA CCG AGC CGC ACT CAT GCG CCG GTG GCT GTC GCA TGA
```

Fig.2 iii.

```
1306  GTT CGC GAA CAA CCA GGC GTA CAC TCG CGA CAA CTA CCG CAA GGC
      CAA GCG CTT GTT GGT CCG CAT GTG AGC GCT GTT GAT GGC GTT CCG

1351  AGG CAT GGC GTA CGT CAT GGA CGA GGA CCT GCT GCA CTT CTG GTG
      TCC GTA CCG CAT GCA GTA CCT GCT CCT GGA CGA CGT GAA GAC CAC

1396  CAT GTA CTC CAT GAT GAT GGA TAA CGT GCA TTA TGC GCT GCT TAC
      GTA CAT GAG GTA CTA CTA CCT ATT GCA CGT AAT ACG CGA CGA ATG

1441  AGC CAT TGT CAT CTT CTC AGA CCG GCT GAG ATA CGG GCT ACC CCT
      TCG GTA ACA GTA GAA GAG TCT GGC CGA CTC TAT GCC CGA TGG GGA

1486  GTT GGT GGA GGA CAT CCA CAG GAA CAC CAC ACG GGT
      CAA CCA CCT CCT GTA GGT GTC CTT GTG GTG TGC CCA

1531  GTA CAT CCT GAA CCA CAG CGC GCC CGG CGC CGT CAT
      CAT GTA GGA CTT GGT GTC GCG CGG GCC GCG GCA GTA

1576  CTT CGG CGA GAT CCT GGG CAT ACT GAC GGA CCG GCT GGG
      GAA GCC GCT CTA GGA CCC GTA TGA CTG CCT GGC CGA CCC

1621  CAT GCA GAA CTC CAA CAT GTG CAT CTC CCT CAA GCT GAA CAG
      GTA CGT CTT GAG GTT GTA CAC GTA GAG GGA GTT CGA CTT GTC

1666  GAA GCT GCC GTT CCT CGA GGA GAT CTG GGA CGT GGA CCT GCA
      CTT CGA CGG CAA GGA GCT CCT CTA GAC CCT GCA CCT GGA CGT

1711  GGC GAC GAC GGC GGT GCC GGA GGC GGC GCC TCT AGA
      CCG CTG CTG CCG CCA CGG CCT CCG CCG CGG AGA TCT
```

Fig.2 iv.

```
1756 AGC CCC CGC CCC GCC CGC CGC CAC CGT CTA GCG CGC
     TCG GGG GCG GGG CGG GCG GCG GTG GCA GAT CGC GCG

1801 CTC AGG AGA GAA CGC TCA TAG ACT GGC TAG TTT TGA AGT GCA
     GAG TCC TCT CTT GCG AGT ATC TGA CCG ATC AAA ACT TCA CGT

1846 CGG ACA CTG ACG TCG ACG TGA TCA ACC TAT TTA TAA GGA CTG CGA
     GCC TGT GAC AGC TGC ACT AGT TGG ATA AAT ATT CCT GAC GCT

1891 ATT TTA CCA CTT AAG AGG GCA CAC CCG TAC CCG ATT TCG TAC GG
     TAA AAT GGT GAA TTC TCC CGT GTG GGC ATG GGC TAA AGC ATG CC
```

Total number of bases is: 1934.

Fig. 3.

The sequence shown below is that of pSK16.1

Sequence ID3

```
      3         9        15        21        27        33        39       45
      |         |         |         |         |         |         |        |
  1 CGC TGG TAT AAC AAC GGA CCA TTC CAG ACG CTG CGA ATG CTC GAG
    GCG ACC ATA TTG CCT GGT AAG GTC TGC GAC GCT TAC GAG CTC

46 GAG AGC TCG TCT GAG GTG ACG TCG TCT TCA GCA CTG GGC CTG CCG
    CTC TCG AGC AGA CTC CAC TGC AGC AGA AGT CGT GAC CCG GAC GGC

91 CCG GCT ATG GTG ATG TCC CCG GAA TCG CTC GCG TCG CCC GAG ATC
    GGC CGA TAC CAC AGG GGC CTT AGC GAG CGC AGC GGG CTC TAG

136 GGC GGC CTG GAG CTG TGG GGC TAC GAC GAT GGC ATC ACT TAC AGC
    CCG CCG GAC CTC GAC ACC CCG ATG CTG CTA CCG TAG TGA ATG TCG

181 ATG GCA CAG TCG CTG GGC ACC TGC ATG GAG CAG CAG CAG CCC
    TAC CGT GTC AGC GAC CCG TGG ACG TAC CTC GTC GTC GTC GGG
```

Fig. 3 i.

```
226  CAG CCG CAG CAG CCG CAG ACA CAA CCC CTA CCT TCC ATG
     GTC GGC GTC GGC GTC TGT GTT GGG GAT GGA AGG TAC

271  CCG TTA CCA ATG CCA CCG ACA ACA CCC AAA TCA GAA AAC GAG TCA
     GGC AAT GGT TAC GGT TGT TGT GGG TTT AGT CTT CTC AGT

316  ATG TCA TCA GGT CGT GAG GAA CTG TCT CCA GCT TCG AGT GTA AAC
     TAC AGT AGT CCA GCA CTC CTT GAC AGA GGT CGA AGC TCA CAT TTG

361  GGC TGC AGC ACA GAT GGC GAG GCG CTA TGT CTT GTC TGC GGC CCA
     CCG ACG TCG TGT CTA CCG CTC CGC GAT ACA GAA CAG CCG CCG GGT

406  GCG CCG AGG CAG CAA GAA GAG CTA TGT CTT GTC TGC GGC GAC AGA
     CGC GGC TCC GTT CTT CTC GAT ACA GAA CAG ACG CTG TCT

451  GCC TCC GGA TAT CAC TAC AAC GCG CTC ACA TGT GAA GGG TGT AAA
     CGG AGG CCT ATA GTG ATG TTG CGC GAG TGT ACA CTT CCC ACA TTT

496  GGT TTC TTC AGG CGG AGT GTA ACC AAA AAT GCA GTG TAC ATA TGC
```

Fig.3 ii.

```
      CCA AAG AAG TCC GCC TCA CAT TGG TTT TTA CGT CAC ATG TAT ACG
541   AAA TTC GGC CAT GCT TGC GAA ATG GAT ATC TAT ATG CGG AGA AAA
      TTT AAG CCG GTA CGA ACG CTT TAC CTA TAG ATA TAC GCC TCT TTT
586   TGT CAG GAG TGT CGG TTG AAG AAA TGT CTT GCG GTG GGC ATG AGG
      ACA GTC CTC ACA GCC AAC TTC TTT ACA GAA CGC CAC CCG TAC TCC
631   CCC GAG TGC GTG CCG CAG GAG AAC CAG TGT GCA ATG AAA CGG AAA
      GGG CTC ACG CAC GGC CTC TTG GTC ACA CGT TAC TTT GCC TTT
676   GAG AAA GCG CAG AGG GAA AAA GAC AAA TTG CCC GTC AGT ACG
      CTC TTT CGC GTC TCC CTT CTG TTT AAC GGG CAG TCA TGC
721   ACG ACA GTA GAC GAT CAC ATG CCT CCC ATC CAA TGT GAC CCT
      TGC TGT CAT CTG CTA GTG TAC GGG TAG GTT ACA CTG GGA
766   CCG CCC CCA GAG GCC GCT AGA ATT CTG GAA AAG CAG CAC GAG
      GGC GGG GGT CTC CGG TCT TAA GAC CTT GTC GTG CTC
811   GTG GTG CCA CGA TTC CTG AAT GAG AAG CTA ATG GAA CAG AAC AGA
      CAC GGT GCT AAG GAC TTA CTC TTC GAT TAC CTT GTC TTG TCT
856   TTG AAG AAC GTG CCC CCC CTC ACT GCC AAT CAG AAG TCG TTG ATC
      AAC TTC TTG CAC GGG GAG TGA CGG TTA GTC TTC AGC AAC TAG
901   GCA AGG CTC GTG TGG TAC CAG GAA GGC TAT GAA CAA CCT TCC GAG
      CGT TCC GAG CAC ACC ATG GTC CTT CCG ATA CTT GGA AGG CTC
946   GAA GAC CTG AAG AGG GTT ACA CAG TCG GAC GAG GAC GAA GAC
      CTT CTG GAC TTC TCC CAA TGT GTC AGC CTG CTC CTG CTT CTG
```

Fig.3 iii.

```
 991 TCG GAT ATG CCG TTC CGT CAG ATT ACC GAG ATG ACG ATT CTC ACA
     AGC CTA TAC GGC AAG GCA GTC TAA TGG CTC TAC TGC TAA GAG TGT

1036 GTG CAG CTC ATC GTA GAA TTC GCT AAG TTC CCG CTC CCG GGC GCC
     CAC GTC GAG TAG CAT CTT CGA CGA TTC AAG GGC GAG GGC CCG CGG

1081 AAG ATC TCG CAG GAC CTG CAG ATC ACG TTA TTA AAG GCG TGC TCA
     TTC TAG AGC GTC CTG GAC GTC TAG TGC AAT AAT TTC CGC ACG AGT

1126 AGT GAG GTG ATG ATG CTC CGA GCT GTG CGG CGG TAT GAC GCG GCG
     TCA CTC CAC TAC TAC GAG GCT CGA CAC GCC ATA CTG CGC CGC CGG

1171 ACC GAC AGC GTA CTG TTC GCG AAC AAC CAG GCG TAC ACT CGC GAC
     TGG CTG TCG CAT GAC AAG CGC TTG TTG GTC CGC ATG TGA GCG CTG

1216 AAC TAC CGC AAG GCA GGC ATG GCG TAC GTC ATC GAG GAC CTG CTG
     TTG ATG GCG TTC CGT CCG TAC CGC CAG TAG CTC CTG GAC GAC GAC

1261 CAC TTC TGT CGG TGC ATG TAC ATG ATG GAT AAC GAT ATG GTG CAT
     GTG AAG ACA GCC ACG TAC ATG TAC TAC CTA TTG CTA CAC GTA

1306 TAT GCG CTG CTT ACA GCC ATT GTC TTC ATC GAC CGG CCC GGG
     ATA CGC GAC GAA TGT CGG TAA CAG TAG AAG CTG GCC GGG CCC

1351 CTT GAG CAA CCC CTG TTG GTG GAG GAC ATC TCA CAG AGA TAT TAC CTG
     GAA CTC GTT GGG GAC AAC CAC CTC CTG TAG GTC TCT ATA ATG GAC

1396 AAC ACG CTA CGG GTG TAC ATC CTG AAC CAG TTG AAC AGC GCG TCG CCC
     TTG TGC GAT GCC CAC ATG TAG GAC TTG GTC AAC TTG TCG CGC AGC GGG

1441 CGC GGC GCC GTC TTC GGC ATC CTG GAG ATC CTG GGC ATA CTG ACG GAG
```

Fig. 3 iv.

```
      GCG CCG CGG CAG TAG AAG CCG CTC TAG GAC CCG TAT GAC TGC CTC

1486  ATC CGC ACG CTG GGC ATG GGC CTG CAG GTC TTC AAC ATG TCC CTC
      TAG GCG TGC GAC CCG TAC CCG GAC GTC CAG AAG TTG TAC AGG GAG

1531  AAG CTG AAG AAC AGG AAG CTG TTC CCG TTC GAG GAG ATC TGG ACC
      TTC GAC TTC TTG TCC TTC GAC AAG GGC AAG CTC CTC TAG ACC TGG

1576  GAC GTG GCG GAC GTG GCG ACG CCG ACG GCG CCG GTG GCG GCG GAG
      CTG CAC CGC CTG CAC CGC TGC GGC TGC CGC GGC CAC CGC CGC CTC

1621  GCG CCG GCG CCT CTA GCC CCC CCC GCC CCG CCC GGC CCC GCC CGG
      CGC GGC CGC GGA GAT CGG GGG GGG CGG GGC GGG CCG GGG CGG GCC

1666  ACC GTC TAG CGC GCC TCA GGA GAG AAC GCT CAT AGA CTG GCT AGT
      TGG CAG ATC GCG CGG AGT CCT CTC TTG CGA GTA TCT GAC CGA TCA

1711  TTT AGT GAA GTG CAC GGA CAC TGA CGT CGA CGT GAT CAA CCT ATT
      AAA TCA CTT CAC GTG CCT GTG ACT GCA GCT GCA CTA GTT GGA TAA

1756  TAT AAG GAC TGC GAA TTT TAC CAC TTA AGA GGG CAC ACC CGT ACC
      ATA TTC CTG ACG CTT AAA ATG GTG AAT TCT CCC GTG TGG GCA TGG

1801  CGA TTT CGT ACG TAT TCG GTG ACC GAC GAT GCA GAG CGT GTG
      GCT AAA GCA TGC ATA AGC CAC TGG CTG CTA CGT CTC GCA CAC

1846  TAA TGT GAA TAT ATG TGT TGA ACG ATT TGG AGA ATA TAT ATT
      ATT ACA CTT ATA TAC ACA ACT TGC TAA ACC TCT TAT ATA TAA

1891  GGT GTT GCT GTT CGG GCC ACG CCG TCG CCG GGC GGC GAT CTA
      CCA CAA CGA CAA GCC CGG TGC GGC AGC GGC CCG CCG CTA GAT
```

Fig.3 v.

```
1936  CGC GGC GCC CGC GGC TTC AGT TTT ATT TCG TTT ACG ACT GAG TTG
      GCG CCG CGG GCG CCG AAG TCA AAA TAA AGC AAA TGC TGA CTC AAC

1981  GTC ACT CGG ATA CGA CTG TAT GAT AAG ACT TCG TTC GAT AAG TAC
      CAG TGA GCC TAT GCT GAC ATA CTA TTC TGA AGC AGC CTA TTC ATG

2026  ACC TAC TAA ATT ACA CAT ACG TAC GTA GCT TAC GAG AGT TAT TAG
      TGG ATG ATT TAA TGT GTA TGC ATG CGA CTC TCA ATA ATC

2071  AGA CAA AGA ATA TAA GAA GAT GTT TCT ATT GGG TGA AAA GTT
      TCT GTT TCT TAT ATT CTT CAA AGA TAA CCC ACT TTT CAA

2116  GAT AGT TAT GTT TAT TTA CCA AAA TTA ACA ATA CGT TGA TTA
      CTA TCA ATA CAA ATA AAT GGT TTT AAT TGT GCA ACT AAT

2161  ACC TTT CGA GTA TAA TAT TGT GAT CTA TGT GAG TCG GCT GTC CAC GTC
      TGG AAA GCT CAT ATT ATA ACA CTA GAT ACA CTC AGC AGG CGA CAG GTG CAG

2206  GCC GTC ACA TGT TTG CTG ATG CAC ACG TGA GGN GCG TTA TCG
      CGG CAG TGT ACA AAC GAC GTG TGC ACT CCN CGC AAT AGC

2251  TGT TTC ATG GTT CCA TCG TCC TGT GCC CGC GAC CCT CGA CTA AAT
      ACA AAG TAC CAA GGT AGC AGG ACA CGG GCG CTG GGA GCT GAT TTA

2296  GAG TAA TTT AAT TTA CTG TGA CAT TTT AAT GTG TTG ATT
      CTC ATT AAA TTA GAC ACT AAC GTA AAA CAC AAC TAA

2341  ATC TAC CAT AGG GTG ATA TAA GTG TGT CTT ATT ACA ATA CAA AGT
      TAG ATG GTA TCC CAC TAT ATT CAC ACA GAA TAA TGT TAT GTT TCA

2386  GTG TGT CGT CGA TAG CTT CCA CAC GAG CAA GCC TTT TGT TTA AGT
```

Fig.3 vi.

```
              CAC ACA GCA GCT ATC GAA GGT GTG CTC GTT CGG AAA ACA AAT TCA
2431 GAT TTA CTG ACA TGG ACA CTC GAC CCG GAA CTT C
     CTA AAT GAC TGT ACC TGT GAG CTG GGC CTT GAA G
```

Total number of bases is: 2464.

Fig.4.

Sequence ID 4

```
         10         20         30         40         50         60
         |          |          |          |          |          |
ACTCGGCGTGCTCTTCTCACCTGTTGCTCGGATTGTGTTGTACTAGAAAAAAGTTGTCGCC 70         80         90        100        110        120
         |          |          |          |          |          |
GCTCGAACGAGACTTCCGAGTCCTATTGGATTGCACGAAAGTCGAGACAGTGGATAGCGA 130        140        150        160        170        180
         |          |          |          |          |          |
TTCGGTTTCGTTTGAACGTTGCGTAGACGAGTGGTGCATGTCCATGAGTCGCGTTTAGAT
```

Fig.4 i.

```
         190       200       210       220       230       240
          |         |         |         |         |         |
AGTTTAGTGCGAGGAAAAAGTGAAAGCCTTCCTCGGAGGATGTCCCTCGGCGCTC
                                              M  S  L  G  A 250       260       270       280       290       300
          |         |         |         |         |         |
GTGGATACCGGAGGTGTGACACGCTCGCCGACATGAGACGCCGCTGGTATAACAACGGAC
 R  G  Y  R  R  C  D  T  L  A  D  M  R  R  R  W  Y  N  N  G 310       320       330       340       350       360
          |         |         |         |         |         |
CATTCCAGACGCTGCGAATGCTCGAGGAGAGCTCGTCTGAGGTGACGTCGTCTTCAGCAC
 P  F  Q  T  L  R  M  L  E  E  S  S  S  E  V  T  S  S  S  A 370       380       390       400       410       420
          |         |         |         |         |         |
TGGGCCTGCCGCCGGCTATGGTGTCCCGGAATGTCGATGTCGCGTCGCCGAGATCGGGCG
 L  G  L  P  P  A  M  V  M  S  P  E  S  L  A  S  P  E  I  G
```

Fig.4 ii.

```
                430         440         450         460         470         480
                 |           |           |           |           |           |
              GCCTGGAGCTGTGGGCTACGACGATGGCATCACTTACAGCATGGCACAGTCGCTGGGCA
               G  L  E  L  W  G  Y  D  D  G  I  T  Y  S  M  A  Q  S  L  G 490         500         510         520         530         540
                 |           |           |           |           |           |
              CCTGCACCATGGAGCAGCAGCCCCAGCCGCAGCAGCCGCAGCAGACACAACCCC
               T  C  T  M  E  Q  Q  Q  P  Q  P  Q  Q  P  Q  Q  T  Q  P 550         560         570         580         590         600
                 |           |           |           |           |           |
              TACCTTCCATGCCGTTACCAATGCCACCGACAACACCCAAATCAGAAAACGAGTCAATGT
               L  P  S  M  P  L  P  M  P  P  T  T  P  K  S  E  N  E  S  M 610         620         630         640         650         660
                 |           |           |           |           |           |
              CATCAGTCGTGAGGAACTGTCTCCAGCTTCGAGTGTAAACGGCTGCAGCACAGATGGCG
               S  S  G  R  E  E  L  S  P  A  S  S  V  N  G  C  S  T  D  G 670         680         690         700         710         720
                 |           |           |           |           |           |
              AGGCGAGGCGGCAGAAGAAAGGCCCAGCCGCCGAGGCAGCAAGAAGAGCTATGTCTTGTCT
               E  A  R  R  Q  K  K  G  P  A  P  R  Q  Q  E  E  L  C  L  V
```

Fig.4 iii.

```
              730       740       750       760       770       780
               |         |         |         |         |         |
         GCGGCGACAGAGCCTCCGGATATCACTACAACGCGCTCACATGTGAAGGTGTAAAGGTT
          C  G  D  R  A  S  G  Y  H  Y  N  A  L  T  C  E  G  C  K  G 790       800       810       820       830       840
               |         |         |         |         |         |
         TCTTCAGGCGGAGTGTAACCAAAAATGCAGTGTACATATGCAAATTCGGCCATGCTTGCG
          F  F  R  R  S  V  T  K  N  A  V  Y  I  C  K  F  G  H  A  C 850       860       870       880       890       900
               |         |         |         |         |         |
         AAATGGATATCTATATGCGGAGAAAATGTCAGGAGTGTCGGTTGAAGAAATGTCTTGCGG
          E  M  D  I  Y  M  R  R  K  C  Q  E  C  R  L  K  K  C  L  A 910       920       930       940       950       960
               |         |         |         |         |         |
         TGGGCATGAGGCCCGAGTGCGTGGTGCCGGAGAACCAGTGTGCAATGAAACGGAAAGAGA
          V  G  M  R  P  E  C  V  V  P  E  N  Q  C  A  M  K  R  K  E 970       980       990      1000      1010      1020
               |         |         |         |         |         |
         AAAAGGCGCAGAGGGAAAAGACAAATTGCCCGTCAGTACGACGACAGTAGACGATCACA
          K  K  A  Q  R  E  K  D  K  L  P  V  S  T  T  T  V  D  D  H
```

Fig.4 iv.

```
            1030       1040       1050       1060       1070       1080
              |          |          |          |          |          |
TGCCTCCCATCATGCAATGTGACCCTCCGCCCCCAGAGGCCGCTAGAATTCTGGAATGTG
  M  P  P  I  M  Q  C  D  P  P  P  P  E  A  A  R  I  L  E  C 1090       1100       1110       1120       1130       1140
              |          |          |          |          |          |
TGCAGCACGAGGTGGTGCCACGATTCCTGAATGAGAAGCTAATGGAACAGAACAGATTGA
  V  Q  H  E  V  V  P  R  F  L  N  E  K  L  M  E  Q  N  R  L 1150       1160       1170       1180       1190       1200
              |          |          |          |          |          |
AGAACGTGCCCCCCTCACTGCCAATCAGAAGTCGTTGATCGCAAGGCTCGTGTGGTACC
  K  N  V  P  P  L  T  A  N  Q  K  S  L  I  A  R  L  V  W  Y 1210       1220       1230       1240       1250       1260
              |          |          |          |          |          |
AGGAAGGCTATGAACAACCTTCCGAGGAAGACCTGAAGAGGGTTACACAGTCGGACGAGG
  Q  E  G  Y  E  Q  P  S  E  E  D  L  K  R  V  T  Q  S  D  E
```

Fig. 4 v.

```
     1270       1280       1290       1300       1310       1320
       |          |          |          |          |          |
ACGACGAAGACTCGGATATGCCGTTCCGTCAGATTACCGAGATGACGATTCTCACAGTGC
 D  D  E  D  S  D  M  P  F  R  Q  I  T  E  M  T  I  L  T  V 1330       1340       1350       1360       1370       1380
       |          |          |          |          |          |
AGCTCATCGTAGAATTCGCTAAGGGCCTCCCGGGCTTCGCCAAGATCTCGCAGTCGGACC
 Q  L  I  V  E  F  A  K  G  L  P  G  F  A  K  I  S  Q  S  D 1390       1400       1410       1420       1430       1440
       |          |          |          |          |          |
AGATCACGTTATTAAAGGCGTGCTCAAGTGAGGTGATGATGCTCCGAGTGGCTCGGCGGT
 Q  I  T  L  L  K  A  C  S  S  E  V  M  M  L  R  V  A  R  R 1450       1460       1470       1480       1490       1500
       |          |          |          |          |          |
ATGACGCGGCCACCGACAGCGTACTGTTCGCGAACAACCAGGCGTACACTCGCGACAACT
 Y  D  A  A  T  D  S  V  L  F  A  N  N  Q  A  Y  T  R  D  N
```

Fig.4 vi.

```
      1510      1520      1530      1540      1550      1560
       |         |         |         |         |         |
ACCGCAAGGCAGGCATGGCGTACGTCATCGAGGACCTGCTGCACTTCTGTCGGTGCATGT

Y  R  K  A  G  M  A  Y  V  I  E  D  L  L  H  F  C  R  C  M 1570      1580      1590      1600      1610      1620
       |         |         |         |         |         |
ACTCCATGATGATGGATAACGTGCATTATGCCTTACAGCCATTGTCATCTTCTCAG

Y  S  M  M  M  D  N  V  H  Y  A  L  L  T  A  I  V  I  F  S 1630      1640      1650      1660      1670      1680
       |         |         |         |         |         |
ACCGGCCCCGGGCTTGAGCAACCCCTGTTGGTGGAGGAGATCCAGAGATATTACCTGAACA

D  R  P  G  L  E  Q  P  L  L  V  E  E  I  Q  R  Y  Y  L  N 1690      1700      1710      1720      1730      1740
       |         |         |         |         |         |
CGCTACGGGGTGTACATCCTGAACCAGAACAGCGCGTCGCCCCGCGGCGCCGTCATCTTCG

T  L  R  V  Y  I  L  N  Q  N  S  A  S  P  R  G  A  V  I  F
```

Fig. 4 vii.

```
       1750        1760        1770        1780        1790        1800
         |           |           |           |           |           |
GCGAGATCCTGGGCATACTGACGGAGATCCGCACGCTGGGCATGCAGAACTCCAACATGT
 G   E   I   L   G   I   L   T   E   I   R   T   L   G   M   Q   N   S   N   M 1810        1820        1830        1840        1850        1860
         |           |           |           |           |           |
GCATCTCCCTCAAGCTGAAGAACAGGAAGCTGCCGCCGTTCCTCGAGGAGATCTGGGACG
 C   I   S   L   K   L   K   N   R   K   L   P   P   F   L   E   E   I   W   D 1870        1880        1890        1900        1910        1920
         |           |           |           |           |           |
TGGCGGACGTGGCGACGACGGCCGTGGCCGTGGCGGAGGCGCCGGCGCCTCTAGCCC
 V   A   D   V   A   T   T   A   T   P   V   A   A   E   A   P   A   P   L   A 1930        1940        1950        1960        1970        1980
         |           |           |           |           |           |
CCGCCCCCGCCCGCCCGCCCCGCCTCAGCGCGCCTCAGGAGAGAACGCTCATA
 P   A   P   P   A   R   P   P   P   A   T   V   -

1990        2000        2010        2020        2030        2040
         |           |           |           |           |           |
GACTGGCTAGTTTTAGTGAAGTGCACGGACACTGACGTGATCAACCTATTTATA
```

Fig.4 viii.

```
         2050       2060       2070       2080       2090       2100
          |          |          |          |          |          |
AGGACTGCGAATTTTACCACTTAAGAGGGCACACCCGTACCCGATTTCGTACGTATTCGG 2110       2120       2130       2140       2150       2160
          |          |          |          |          |          |
TGACCGACGACGATGCAGAGCGTGTGTAATGTGAATATATGTGTTGTTGAACGATTTGGA 2170       2180       2190       2200       2210       2220
          |          |          |          |          |          |
GAATATATATTGGTGTGTTGCTGTGTTCGGCCCGCACGCCGTCGCCGGCGATCGCG 2230       2240       2250       2260       2270       2280
          |          |          |          |          |          |
GCGCCCCGGCTTCAGTTTTTATTTCGTTTACGACTGAGTTGGTCACTCGGATACGACTGT 2290       2300       2310       2320       2330       2340
          |          |          |          |          |          |
ATGATAAGACTTCGTTCGATAAGTACACCTACTAAATTACACATACGTAGCTTACG 2350       2360       2370       2380       2390       2400
          |          |          |          |          |          |
AGAGTTATTAGAGACAAAGAATATAAGAAGAAGATGTTTCTATTGGGTGAAAAGTTGATA
```

```
         2410        2420        2430        2440        2450        2460
          |           |           |           |           |           |
GTTATGTTTATTACCAAAATTAACAATAATACGTTGATTAACCTTTCGAGTATAATATT 2470        2480        2490        2500        2510        2520
          |           |           |           |           |           |
GTGATGAGTCGTCCGCTGTCCACGTCGCCGTCACATGTTTGTTTCTGATGCACACGTGAG 2530        2540        2550        2560        2570        2580
          |           |           |           |           |           |
GNGCGTTATCGTCGTGTTTCATGGTTCCATCGTCCTGTGCCCGCGACCCTCGACTAAATGAGT 2590        2600        2610        2620        2630        2640
          |           |           |           |           |           |
AATTTAATTATTGCTGTGATTACATTTAATGTGTTGATTATCTACCATAGGGTGATAT 2650        2660        2670        2680        2690        2700
          |           |           |           |           |           |
AAGTGTCTTATTACAATACAAAGTGTGTCGTCGATAGCTTCCACGAGCAAGCCT 2710        2720        2730        2740
          |           |           |           |
TTTGTTTAAGTGATTACTGACACATGGACACTCGACCCGGAACTTC
```

```
Sequence I.D. 5

BmECR    MRVENVDNVS                                                        10
MsECR    M---------
HvECR    M---------                                                         1
CtECR    ----------
AaECR    ----------
DmECR    ----------

BmECR    FALNGRADEWCMSVETRLDSLVREKSEVKAYVGGCPSVITDAGAYDALFD                60
MsECR    --------------------------------------------------
HvECR    -SLGARGYRRC---------------------------------DTLAD                 16
CtECR    --------------------------------------------------
AaECR    --------------------------------------------------
DmECR    --------------------------------------------------

BmECR    M-RRRWSNNGGFP-LRMLEESSSEVTSSSA-LGLPPAMVMSPESLASPEY               107
MsECR    M-RRRWSNNGCFP-LRMFEESSSEVTSSSA-FGMPAAMVMSPESLASPEY                47
HvECR    M-RRRWYNNGGFQTLRMLEESSSEVTSSSA-LGLPPAMVMSPESLASPEI                64
CtECR    M-K----------TENLIVTT-VKVEPLNYASQSF                               23
AaECR    MMKRRWSNNGGFTALRMLDDSSSEVTSSSAAL---GMTMSPNSLGSPNY                 46
DmECR    M-KRRWSNNGGF--MRLPEESSSEVTSSSNGLVLPSGVNMSPSSLDSHDY                47
         *                    . .  .           . . *. . .
```

Fig. 5 i.

```
BmECR   GALELW-------SY------------------------------------------------                          114
MsECR   GGLELW-------SY------------------------------------------------                           55
HvECR   GGLELW-------GY------------------------------------------------                           72
CtECR   GDNNI-----YGGAT------------------------------------------------                           33
AaECR   DELELW-SSYEDNAYNGHSV--LSNGNNN---------LGGCGA-------------------                           78
DmECR   CDNDKWLCGNESGSFGGSNGHGLSQQQQSVITLAMHGCSSTLPAQTTIIP                                         97

BmECR   ----------------------------------------------------DDGITY                               121
MsECR   ----------------------------------------------------DETMTN                                61
HvECR   ----------------------------------------------------DDGIT-                                77
CtECR   ----------------------------------------------------------                                46
AaECR   ------------------------------------KKQRLESDETMNH                                         98
DmECR   INGNANGNGGSTNGQYVPGATNLGALANGMLNGGFNGMQQQIQNGHGLIN                                        147

BmECR   NTAQSLLGACNMQQQQLQP------------------------QQPHPAPPTLPTMP-----                            154
MsECR   YPAQSLLGACNAPQQQQQQ------------------------QQQQPSAQPLPSMP-----                             94
HvECR   YSMAQSLGTCTMEQQQPQP------------------------QQQPQQTQPLPSMP-----                            114
CtECR   NQTNMNLESSNMNHNTIS---------GFSSPDVNYEAYSPNSKL------DDGN                                    86
AaECR   MASQAVQANANSIQHIVGN----------------------LINGVNPNQTLIPPLPS---                             134
DmECR   STTPSTPTTPLHLQQNLGGAGGGIGGMGILHHANGTPNGLIGVVGGGGG                                         197

BmECR   ------------LPMPPTTPKSENESMSSGREELSPASSINGCSADA--D                                        190
MsECR   ------------LPMPPTTPKSENESMSSGREELSPASSINGCSTDG--E                                        130
HvECR   ------------LPMPPTTPKSENESMSSGREELSPASSVNGCSTDG--E                                        146
CtECR   MSVHMGDG----------------------------------LDG------K                                       98
AaECR   ------------IIQNTLMNTPRSESVNSISSGREDLSPSSLNGYT--DGSD                                      173
DmECR   VGLGVGGGGVGGLGMQHTPRSDSVNSISSGRDDLSPSSSLNGYSANESCD                                        247
                                                                *
```

Fig. 5 ii.

```
BmECR  ARRQKKGPAPRQQEELCLVCGDRASGYHYNALTCEGCKGFFRRSVTKNAV  240
MsECR  PRRQKKGPAPRQQEELCLVCGDRASGYHYNALTCEGCKGFFRRSVTKNAV  180
HvECR  ARRQKKGPAPRQQEELCLVCGDRASGYHYNALTCEGCKGFFRRSVTKNAV  196
CtECR  KSSSKKGPVPRQQEELCLVCGDRASGYHYNALTCEGCKGFFRRSVTKNAV  148
AaECR  AKKQKKGPTPRQQEELCLVCGDRASGYHYNALTCEGCKGFFRRSVTKNAV  223
DmECR  AKKSKKGPAPRVQEELCLVCGDRASGYHYNALTCEGCKGFFRRSVTKSAV  297
       .****.**..**.***************************.**

BmECR  YICKFGHACEMDMYMRRKCQECRLKKCLAVGMRPECVIQEPS-KNKDRQR  289
MsECR  YICKFGHACEMDMYMRRKCQECRLKKCLAVGMRPECVVPESTCKNKRREK  230
HvECR  YICKFGHACEMDIYMRRKCQECRLKKCLAVGMRPECVVPENQCAMKRKEK  246
CtECR  YCCKFGHECEMDMYMRRKCQECRLKKCLAVGMRPECVVPENQCAIKRKEK  198
AaECR  YCCKFGHACEMDMYMRRKCQECRLKKCLAVGMRPECVVPENQCAIKRKEK  273
DmECR  YCCKFGRACEMDMYMRRKCQECRLKKCLAVGMRPGCVVPGNQCAMKRREK  347
       *.***..**** .*****************.**..*..* *:.

BmECR  QKKDKGILLPVSTTTV---------------------------EDHMPPIMQC  315
MsECR  EAQREKDKLPVSTTTV---------------------------DDHMPAIMQC  256
HvECR  KAQREKDKLPVSTTTV---------------------------DDHMPPIMQC  272
CtECR  KAQKEKDKVPGIVGSNTSSSSLLNQSLNNGSLKNLEISYREELLQQLMKC  248
AaECR  KAQKEKDKVQTNAT--------------VSTTNSTY-RS-----EILPILMKC  306
DmECR  KAQKEKDKMTTSPSSQHGGNGSLASGGGQDFVKK----------EILD-LMTC  389
       .: .* :**                                   *

BmECR  DPPPPEAARI-------HEVVPRYLSEKLMEQNRQKNIPPLSANQKSLIARL  360
MsECR  DPPPPEAARI-------HEVVPRFLTEKLMEQNRLKNVTPLSANQKSLIARL  301
HvECR  DPPPPEAARILECVQHEVVPRFLNEKLMEQNRLKNVPPLTANQKSLIARL  322
CtECR  DPPPHPMQQLL--------------PEKLLMENRAKGTPQLTANQVAVIYKL  286
AaECR  DPPPHQAIPLL--------------PEKLLQENRLRNIPLLTANQMAVIYKL  344
DmECR  EPPQHATIPLL--------------PDEILAKCQARNIPSLTYNQLAVITKL  427
       :**    .                  *..: . :  . . *.**.*:..*
```

Fig.5 iii.

```
BmECR  VWYQEGYEQPSDEDLKRVTQTWQ-SDEEDEESDLPFRQITEMTILTVQLI   409
MsECR  VMYQEGYEQPSEEDLKRVTQTWQLEEEEEEETDMPFRQITEMTILTVQLI   351
HvECR  VWYQEGYEQPSEEDLKRVTQS----DEDDEDSDMPFRQITEMTILTVQLI   368
CtECR  IWYQDGYEQPSEEDLKRITTE--LEEEEDQEHEANFRYITEVTILTVQLI   334
AaECR  IWYQDGYEQPSEEDLKRIMIG--SPNEEEDQHDVHFRHITEITILTVQLI   392
DmECR  IWYQDGYEQPSEEDLRRIM-S--QPDENESQTDVSFRHITEITILTVQLI   474
       .*.*.*******.*****.**.  .  .     .  ** .*.**.*******

BmECR  VEFAKGLPGFSKISQSDQITLLKASSSEVMLRVARRYDAASDSVLFANN   459
MsECR  VEFAKGLPGFSKISQSDQITLLKASSSEVMMLRVARRYDAATDSVLFANN   401
HvECR  VEFAKGLPGFAKISQSDQITLLKACSSEVMLRVARRYDAATDSVLFANN   418
CtECR  VEFAKGLPAFIKIPQEDQITLLKACSSEVMLRMARRYDHDSDSILFANN   384
AaECR  VEFAKGLPAFTKIPQEDQITLLKACSSEVMLRMARRYDAATDSILFANN   442
DmECR  VEFAKGLPAFTKIPQEDQITLLKACSSEVMLRMARRYDHSSDSIFFANN   524
       ********.*  ** *.***********.*****.******  .*.*****

BmECR  KAYTRDNYRQGGMAYVIEDLLHFCRCMFAMGMDNVHFALLTAIVIFSDRP   509
MsECR  QAYTRDNYRKAGMSYVIEDLLHFCRCMYSMSMDNVHYALLTAIVIFSDRP   451
HvECR  QAYTRDNYRKAGMAYVIEDLLHFCRCMYSMMMDNVHYALLTAIVIFSDRP   468
CtECR  TAYTKQTYQLAGMEETIDDLLHFCRQMYALSIDNVETALLTAIVIFSDRP   434
AaECR  RSYTRDSYRMAGMADTIEDLLHFCRQMFSLTVDNVEYALLTAIVIFSDRP   492
DmECR  RSYTRDSYKMAGMADNIEDLLHFCRQMFSMKVDNVEYALLTAIVIFSDRP   574
        .**  *      *   *******.*     **   ***********

BmECR  GLEQPSLVEEIQRYYLNTLRIYIINQNSASSRCAVIYGRILSVLTELRTL   559
MsECR  GLEQPLLVEEIQRYYLNTLRVYILNQHSASPRCAVLFGKILGVLTELRTL   501
HvECR  GLEQPLLVEDIQRYYLNTLRVYILNQNSASPRGAVIFGEILGILTEIRTL   518
CtECR  GLEKAEMVDIIQSYYTETLKVYIVRDHGGESRCSVQFAKLLGILTELRTM   484
AaECR  GLEQAELVEHIQSYYIDTLRIYILNRHAGDPKCSVIFAKLLSILTELRTL   542
DmECR  GLEKAQLVEAIQSYYIDTLRITILNRHCGDSMSLVFYAKLLSILTELRTL   624
       ***  .   . * ** . *  *      .        * . ***.**
```

Fig.5 iv.

| | | |
|---|---|---|
| BmECR | GTQNSNMCISLKLKLKNRKLPPFLEEIWDVAEVARR------------------------ | 593 |
| MsECR | GTQNSNMCISLKLKLKNRKLPPFLEEIWDVAEVSTT------------------------ | 535 |
| HvECR | GMQNSNMCISLKLKKRKLPPFLEEIWDVADVATT-------------------------- | 552 |
| CtECR | GNLNSEMCFSLKLKNRKLPRFLEEVWDVGDVNNQTTATTNTENIVRERIN---------- | 534 |
| AaECR | GNQNSEMCFSLKLKNRKLPRFLEEIWDVQDIPPSMQAQMHSHGTQSSS------------ | 590 |
| DmECR | GNQNAEMCFSLKLKNRKLPKFLEEIWDVHAIPPSVQSHLQITQEEDERLE---------- | 674 |
| | * * . * * . * * * * . . * * * * . . * * * * * * * * * * . : : | |
| BmECR | ------------------------------------------------------------ | 593 |
| MsECR | ------------------------------------------------------------ | 535 |
| HvECR | ------------------------------------------------------------ | 552 |
| CtECR | RN---------------------------------------------------------- | 536 |
| AaECR | ----SSSSSSSSSNGSSNGNSSSNSNSSQHGPHPHPHGQQ--LTPNQ------------- | 632 |
| DmECR | RAERMRASVGGAITAGIDCDSASTSAAAAAQHQPQPQPQPSSLTQND------------- | 724 |
| BmECR | ---------HPTV-------LPPTNPVVL------------------------------ | 606 |
| MsECR | ---------QP--TPGVAAQVTPIVVDNPAAL--------------------------- | 556 |
| HvECR | ---------ATPVAAEAPAPLAPAPPARPATV--------------------------- | 575 |
| CtECR | ------------------------------------------------------------ | 536 |
| AaECR | ------------------------------------------------------V---- | 645 |
| DmECR | SQHQTQPQLQPQLPPQLQGQLQPQLQPQLQTQLQPQIQPQLLPVSAPV----------- | 774 |
| BmECR | ------------------------------------------------------------ | 606 |
| MsECR | ------------------------------------------------------------ | 556 |
| HvECR | ------------------------------------------------------------ | 575 |
| CtECR | ------------------------------------------------------------ | 536 |
| AaECR | HANGSGGGGSNNNSSSG------------------------------------------- | 663 |
| DmECR | PASVTAPGSLSAVSTSSEYMGGSAAIGPITPATTSSITAAVTASSTTSAV--------- | 824 |

Fig.5 v.

```
BmECR  ------------------------------------------------------  606
MsECR  ------------------------------------------------------  556
HvECR  ------------------------------------------------------  575
CtECR  ------------------------------------------------------  536
AaECR  ----GVVPGLGMLDQV--------------------------------------  675
DmECR  PMGNGVGVGVGVGGNVSMYANAQTAMALMGVALHSHQQQLIGGVAVKSEH       874

BmECR  ----  606
MsECR  ----  556
HvECR  ----  575
CtECR  ----  536
AaECR  ----  675
DmECR  STTA  878
```

Fig.40.

Spodoptera exigua DNA sequence.

Sequence ID 6

SPODOPTERA EXIGUA HINGE AND LIGAND BINDING DOMAINS

```
             3         9        15        21        27        33        39        45
             |         |         |         |         |         |         |         |
  1   AGG CCG GAG TGC ACG GTG CAC CCA GAA AAC CAG TGT GCA ATG AAA AGG
      TCC GGC CTC ACG TGC CAC GGT CTT TTG GTC ACA CGT TAC TTT TCC

46   AAA GAG AAA AAG GCA CAA AGG GAA AAA GAC AAG TTG CCA GTC AGT
      TTT CTC TTT TTC CGT GTT TCC CTT TTT CTG TTC AAC GGT CAG TCA

91   ACA ACG GTG GAT CTA GAG CTC AAG CAC ATG CCT CCC ATT ATG CAG TGT GAT
      TGT TGC CAC CTA GAT CTC GAG TTC GTG TAC GGA GGG TAA TAC GTC ACA CTA

136   CCA CCT CCA GGT GCC CGG AGA ATT CAC GAG GTG CCA CGA
      GGT GGA GGT CTC CGG GCC TCT TAA GTG CTC CAC GGT GCT

181   TTC CTG AAT GAA CTT TTC GAT AAC CTG GAC AGG ACA AGG CTC GAG AAG AAT GTG
      AAG GAC TTA CTT GAA AAG CTA TTG GAC CTG TCC TGT TCC GAG TTC TTA CAC

226   CCC CCT CAC TGC CAA CCA GAA GTC CTT AAT AGC GAG GCT GGT CTG
      GGG GGA GTG ACG GTT GGT CTT CAG GAA TTA TCG CTC CGA CCA GAC

271   GTA CCA AGA AGG CTA TGA ACA GCC ATC AGA AGA TCT AAA AAG
      CAT GGT TCT TCC GAT ACT TGT CGG TAG TCT CCT AGA TTT TTC
```

Fig.40 i.

```
316  AGT CAC ACA GTC GGA TGA AGA AGA GTC GGA CAT GCC GTT
     TCA GTG TGT CAG CCT ACT TCT TCT CAG CCT GTA CGG CAA

361  CCG TCA GAT CAC CGA GAT GAC CCT CAC AGT GCT CAT TGT
     GGC AGT CTA GTG GCT CTA CTG GGA GTG TCA CGA GTA ACA

406  TGA ATT CGC TAA GGG CCT ACC GTT CGC AGC CCT AAA GAT CTC ACA GTC
     ACT TAA GCG ATT CCC GGA TGG CAA GCG TCG GGA TTT CTA GAG TGT CAG

451  GGA TCA GAT CAC ATT ATT AAA GGC CTG TTC GAG GGT GAT GAT
     CCT AGT CTA GTG TAA TAA TTT CCG GAC AAG CCA CTA CTA

496  GTT GCG AGT AGC TCG GCG GTA GCG CGC GAC CGT AGA CAG CGT GTT
     CAA CGC TCA TCG AGC CGC CAT CGC GCG CTG GCA TCT GTC GCA CAA

541  GTT CGC CAA CAA CCA GGC GTA CAT CGA GCT GCT GAT CTT GCA GGC CGG
     CAA GCG GTT GTT GGT CCG CAT GTA GCT CGA CGA CTA GAA CGT CCG GCC

586  AGG CAT GGC CTA CGT CAT GAT GAT CGA GGA CCT CCT CTG CCG GTG
     TCC GTA CCG GAT GCA GTA CTA CTA GCT CCT GGA GAA GAC GGC CAC

631  CAT GTA CTC CAT GAT GAT CTA CGT CCA TAA CGT CTA TGC ACT GCT CAC
     GTA CAT GAG GTA CTA CTA GAT GCA GGT ATT GCA GAT ACG TGA CGA GTG

676  TGC CAT CGT CAT TTT CTC AGA CCG ACC CGG GCT TGA GCT AAC CCT
     ACG GTA GCA GTA AAA GAG TCT GGC TGG GCC TCT ACT CGA TTG GGA

721  GTT GGT GGA GGA GAT CCA GAG ATA TTA CCT GAA CAC GCT GGT
     CAA CCA CCT CCT CTA GGT CTC TAT AAT GGA CTT GTG CGA CCA
```

Fig. 40 ii.

```
766  GTA CAT CCT GAA CCA GAA CAG TCG GTC GCC GTG CTG CCC TGT CAT
     CAT GTA GGA CTT GGT CTT GTC AGC CAG CGG CAC GAC GGG ACA GTA

811  CTA CGC TAA GAT CCT CGG CAT CCT GAC GGA GCT GCG GAC CCT GGG
     GAT GCG ATT CTA GGA GCC GTA GGA CTG CCT CGA CGC CTG GGA CCC

856  CAT GCA GAA CTC CAA CAT GTG CAT CTC ACT CAA GCT GAA GAA CAG
     GTA CGT CTT GAG GTT GTA CAC GTA GAG TGA GTT CGA CTT CTT GTC

901  GAA CGT GCC GTT CTT CGA GGA TAT CTG GGA CGT CCT CGA GTA
     CTT GCA CGG CAA GAA GCT CCT ATA GAC CCT GCA GGA GCT CAT

946  AAA
     TTT
```

Total number of bases is: 948.

Fig. 41.

Sequence I.D. 7

Sequence comparison between Heliothis 19R clone and SEcR Taq clone

```
HEcR   RPECVVPENQCAMKRKEKKAQREKDKLPVSTTTVDDHMPPIMQCDPPPPEAARILECVQ
SEcR   RPECVVPENQCAMKRKEKKAQREKDKLPVSTTTVDDHMPPIMQCDPPPPEAARI

HEcR   HEVVPRFLNEKLMEQNRLKNVPPLTANQKSLIARLVWYQEGYEQPSEEDLKRVTQSD
SEcR   HEVVPRFLNEKLMERTRLRNVPPLTANQKSLIARLVWYQEGYEQPSEEDLKRVTQSD

HEcR   EDDEDSDMPFRQITEMTILTVQLIVEFAKGLPGFAKISQSDQITLLKACSSEVMMLR
SEcR   EDEEESDMPFRQITEMTILTVQLIVEFAKGLPAFAKISQSDQITLLKACSSEVMMLR

HEcR   VARRYDAATDSVLFANNQAYTRDNYRKAGMAYVIEDLLHFCRCMYSMMMDNVHYALL
SEcR   VARRYDAATDSVLFANNQAYTRDNYRKAGMAYVIEDLLHFCRCMYSMMMDNVHYALL

HEcR   TAIVIFSDRP

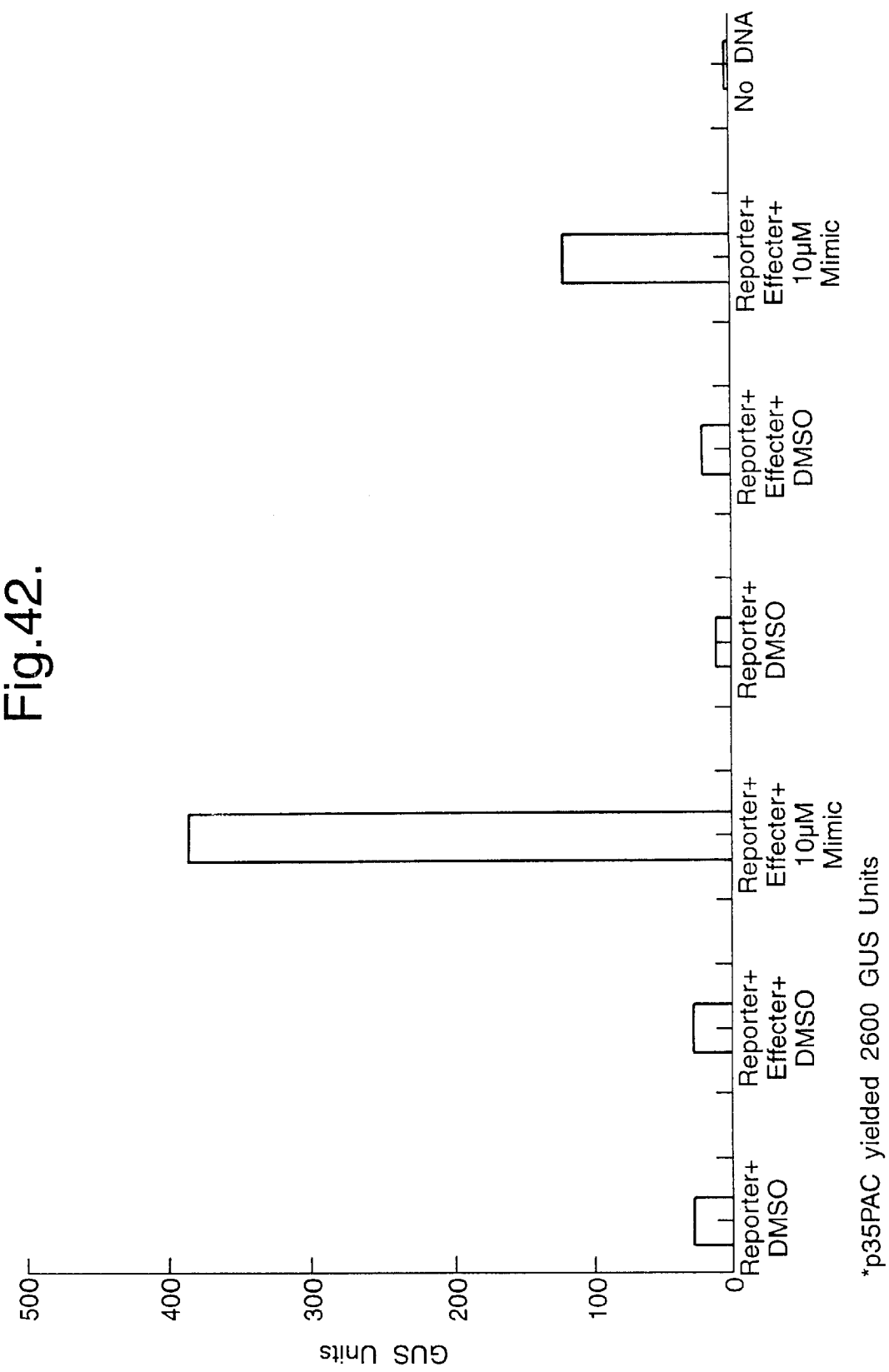

GENE SWITCH

BACKGROUND OF THE INVENTION

The present invention relates to the identification and characterisation of insect steroid receptors from the Lepidoptera species *Heliothis virescens,* and the nucleic acid encoding therefor. The present invention also relates to the use of such receptors, and such nucleic acid, particularly, but not exclusively, in screening methods, and gene switches. By gene switch we mean a gene sequence which is responsive to an applied exogenous chemical inducer enabling external control of expression of the gene controlled by said gene sequence.

Lipophilic hormones such as steroids induce changes in gene expression to elicit profound effects on growth, cellular differentiation, and homeostasis. These hormones recognise intracellular receptors that share a common modular structure consisting of three main functional domains: a variable amino terminal region that contains a transactivation domain, a DNA binding domain, and a ligand binding domain on the carboxyl side of the molecule. The DNA binding domain contains nine invariant cysteines, eight of which are involved in zinc coordination to form a two-finger structure. In the nucleus the hormone-receptor complex binds to specific enhancer-like sequences called hormone response elements (HREs) to modulate transcription of target genes.

The field of insect steroid research has undergone a revolution in the last three years as a result of the cloning and preliminary characterisation of the first steroid receptor member genes. These developments suggest the time is ripe to try to use this knowledge to improve our tools in the constant fight against insect pests. Most of the research carried out on the molecular biology of the steroid receptor superfamily has been on *Drosophila melanogaster* (Diptera), see for example International Patent Publication No WO91/13167, with some in Manduca and Galleria (Lepidoptera).

It has been three decades since 20-hydroxyecdysone was first isolated and shown to be involved in the regulation of development of insects. Since then work has been carried out to try to understand the pathway by which this small hydrophobic molecule regulates a number of activities. By the early 1970s, through the studies of Clever and Ashburner, it was clear that at least in the salivary glands of third instar Drosophila larvae, the application of ecdysone lead to the reproducible activation of over a hundred genes. The ecdysone receptor in this pathway is involved in the regulation of two classes of genes: a small class (early genes) which are induced by the ecdysone receptor and a large class (late genes) which are repressed by the ecdysone receptor. The early class of genes are thought to have two functions reciprocal to those of the ecdysone receptor; the repression of the early transcripts and the induction of late gene transcription. Members of the early genes so far isolated and characterised belong to the class of molecules with characteristics similar to known transcription factors. They are thus predicted to behave as expected by the model of ecdysone action (Ashburner, 1991). More recently, the early genes E74 and E75 have been shown to bind both types of ecdysone inducible genes (Thummel et al., 1990; Segraves and Hogness, 1991), thus supporting their proposed dual activities. It should be noted however, that the activation of a hierarchy of genes is not limited to third instar larvae salivary glands, but that the response to the ecdysone peak at the end of larval life is observed in many other tissues, such as the imaginal disks (i.e. those tissues which metamorphose to adult structures) and other larval tissues which histolyse at the end of larval life (eg. larval fat body). The model for ecdysone action as deduced by studying the third instar chromosome puffing may not apply to the activation of ecdysone regulated genes in adults. In other words, the requirement for other factors in addition to the active ecdysone receptor must be satisfied for correct developmental expression (e.g. the Drosophila yolk protein gene expression in adults is under control of doublesex, the last gene in the sex determination gene hierarchy).

The ecdysone receptor and the early gene E75 belong to the steroid receptor superfamily. Other Drosophila genes, including ultraspiracle, tailless, sevenup and FTZ-FI, also belong to this family. However, of all these genes only the ecdysone receptor is known to have a ligand, and thus the others are known as orphan receptors. Interestingly, despite the ultraspiracle protein ligand binding region sharing 49% identity with the vertebrate retinoic X receptor (RXR) ligand binding region (Oro et al., 1990), they do not share the same ligand (i.e. the RXR ligand is 9-cis retinoic acid) (Heymann et al., 1992 and Mangelsdorf et al., 1992). All the Drosophila genes mentioned are involved in development, ultraspiracle for example, is required for embryonic and larval abdominal development. The protein products of these genes all fit the main features of the steroid receptor superfamily (Evans, 1988; Green and Chambon, 1988, Beato, 1989) i.e. they have a variable N terminus region involved in ligand independent transactivation (Domains A and B), a highly conserved 66–68 amino acid region which is responsible for the binding of DNA at specific sites (Domain C), a hinge region thought to contain a nuclear translocation signal (Domain D), and a well conserved region containing the ligand binding region, transactivation sequences and the dimerisation phase (Domain E). The last region, domain F, is also very variable and its function is unknown.

Steroid receptor action has been elucidated in considerable detail in vertebrate systems at both the cellular and molecular levels. In the absence of ligand, the receptor molecule resides in the cytoplasm where it is bound by Hsp90, Hsp70 and p59 to form the inactive complex (Evans, 1988). Upon binding of the ligand molecule by the receptor a conformational change takes place which releases the Hsp90, Hsp70 and p59 molecules, while exposing the nuclear translocation signals in the receptor. The ligand dependent conformational change is seen in the ligand binding domain of both progesterone and retinoic acid receptors (Allan et al., 1992a). This conformational change has been further characterised in the progesterone receptor and was found to be indispensable for gene transactivation (Allan et al., 1992b). Once inside the nucleus the receptor dimer binds to the receptor responsive element at a specific site on the DNA resulting in the activation or repression of a target gene. The receptor responsive elements usually consist of degenerate direct repeats, with a spacer between 1 and 5 nucleotides, which are bound by a receptor dimer through the DNA binding region (Domain C).

Whereas some steroid hormone receptors are active as homodimers others act as heterodimers. For example, in vertebrates, the retinoic acid receptor (RAR) forms heterodimers with the retinoic X receptor (RXR). RXR can also form heterodimers with the thyroid receptor, vitamin D receptor (Yu et al., 1991; Leid et al., 1992) and peroxisome activator receptor (Kliewer et al., 1992). Functionally the main difference between homodimers and heterodimers is increased specificity of binding to specific response elements. This indicates that different pathways can be linked, co-ordinated and modulated, and more importantly this observation begins to explain the molecular basis of the pleotropic activity of retinoic acid in vertebrate development (Leid et al., 1992b). Similarly, the Drosophila ultraspiracle gene product was recently shown to be capable of forming heterodimers with retinoic acid, thyroid, vitamin D and peroxisome activator receptors and to stimulate the binding of these receptors to their target responsive elements (Yao et al., 1993). More significantly, the ultraspiracle gene product has also been shown to form heterodimers with the ecdysone receptor, resulting in cooperative binding to the ecdysone response element and capable of rendering mammalian cells ecdysone responsive (Yao et al., 1992). The latter is of importance since transactivation of the ecdysone gene alone in mammalian cells fails to elicit an ecdysone response (Koelle et al., 1991), therefore suggesting that the ultraspiracle gene product is an integral component of a functional ecdysone receptor (Yao et al., 1992). It is possible that the ultraspiracle product competes with other steroid receptors or factors to form heterodimers with the ecdysone receptor. Moreover it remains to be investigated if ultraspiracle is expressed in all tissues of the Drosophila larvae. Despite ultraspiracle being necessary to produce a functional ecdysone receptor, the mechanism by which this activation takes place is as yet undetermined.

SUMMARY OF THE INVENTION

We have now isolated and characterised the ecdysone steroid receptor from *Heliothis virescens* (hereinafter HEcR). We have found that surprisingly unlike the Drosophila ecdysone steroid receptor (hereinafter DEcR), in reports to-date, HEcR can be induced by known non-steroidal inducers. It will be appreciated that this provides many advantages for the system.

Steroids are difficult and expensive to make. In addition, the use of a non-steroid as the inducer allows the system to be used in agrochemical and pharmaceutical applications, not least because it avoids application of a steroid which is already present in insects and/or mammals. For example, it would not be feasible to use a gene switch in a mammalian cell which was induced by a naturally occurring steroidal inducer. It will also be appreciated that for environmental reasons it is advantageous to avoid the use of steroids as inducers.

According to one aspect of the present invention there is provided DNA having the sequence shown in SEQ ID NO: 2, wherein SEQ ID NO: 2 gives the sequence for the HEcR.

According to another aspect of the present invention there is provided DNA having part of the sequence shown in SEQ ID NO: 2, which encodes for the HEcR ligand binding domain.

According to another aspect of the present invention there is provided DNA having part of the sequence shown in SEQ ID NO: 2, which encodes for the HEcR DNA binding domain.

According to yet another aspect of the present invention there is provided DNA having part of the sequence shown in SEQ ID NO: 2, which encodes for the HEcR transactivation domain.

According to a further aspect of the present invention there is provided DNA having part of the sequence shown in SEQ ID NO: 2, which encodes for the HEcR hinge domain.

According to a still further aspect of the present invention there is provided DNA having part of the sequence shown in SEQ ID NO: 2, which encodes for the HEcR carboxy terminal region.

According to one aspect of the present invention there is provided DNA having the sequence shown in SEQ ID NO: 3, wherein SEQ ID NO: 3 gives the sequence for the HEcR.

According to another aspect of the present invention there is provided DNA having part of the sequence shown in SEQ ID NO: 3, which encodes for the HEcR ligand binding domain.

According to another aspect of the present invention there is provided DNA having part of the sequence shown in SEQ ID NO: 3, which encodes for the HEcR DNA binding domain.

According to yet another aspect of the present invention there is provided DNA having part of the sequence shown in SEQ ID NO: 3, which encodes for the HEcR transactivation domain.

According to a further aspect of the present invention there is provided DNA having part of the sequence shown in SEQ ID NO: 3, which encodes for the HEcR hinge domain.

According to a still further aspect of the present invention there is provided DNA having part of the sequence shown in SEQ ID NO: 3, which encodes for the HEcR carboxy terminal region.

According to one aspect of the present invention there is provided DNA having the sequence shown in SEQ ID NO: 4, wherein SEQ ID NO: 4 gives the sequence for the HEcR.

According to another aspect of the present invention there is provided DNA having part of the sequence shown in SEQ ID NO: 4, which encodes for the HEcR ligand binding domain.

According to another aspect of the present invention there is provided DNA having part of the sequence shown in SEQ ID NO: 4, which encodes for the HEcR DNA binding domain.

According to yet another aspect of the present invention there is provided DNA having part of the sequence shown in SEQ ID NO: 4, which encodes for the HEcR transactivation domain.

According to a further aspect of the present invention there is provided DNA having part of the sequence shown in SEQ ID NO: 4, which encodes for the HEcR hinge domain.

According to a still further aspect of the present invention there is provided DNA having part of the sequence shown in SEQ ID NO: 4, which encodes for the HEcR carboxy terminal region.

DETAILED DESCRIPTION OF THE INVENTION

As mentioned above, steroid receptors are eukaryotic transcriptional regulatory factors which, in response to the binding of the steroid hormone, are believed to bind to specific DNA elements and activate transcription. The steroid receptor can be divided into six regions, designated A to F, using alignment techniques based on shared homology with other members of the steroid hormone receptor superfamily. Krust et al identified two main regions in the receptor, C and E. Region C is hydrophilic and is unusual in its high content in cysteine, lysine and arginine. It corresponds to a DNA-binding domain, sometimes referred to as the "zinc finger". It is the DNA binding domain which binds to the upstream DNA of the responsive gene. Such upstream DNA is known as the hormone response element or HRE for short. Region E is hydrophobic and is identified as the hormone (or ligand) binding domain. Region E can be further subdivided into regions E1, E2 and E3.

The region D, which separates domains C and E is highly hydrophobic and is flexible. It is believe that communication between domains E and C involves direct contact between them through region D, which provides a hinge between the two domains. Region D is therefore referred to as the hinge domain.

The mechanism of the receptor appears to require it to interact with some element(s) of the transcription machinery over and above its interactions with the hormone and the hormone response element. N-terminal regions A and B perform such a function and are jointly known as the transactivation domain. The carboxy terminal region is designated F.

The domain boundaries of the HEcR can be defined as follows:

| DOMAIN | INTERVALS | |
| --- | --- | --- |
| | base pairs | amino acids |
| Transactivating (A/B) | 114–600 | 1–162 |
| DNA Binding (C) | 601–798 | 163–228 |
| Hinge (D) | 799–1091 | 229–326 |
| Ligand Binding (E) | 1092–1757 | 327–545 |
| C-Terminal End | 1758–1844 | 546–577 |

The DNA binding domain is very well defined and is 66 amino acids long, thus providing good boundaries. The above intervals have been defined using the multiple alignment for the ecdysone receptors (FIG. 5).

The present invention also includes DNA which shows homology to the sequences of the present invention. Typically homology is shown when 60% or more of the nucleotides are common, more typically 65%, preferably 70%, more preferably 75%, even more preferably 80% or 85%, especially preferred are 90%, 95%, 98% or 99% or more homology.

The present invention also includes DNA which hybridises to the DNA of the present invention and which codes for at least part of the Heliothis ecdysone receptor transactivation domain, DNA binding domain, hinge domain, ligand binding domain and/or carboxy terminal region. Preferably such hybridisation occurs at, or between, low and high stringency conditions. In general terms, low stringency conditions can be defined as 3×SCC at about ambient temperature to about 65° C., and high stringency conditions as 0.1×SSC at about 65° C. SSC is the name of a buffer of 0.15M NaCl, 0.015M trisodium citrate. 3×SSC is three time as strong as SSC and so on.

The present invention further includes DNA which is degenerate as a result of the genetic code to the DNA of the present invention and which codes for a polypeptide which is at least part of the Heliothis ecdysone receptor transactivation domain, DNA binding domain, hinge domain, ligand binding domain and/or carboxy terminal region.

The DNA of the present invention may be cDNA or DNA which is in an isolated form.

According to another aspect of the present invention there is provided a polypeptide comprising the Heliothis ecdysone receptor or a fragment thereof, wherein said polypeptide is substantially free from other proteins with which it is ordinarily associated, and which is coded for by any of the DNA of the present invention.

According to another aspect of the present invention there is provided a polypeptide which has the amino acid sequence of SEQ ID NO: 4 or any allelic variant or derivative thereof, wherein SEQ ID No. 4 gives the amino acid sequence of the HEcR polypeptide.

According to another aspect of the present invention there is provided a polypeptide which has part of the amino acid sequence of SEQ ID No. 4 or any allelic variant or derivative thereof, which sequence provides the HEcR ligand binding domain.

According to another aspect of the present invention there is provided a polypeptide which has part of the amino acid sequence of SEQ ID No. 4 or any allelic variant or derivative thereof, which sequence provides the HEcR DNA binding domain.

According to yet another aspect of the present invention there is provided a polypeptide which has part of the amino acid sequence of SEQ ID No. 4 or any allelic variant or derivative thereof, which sequence provides the HEcR transactivation domain.

According to a further aspect of the present invention there is provided a polypeptide which has the amino acid sequence of a part of SEQ ID No. 4 or any allelic variant or derivative thereof, which sequence provides the HEcR hinge domain.

According to a still further aspect of the present invention there is provided a polypeptide which has the amino acid sequence of a part of SEQ ID No. 4 or any allelic variant or derivative thereof, which sequence provides the HEcR carboxy terminal region.

For the avoidance of doubt, spliced variants of the amino acid sequences of the present invention are included in the present invention.

Preferably, said derivative is a homologous variant which has conservative amino acid changes. By conservation amino acid changes we mean replacing an amino acid from one of the amino acid groups, namely hydrophobic, polar, acidic or basic, with an amino acid from within the same group. An examples of such a change is the replacement of valine by methionine and vice versa.

According to another aspect of the present invention there is provided a fusion polypeptide comprising at least one of the polypeptides of the present invention functionally linked to an appropriate non-Heliothis ecdysone receptor domain (s).

According to an especially preferred embodiment of the present invention the HEcR ligand binding domain of the present invention is fused to a DNA binding domain and a transactivation domain.

According to another embodiment of the present invention the DNA binding domain is fused to a ligand binding domain and a transactivation domain.

According to yet another embodiment of the present invention the transactivation domain is fused to a ligand binding domain and a DNA binding domain.

The present invention also provides recombinant DNA encoding for these fused polypeptides.

According to an especially preferred embodiment of the present invention there is provided recombinant nucleic acid comprising a DNA sequence encoding the HEcR ligand binding domain functionally linked to DNA encoding the DNA binding domain and transactivation domain from a glucocorticoid receptor.

According to yet another aspect of the present invention there is provided recombinant nucleic acid comprising a DNA sequence comprising a reporter gene operably linked to a promoter sequence and a hormone response element which hormone response element is responsive to the DNA bonding domain encoded by the DNA of of the present invention.

According to another aspect of the present invention there is provided a construct transformed with nucleic acid, recombinant DNA, a polypeptide or a fusion polypeptide of the present invention. Such constructs include plasmids and phages suitable for transforming a cell of interest. Such constructs will be well known to those skilled in the art.

According to another aspect of the present invention there is provided a cell transformed with nucleic acid, recombinant DNA, a polypeptide, or a fusion polypeptide of the present invention.

Preferably the cell is a plant, fungus or mammalian cell.

For the avoidance of doubt fungus includes yeast.

The present invention therefore provides a gene switch which is operably linked to a foreign gene or a series of foreign genes whereby expression of said foreign gene or said series of foreign genes may be controlled by application of an effective exogenous inducer.

Analogs of ecdysone, such as Muristerone A, are found in plants and disrupt the development of insects. It is therefore proposed that the receptor of the present invention can be used be in plants transformed therewith as an insect control mechanism. The production of the insect-damaging product being controlled by an exogenous inducer. The insect-damagin g product can be ecdysone or another suitable protein.

The first non-steroidal ecdysteroid agonists, dibenzoyl hydrazines, typified by RH-5849 [1,2-dibenzoyl, 1-tert-butyl hydrazide], which is commercially available as an insecticide from Rohm and Haas, were described back in 1988. Another commercially available compound in this series is RH-5992 [tebufenozide, 3,5-dimethylbenzoic acid 1-1 (1,1-dimethylethyl)-2(4-ethylbenzoyl) hydrazide]. These compounds mimic 20-hydroxyecdysone (20E) in both *Manduca sexta* and *Drosophila melanogaster.* These compounds have the advantage that they have the potential to control insects using ecdysteroid agonists which are non-steroidal. Further Examples of such dibenzoyl hydrazines are given in U.S. Pat. No. 5,117,057 to Rohm and Haas, and Oikawa et al, Pestic Sci, 41, 139–148 (1994). However, it will be appreciated that any inducer of the gene switch of the present invention, whether steroidal or non-steroidal, and which is currently or becomes available, may be used.

The gene switch of the present invention, then, when linked to an exogenous or foreign gene and introduced into a plant by transformation, provides a means for the external regulation of expression of that foreign gene. The method employed for transformation of the plant cells is not especially germane to this invention and any method suitable for the target plant may be employed. Transgenic plants are obtained by regeneration from the transformed cells. Numerous transformation procedures are known from the literature such as agroinfection using *Agrobacterium tumefaciens* or its Ti plasmid, electroporation, microinjection or plants cells and protoplasts, microprojectile transformation, to mention but a few. Reference may be made to the literature for full details of the known methods.

Neither is the plant species into which the chemically inducible sequence is inserted particularly germane to the invention. Dicotyledonous and monocotyledonous plants can be transformed. This invention may be applied to any plant for which transformation techniques are, or become, available. The present invention can therefore be used to control gene expression in a variety of genetically modified plants, including field crops such as canola, sunflower, tobacco, sugarbeet, and cotton; cereals such as wheat, barley, rice, maize, and sorghum; fruit such as tomatoes, mangoes, peaches, apples, pears, strawberries, bananas and melons; and vegetables such as carrot, lettuce, cabbage and onion. The switch is also suitable for use in a variety of tissues, including roots, leaves, stems and reproductive tissues.

In a particularly preferred embodiment of the present invention, the gene switch of the present invention is used to control expression of genes which confer resistance herbicide resistance and/or insect tolerance to plants.

Recent advances in plant biotechnology have resulted in the generation of transgenic plants resistant to herbicide application, and transgenic plants resistant to insects. Herbicide tolerance has been achieved using a range of different transgenic strategies. One well documented example in the herbicide field is the use the bacterial xenobiotic detoxifying gene phosphinothricin acetyl transferase (PAT) from *Streptomyces hydroscopicus*. Mutated genes of plant origin, for example the altered target site gene encoding acetolactate synthase (ALS) from Arabidopsis, have been successfully utilised to generate transgenic plants resistant to herbicide application. The PAT and ALS genes have been expressed under the control of strong constitutive promoter. In the field of insecticides, the most common example to-date is the use of the Bt gene.

We propose a system where genes conferring herbicide and/or insect tolerance would be expressed in an inducible manner dependent upon application of a specific activating chemical. This approach has a number of benefits for the farmer, including the following:

1. Inducible control of herbicide and/or insect tolerance would alleviate any risk of yield penalties associated with high levels of constitutive expression of herbicide and/or insect resistance genes. This may be a particular problem as early stages of growth where high levels of transgene product may directly interfere with normal development. Alternatively high levels of expression of herbicide and/or insect resistance genes may cause a metabolic drain for plant resources.
2. The expression of herbicide resistance genes in an inducible manner allows the herbicide in question to be used to control volunteers if the activating chemical is omitted during treatment.
3. The use of an inducible promoter to drive herbicide and/or insect resistance genes will reduce the risk of resistance becoming a major problem. If resistance genes were passed onto weed species from related crops, control could still be achieved with the herbicide in the absence of inducing chemical. This would particularly be relevant if the tolerance gene confirmed resistance to a total vegetative control herbicide which would be used (with no inducing chemical) prior to sowing the crop and potentially after the crop has been harvested. For example, it can be envisaged that herbicide resistance cereals, such as wheat, might outcross into the weed wild oats, thus conferring herbicide resistance to this already troublesome weed. A further example is that the inducible expression of herbicide resistance in sugar beet will reduce the risk of wild sugar beet becoming a problem. Similarly, in the field of insect control, insect resistance may well become a problem if the tolerance gene is constitutively expressed. The used of an inducible promoter will allow a greater range of insect resistance control mechanisms to be employed.

This strategy of inducible expression of herbicide resistance can be achieved with a pre-spray of chemical activator or in the case of slow acting herbicides, for example N-phosphonomethyl-glycine (commonly known as glyphosate), the chemical inducer can be added as a tank mix simultaneously with the herbicide. Similar strategies can be employed for insect control.

This strategy can be adopted for any resistance confering gene/corresponding herbicide combination, which is, or becomes, available. For example, the gene switch of the present invention can be used with:

1. Maize glutathione S-transferase (GST-27) gene (see our International Patent Publication No WO90/08826), which confers resistance to chloroacetanilide herbicides such as acetochlor, metolachlor and alachlor.
2. Phosphinotricin acetyl transferase (PAT), which confers resistance to the herbicide commonly known as glufosinate.
3. Acetolactate synthase gene mutants from maize (see our International Patent Publication No WO90/14000) and other genes, which confer resistance to sulphonyl urea and imadazolinones.
4. Genes which confer resistance to glyphosate. Such genes include the glyphosate oxidoreductase gene (GOX) (see International Patent Publication No. WO92/00377); genes which encode for 5-enolpyruvyl-3-phosphoshikimic acid synthase (EPSPS), including Class I and Class II EPSPS, genes which encode for mutant EPSPS, and genes which encode for EPSPS fusion peptides such as that comprised of a chloroplast transit peptide and EPSPS (see for example EP 218 571, EP 293 358, WO91/04323, WO92/04449 and WO92106201); and genes which are involved in the expression of CPLyase.

Similarly, the strategy of inducible expression of insect resistance can be adopted for any tolerance confering gene which is, or becomes, available.

The gene switch of the present invention can also be used to controlled expression of foreign proteins in yeast and mammalian cells. Many heterologous proteins for many applications are produced by expression in genetically engineered bacteria, yeast cells and other eucaryotic cells such as mammalian cells.

As well as the obvious advantage in providing control over the expression of foreign genes in such cells, the switch of the present invention provides a further advantage in yeasts and mammalian cells where accumulation of large quantities of an heterologous protein can damage the cells, or where the heterologous protein is damaging such that expression for short periods of time is required in order to maintain the viability of the cells.

Such an inducible system also has applicability in gene therapy allowing the timing of expression of the therapeutic gene to be controlled. The present invention is therefore not only applicable to transformed mammalian cells but also to mammals per se.

A further advantage of the inducible system of the present invention in mammalian cells is that, because it is derived from a insect, there is less chance of it being effected by inducers which effect the natural mammalian steroid receptors.

In another aspect of the present invention the gene switch is used to switch on genes which produce potentially damaging or lethal proteins. Such a system can be employed in the treatment of cancer in which cells are transformed with genes which express proteins which are lethal to the cancer. The timing of the action of such proteins on the cancer cells can be controlled using the switch of the present invention.

The gene switch of the present invention can also be used to switch genes off as well as on. This is useful in disease models. In such a model the cell is allowed to grow before a specific gene(s) is switched off using the present invention. Such a model facilitates the study of the effect of a specific gene(s).

Again the method for producing such transgenic cells is not particularly germane to the present invention and any method suitable for the target cell may be used; such methods are known in the art, including cell specific transformation.

As previously mentioned, modulation of gene expression in the system appears in response to the binding of the HEcR to a specific control, or regulatory, DNA element. A schematic representation of the HEcR gene switch is shown in FIG. 6. For ease of reference, the schematic representation only shows three main domains of the HEcR, namely the transactivation domain, DNA binding domain and the ligand binding domain. Binding of a ligand to the ligand binding domain enables the DNA binding domain to bind to the HRE resulting in expression (or indeed repression) of a target gene.

The gene switch of the present invention can therefore be seen as having two components. The first component comprising the HEcR and a second component comprising an appropriate HRE and the target gene. In practice, the switch may conveniently take the form of one or two sequences of DNA. At least part of the one sequence, or one sequence of the pair, encoding the HEcR protein. Alternatively, the nucleic acid encoding the HEcR can be replaced by the protein/polypeptide itself.

Not only does the switch of the present invention have two components, but also one or more of the domains of the receptor can be varied producing a chimeric gene switch. The switch of the present invention is very flexible and different combinations can be used in order to vary the result/to optimise the system. The only requirement in such chimeric systems is that the DNA binding domain should bind to the hormone response element in order to produce the desired effect.

The glucocorticoid steroid receptor is well characterised and has been found to work well in plants. A further advantage of this receptor is that it functions as a homodimer. This means that there is no need to express a second protein such as the ultraspiracle in order to produce a functional receptor. The problem with the glucocorticoid steroid receptor is that ligands used to activate it are not compatible with agronomic practice.

In a preferred aspect of the present invention the receptor comprises glucocorticoid receptor DNA binding and transactivation domains with a Heliothis ligand binding domain according to the present invention. The response unit preferably comprising the glucocorticoid hormone response element and the desired effect gene. In the Examples, for convenience, this effect gene took the form of a reporter gene. However, in non-test or non-screen situations the gene will be the gene which produces the desired effect, for example produces the desired protein. This protein may be a natural or exogenous protein. It will be appreciated that this chimeric switch combines the best features of the glucocorticoid system, whilst overcoming the disadvantage of only being inducible by a steroid.

In another preferred embodiment, the Heliothis ligand binding domain is changed, and preferably replaced with a non-Heliothis ecdysone receptor ligand binding domain. For example, we have isolated suitable sequences from *Spodoptera exigua*.

Thus, according to another aspect of the present invention there is provided DNA having the sequence shown in SEQ ID NO: 6.

According to another aspect of the present invention there is provided DNA having part of the sequence shown in SEQ ID NO: 6, which encodes for the Spodoptera ecdysone ligand binding domain.

According to another aspect of the present invention there is provided DNA having part of the sequence shown in SEQ ID NO: 6, which encodes for the Spodoptera ecdysone hinge domain.

The present invention also provides the polypeptides coded for by the above DNA sequences of SEQ ID NO: 6.

A further advantage with such chimeric systems is that they allow you to choose the promoter which is used to drive the effector gene according to the desired end result. For example, placing the foreign gene under the control of a cell specific promoter can be particularly advantageous in circumstances where you wish to control not only the timing of expression, but also which cells expression occurs in. Such a double control can be particularly important in the areas of gene therapy and the use of cytotoxic proteins.

Changing the promoter also enables gene expression to be up- or down-regulated as desired.

Any convenient promoter can be used in the present invention, and many are known in the art.

Any convenient transactivation domain may also be used. The transactivation domain VP16 is a strong activator from Genentech Inc., and is commonly used when expressing glucocorticoid receptor in plants. Other transactivation domains derived for example from plants or yeast may be employed.

In a preferred embodiment of the present invention, the DNA binding domain is the glucocorticoid DNA binding domain. This domain is commonly a human glucocorticoid receptor DNA binding domain. However, the domain can be obtained from any other convenient source, for example, rats.

According to another aspect of the present invention there is provided a method of selecting compounds capable of being bound to an insect steroid receptor superfamily member comprising screening compounds for binding to a polypeptide or fusion polypeptide of the present invention, and selecting said compounds exhibiting said binding.

According to another aspect of the present invention there is provided a compound selected using the method of the present invention.

According to another aspect of the present invention there is provided an agricultural or pharmaceutical composition comprising the compound of the present invention.

According to yet another aspect of the present invention there is provided the use of the compound of the present invention as a pesticide, pharmaceutical and/or inducer of the switch. It will be appreciated that such inducers may well be useful as insecticides in themselves.

According to a further aspect of the present invention there is provided a method of producing a protein or peptide or polypeptide comprising introducing into a cell of the present invention, a compound which binds to the ligand binding domain in said cell.

Various preferred features and embodiments of the present invention will now be described by way of non-limiting example with reference to the accompanying examples and figures, in which figures:

BRIEF DESCRIPTION OF THE DRAWINGS

FIG. 1 shows the DNA sequence amplified from first strand cDNA made from RNA isolated from *Heliothis virescens* Fourth instar larvae. The upper sequence SEQ ID NO: 1. The lower sequence is the complementary sequence SEQ ID NO: 8. The underlined sequences refer to the position of the degenerate oligonucleotides. At the 5' end the sequence matches that of the oligonucleotide while at the 3' end 12 nucleotides of the original oligonucleotide are observed;

FIG. 2 shows the DNA sequence contained within the clone pSK19R (SEQ ID NO: 2 isolated from a random primed cDNA *Heliothis virescens* library; Sequence is flanked by EcoRI sites lower sequence is the complementary sequence SEQ ID NO: 9;

FIG. 3 shows the DNA sequence contained within the clone pSK16.1 (SEQ ID NO: 3) isolated from a random primed cDNA *Heliothis virescens* library lower sequence is the complementary sequence SEQ ID NO: 9;

FIG. 4 (Sequence ID No. 4) DNA sequence of 5' RACE products (in bold) fused to sequence of clone pSK16.1. The ORF (open reading frame) giving rise to the *Heliothis virescens* ecdysone receptor protein sequence is shown under the corresponding DNA sequence;

FIG. 5 (Sequence ID No. 5) shows the protein sequence alignment of the ecdysone receptors DmEcR (*Drosophila melanogaster*), (SEQ ID NO: 15), CtEcR (*Chironomus tentans*) (SEQ ID NO: 13), BmEcR (*Bombyx mori*) (SEQ ID NO: 11), MsEcR (*Manduca Sexta*) (SEQ ID NO: 12), AaEcR (*Aedes aegipti*) (SEQ ID NO: 14) and HvEcR (*Heliothis virescens*)(SEQ ID NO: 5). "*" indicates conserved amino acid residue. "." indicates a conservative amino acid exchange;

FIG. 40 shows the DNA sequence of the hinge and ligand binding domains of the *Spodoptera exigua* ecdysone receptor (SEQ ID NO: 6) the complementary sequence is SEQ ID NO: 64;

FIG. 41 shows the protein sequence alignment of the Heliothis 19R (SEQ ID NO: 7) and Spodoptera SecR taq clone (SEQ ID NO: 16) hinge and ligand binding domains. "*" indicates conserved amino acid residue. "." indicates a conservative amino acid exchange;

FIG. 42 shows a graph which shows the effect of RH5992 on Tobacco mesophyll protoplasts transformed with pMF7GRHEcR (effector) and either p221.9GRE6 (Horizontal strips) or p221.10GRE6 (vertical strips).

EXAMPLE I

Cloning of the Heliothis Ecdysone Receptor

A. Probe Generation

Figure 6:
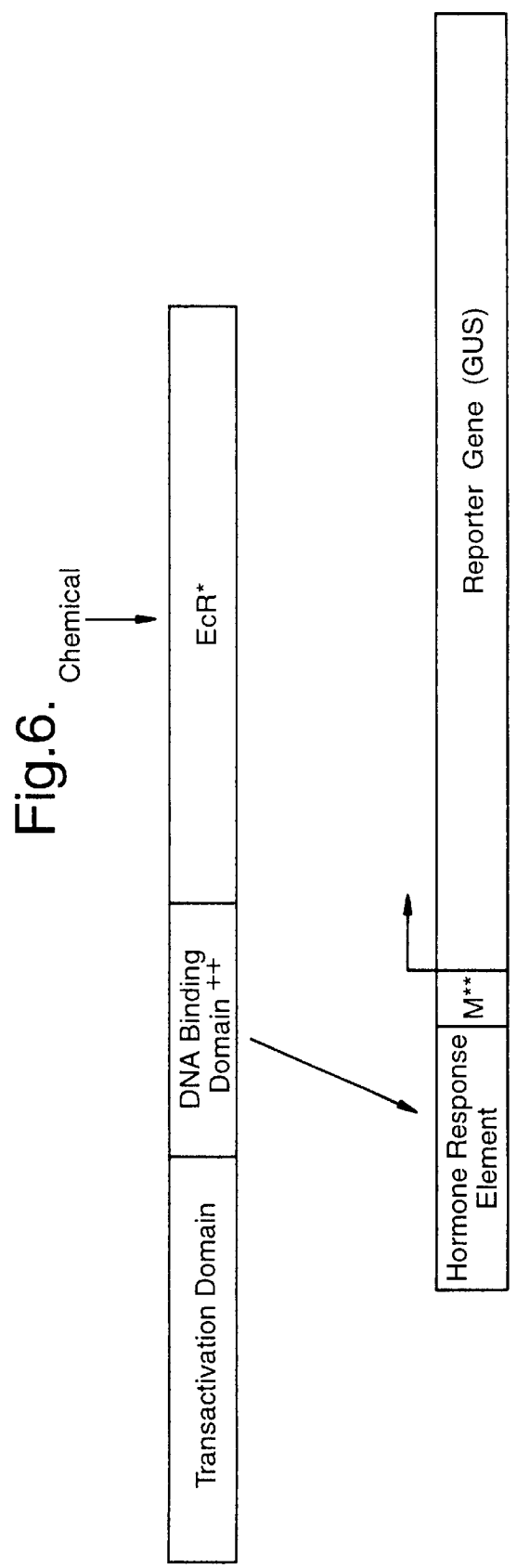
FIG. 6 shows a model of an embodiment of the glucocorticoid/Heliothis ecdysone chimeric receptor useable as a gene switch.

The rational behind the generation of the probe to isolate Heliothis homologues to the steroid/thyroid receptor superfamily members was based on comparing the sequences of developmentally regulated steroid/thyroid receptor superfamily members. The sequences available showed a highly conserved motif within the DNA binding domain of the RAR and THR (thyroid) receptors. The motifs were used to design degenerate oligonucleotides for PCR amplification of sequences derived from cDNA template produced from tissue expected to express developmentally regulated steroid/thyroid receptor superfamily members (ie. larval tissues).

The sense oligonucleotide is based on the peptide sequence CEGCKGFF (SEQ ID NO: 17) which at the DNA level yields an oligonucletide with degeneracy of 32 as shown below:

```
ZnFA5' 5' TGC.GAG GGI TGC AAG GAI TTC TT 3'  (SEQ ID NO:18)
          T   A       T   A       T
```

The antisense oligonucleotide is based on the reverse complement nucleotide sequence derived from the peptide:

```
CQECRLKK  (SEQ ID NO:19)
 S   R
``` for which four sets of degenerate oligos were made. Namely:

```
ZnFA3' 5' TTC TTI AGI CGG CAC TCT TGG CA 3'  (SEQ ID NO:20)
          T       A   T   C   A
```

```
-continued
ZnFB3'  5'  TTC  TTI  AAI  CGG  CAC  TCT  TGG  CA 3'  (SEQ ID NO:21)
            T         A    T    C    A ZnFC3'  5'  TTC  TTI  AGI  CTG  CAC  TCT  TGG  CA 3'  (SEQ ID NO:22)
            T         A    T    C    A ZnFD3'  5'  TTC  TTI  AAI  CTG  CAC  TCT  TGG  CA 3'  (SEQ ID NO:23)
            T         A    T    C    A
```

The PCR amplification was carried out using a randomly primed cDNA library made from mRNA isolated from 4th and 5th instar *Heliothis virescens* larvae. The amplification was performed using $10^8$ pfus (plaque forming units) in 50 mM KCl. 20 mM Tris HCl pH 8.4, 15 mM MgCl2, 200 mM dNTPs (an equimolar mixture of dCTP, dATP, dGTP and dTTP), 100 ng of ZnFA5' and ZnF3' mixture. The conditions used in the reaction followed the hot start protocol whereby the reaction mixture was heated to 94° C. for 5 minutes after which 1 U of Taq polymerase was added and the reaction allowed to continue for 35 cycles of 93° C. for 50 seconds, 40° C. for 1 minute and 73° C. for 1 minute 30 seconds. The PCR products were fractionated on a 2%(w/v) agarose gel and the fragment migrating between 100 and 200 bp markers was isolated and subcloned into the vector pCRII (Invitrogen). The sequence of the insert was determined using Sequenase (USB).

The resulting sequence was translated and a database search carried out. The search recovered sequences matching to the DNA binding domain of the Drosophila ecdysone receptor, retinoic acid receptor and the thyroid receptor. Thus, the sequence of the insert in this plasmid, designated pCRIIZnf, is a Heliothis ecdysone cognate sequence (FIG. 1) and was used to screen a cDNA library in other to isolate the complete open reading frame.

B. Library Screening

The randomly primed cDNA 4th/5th Instar *Heliothis virescens* library was plated and replicate filter made from the plates. The number of plaques plated was 500,000. The insert fragment of pCRIIZnf was reamplified and 50 ng were end labelled using T4 Polynucleotide Kinase (as described in Sambrook et al 1990).

The filter were prehybridised using 0.25%(w/v) Marvel, 5×SSPE and 0.1%(w/v) SDS at 42° C. for 4 hours. The solution in the filters was ten replaced with fresh solution and the denatured probe added. The hybridisation was carried out overnight at 42° C. after which the filter were washed in 6×SSC+0.1%(w/v) SDS at 42° C. followed by another wash at 55° C. The filter were exposed to X-ray film (Kodak) for 48 hours before processing.

The developed film indicated the presence of one strong positive signal which was plaque purified and further characterised. The lambda ZAP II phage was in vivo excised (see Stratagene Manual) and the sequence determined of the resulting plasmid DNA. The clone known as pSK19R (or 19R) contained a 1.933 kb cDNA fragment with an open reading frame of 467 amino acids (FIG. 2). pSK19R was deposited with the NCIMB on Jun. 20, 1995 and has been accorded the deposit No NCIMB 40743.

Further analysis of pSK19R revealed that a 340 bp EcoRI fragment mapping at the 5' end of pSK19R has strong and significant similarities to a Drosophila cDNA encoding glyceraldehyde-3-phosphate dehydrogenase. In order to isolate the correct 5' end sequence belonging to Heliothis, the random primed library was re-screened using a probe containing the 5' end of the pSK19R belonging to Heliothis ecdysone receptor. The probe was made by PCR using the sense oligonucleotide HecRH3C (5' aattaagcttccaccatgccgt-taccaatgccaccgaca 3' (SEQ ID NO: 24) and antisense oligonucleotide HecrNdeI (5' ctcaaccgacactcctgac 3' (SEQ ID NO: 25)). The PCR was carried out as described by Hirst et al., 1992) where the amount of radioisotope used in the labelling was 50 uCi of a $^{32}$P-dCTP and the PCR was cycled for 1 minute at 94° C., 1 minute at 60° C. and 1 minute at 72° C. for 19 cycles. The resulting 353 bp radio labelled DNA fragment was denatured and added to prehybridised filters as described for the isolation of pSK19R. The library filters were made from 15 plates each containing 50000 pfus. The library filters were hybridised at 65° C. and washed in 3×SSPE+0.1%SDS at 65° C. twice for 30 minutes each. The filters were further washed with 1×SSPE+0.1%SDS for 30 minutes and exposed to X-ray film (Kodak) overnight. The film was developed and 16 putative positive plaques were picked. The plaques were re-plated and hybridised under the exact same conditions as the primary screen resulting in only one strong positive. The strong positive was consistently recognised by the probe and was plaque purified and in vivo excised. The resulting plasmid pSK16.1 was sequenced (Seq 1D3) which revealed that the 5' end of the clone extended by 205 bp and at the 3' end by 653 bp and resulting in a DNA insert of 2.5 kb. Conceptual translation of the 205 bp yielded 73 amino acids with high similarity to the Drosophila, *Aedes aegipti*, Manduca and Bombyx sequences of the ecdsysone receptor B1 isoform. However, the whole of the 5' end sequence is not complete since a Methionine start site was not found with a stop codon in frame 5' of the methionine. In order to isolate the remainder of the 5' end coding sequences a 5'RACE protocol (Rapid Amplification of cDNA Ends) was carried out using the BRL-GIBCO 5'RACE Kit. Two types of cDNA were synthesised where the first one used a specific oligonucleotide: 16PCR2A 5' cagctccaggccgccgatctcg3' (SEQ ID NO: 26) and the second type used random hexamers (oligonucleotide containing 6 random nucleotides). Each cDNA was PCR amplified using the oligonucleotides anchor primer: BRL-GIBCO 5' cuacuacuacuaggccacgcgtcgactagtacgggiigggiigggiig 3' (SEQ ID NO: 27) and 16PCR2A and cycled for 1 minute at 94° C., 1 minute at 60° C. and 1 minute at 72° C. for 35 cycles. The reaction conditions were 20 mM Tris-HCl (pH8.4), 50 mM KCl, 1.5 mM MgCl$_2$, 400 nM of each anchor and 16PCR2A primers, 200 mM dNTPs (dATP,dCTP,dGTP and dTTP) and 0.02 U/ml Taq DNA polymerase. Dilutions of 1:50 of the first PCR reactions were made and 1 ml was use in a second PCR with oligonucleotides UAP: (Universal Amplification Primer 5' caucaucaucauggccacgcgtcgactagtac 3') (SEQ ID NO: 28) and 16RACE2: (5'acgtcacctcagacgagctctccattc 3') (SEQ ID NO: 29).

The conditions and cycling were the same as those followed for the first PCR. Samples of each PCR were run and a Southern blot carried out which was probed with a 5' specific primer: (16PCR1 5' cgctggtataacaacggaccattc 3') (SEQ ID NO: 30).

This primer is specific for the 5' most sequence of pSK16.1 and was hybridised at 55° C. using the standard hybridisation buffer. The filter was washed at 55° C. 3 times in 3×SSPE+0.1%SDS and exposed to X-ray film for up to 6 hours. The developed film revealed bands recognised by the oligonucleotide migrating at 100 bp and 500 bp (relative to the markers). A sample of the PCR reaction (4 in total) was cloned into the pCRII vector in the TA cloning kit (Invitrogen). Analysis of 15 clones from 4 independent PCRs yielded sequence upsteam of pSK16.1 (FIG. 4).

Translation of the ORF results in a 575 amino acid protein with high similarity in the DNA and ligand binding domains when compared to the ecdysone receptor sequences of Drosophila, *Aedes aegypti, Chironomus tentans, Manduca sexta* and *Bombyx mori* (FIG. 5). Interestingly, the N-terminal end of the Heliothis sequence has an in frame methinonine start which is 20 amino acids longer that that reported for Drosophila, *Aedes aegypti* and *Manduca sexta*. However, the extended N-terminal end in the Heliothis EcR does not have similarity to that of *Bombyx mori*. Finally, the C-terminal end of the different B1 isoform ecdysone receptor sequences diverge and do not have significant similarity.

C. Northern Blot Analysis

The sequence identified by screening the library is expected to be expressed in tissues undergoing developmental changes, thus mRNA from different developmental stages of H. virescens were was isolated and a northen blot produced. The mRNAs were isolated from eggs, 1st, 2nd, 3rd, 4th and 5th instar larvae, pupae and adults. The northern blot was hybridised with a NdeI/XhoI DNA fragment from pSK19R encompassing the 3'end of the DNA binding domain through to the end of the ligand binding domain. The hybridisation was carried out in 1%(w/v)Marvel, 5×SSPE, 0.1%(w/v) SDS at 65° C. for 18 to 24 hours. The filters were washed in 3×SSPE+0.1%(w/v) SDS and 1×SSPE+0.1%(w/v) SDS at 65° C. The filter was blotted dry and exposed for one to seven days. The gene recognises two transcripts (6.0 and 6.5 kb) which appear to be expressed in all stages examined, however, the levels of expression differ in different stages. It should be noted that the same two transcripts are recognised by probes specific to the DNA binding domain and the ligand binding domain, indicating that the two transcripts arise from the same gene either by alternative splicing or alternative use of polyadenylation sites.

In summary, adult and 5th instar larvae have lower levels of expression while all other tissues have subtantial levels of expression.

EXAMPLE II

Expression of Heliothis Ecdysone Receptor in Mammalian Cells

To demonstrate that the cDNA encodes a functional ecdysone receptor, effector constructs were generated containing the HEcR under the control of the CMV (cytomegalovirus) promoter, and the DNA expressed in mammalian cells.

Effector Constructs

Figure 7:
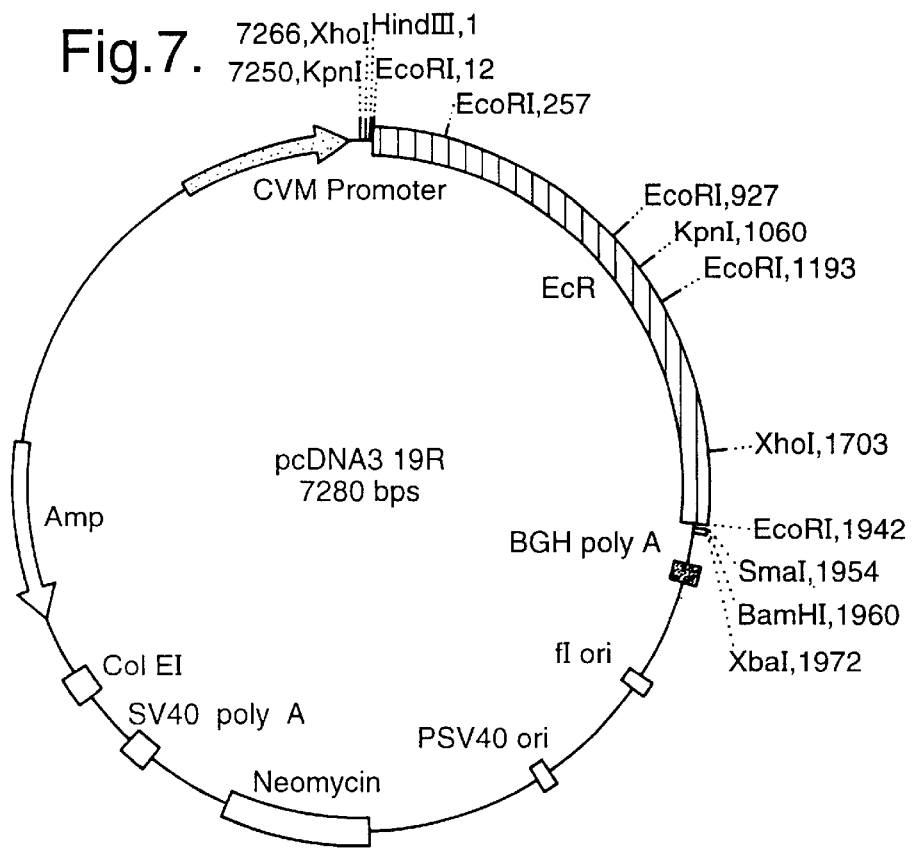
FIG. 7 shows a plasmid map of the clone pcDNA319R. The three other mammalian expression vectors were constructed in the same way and look similar but for the size of the insert.

A first mammalian expression plasmid was constructed by placing a HindIII/NotI pSK19R fragment into the pcDNA3 HindIII/NotI vector resulting in pcDNA319R (FIG. 7).

A second effector plasmid was constructed wherein the non-coding region of the cDNA 19R was deleted and a consensus Kozak sequence introduced. The mutagenesis was carried out by PCR amplifying a DNA fragment with the oligo HecRH3C:

5'aattaagcttccaccatgccgttaccaatgccaccgaca 3' (SEQ ID NO: 31) containing a unique HindIII restriction enzyme recognition site followed by the mammalian Kozak consensus sequence, and HecRNdeI:

5'cttcaaccgacactcctgac 3' (SEQ ID NO: 32).

The resulting 353 bp PCR fragment was restriction enzyme digested with HindIII and NdeI, gel purified and ligated with 19R NdeI/NotI fragment into a pcDNA3 HindIII/NotI vector resulting in pcDNA3HecR.

A third effector construct was made with the 5' end sequences of pSK16.1 by PCR. The PCR approach involved PCR amplifying the 5' end sequences using a 5' oligonuclotide containing a HindIII restriction cloning site, the Kozak consensus sequence followed by nucleotide sequence encoding for a Methionine start and two Arginines to be added to the 5' end of the amplified fragment: (16H3K 5' attaagcttgccgccatgcgccgacgctggtataacaacggaccattc 3' (SEQ ID NO: 33)), the 3' oligonucleotide used was HecrNdeI. The resulting fragment was restriction enzyme digested, gel purified and subcloned with an NdeI/NotI 19R fragment into pcDNA3 NdeI/NotI vector. The plasmid was named pcDNA3H3KHEcR.

A fourth effector construct was produced which contains the extended N-terminal end sequence obtained from the 5'RACE experiment. Thus, a PCR approach was followed to introduce the new 5' end sequences in addition to a consensus Kozak sequence and a HindIII unique cloning sequence. The sense oligonucleotide used was RACEH3K:

5' attaagcttgccgccatgtccctcggcgctcgtggatac 3' (SEQ ID NO: 34), while the antisense primer was the same as that used before (HecrNdeI). The cloning strategy was the same as used for the pcDNA3H3KHEcR to give rise to pcDNA3RACEH3KHEcR.

The PCR mutagenesis reactions were carried out in the same manner for all constructs. The PCR conditions used were 1 minute at 94° C., 1 minute at 60° C. and 1 minute at 72° C. for 15 cycles. The reactions conditions were 50 mM Tris-HCl (pH8.4), 25 mM KCl, 200 mM dNTPs (dATP, dCTP, dGTP and dTTP), 200 nM of each oligonucleotide and 2.5U/Reaction of Taq DNA polymerase. For each construct at least 5 independant PCR reactions were carried out and several clones were sequenced to insure that at least one is mutation free.

Reporter Construct

The reporter plasmid to be co-transfected with the expression vector contained 4 copies of the Hsp27 ecdysone response element (Riddihough and Pelham, 1987) fused to B-globin promoter and the B-Galactosidase gene. The tandem repeats of the ecdysone response element were synthesised as two complementary oligonucleotides which when annealed produced a double standed DNA molecule flanked by an SpeI site at the 5' end and a ClaI site at the 3' end:

R e c r 3 A 5'ctagtagacaagggttcaatgcact-tgtccaataagcttagacaagggt-tcaatgcacttgtccaatgaattcagacaagggttcaat gcacttgtccaatctg-cagagacaagggttcaatgcacttgtccaatat 3' (SEQ ID NO: 35)

R e c r 3 B 5'cgatattggacaagtgcattgaaccct-tgtctctgcagattggacaagtgcat-tgaacccttgtctgaattcattggacaagtgcattg aacccttgtctaagcttat-tggacaagtgcattgaacccttgtcta 3' (SEQ ID NO: 36).

Figure 8:
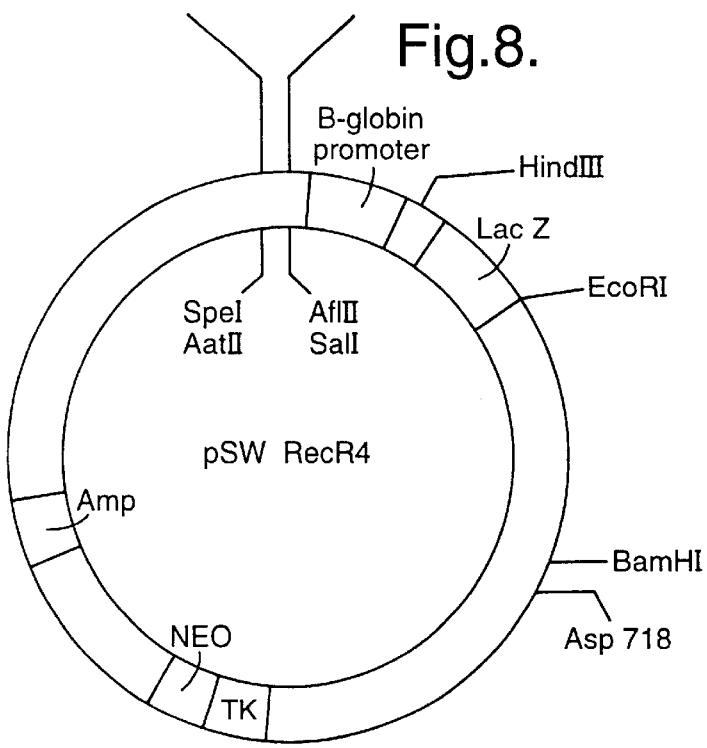
FIG. 8 shows a plasmid map of the reporter construct used to analyse the activity of the *Heliothis virescens* ecdysone receptor.

The resulting 135 bp DNA fragment was ligated to the vector pSWBGAL SpeI/ClaI resulting in pSWREcR4 (FIG. 8). The co-transfection of the two plasmid should result in B-galactosidase activity in the presence of ligand. The experiment relies upon the presence of RXR (a homologue of ultraspiracle) in mammalian cells for the formation of an active ecdysone receptor.

Mammalian Transfection Methods

Transfections of mammalian cell lines (CHO-K1 Chinese hamster ovary)-ATCC number CCL61 or cos-1 (Monkey cell line) were performed using either calcium phosphate precipitation (Gorman, Chapter 6 of "DNA cloning: a practical approach. Vol 2 D. M. Glover ed/.(1985) IRL Press, Oxford) or using LipofectAMINE (Gibco BRL Cat. No. 18324-012, following manufacturers instructions). Human Epithelial Kidney 293 cells were transfected using analogous methods.

Figure 9:
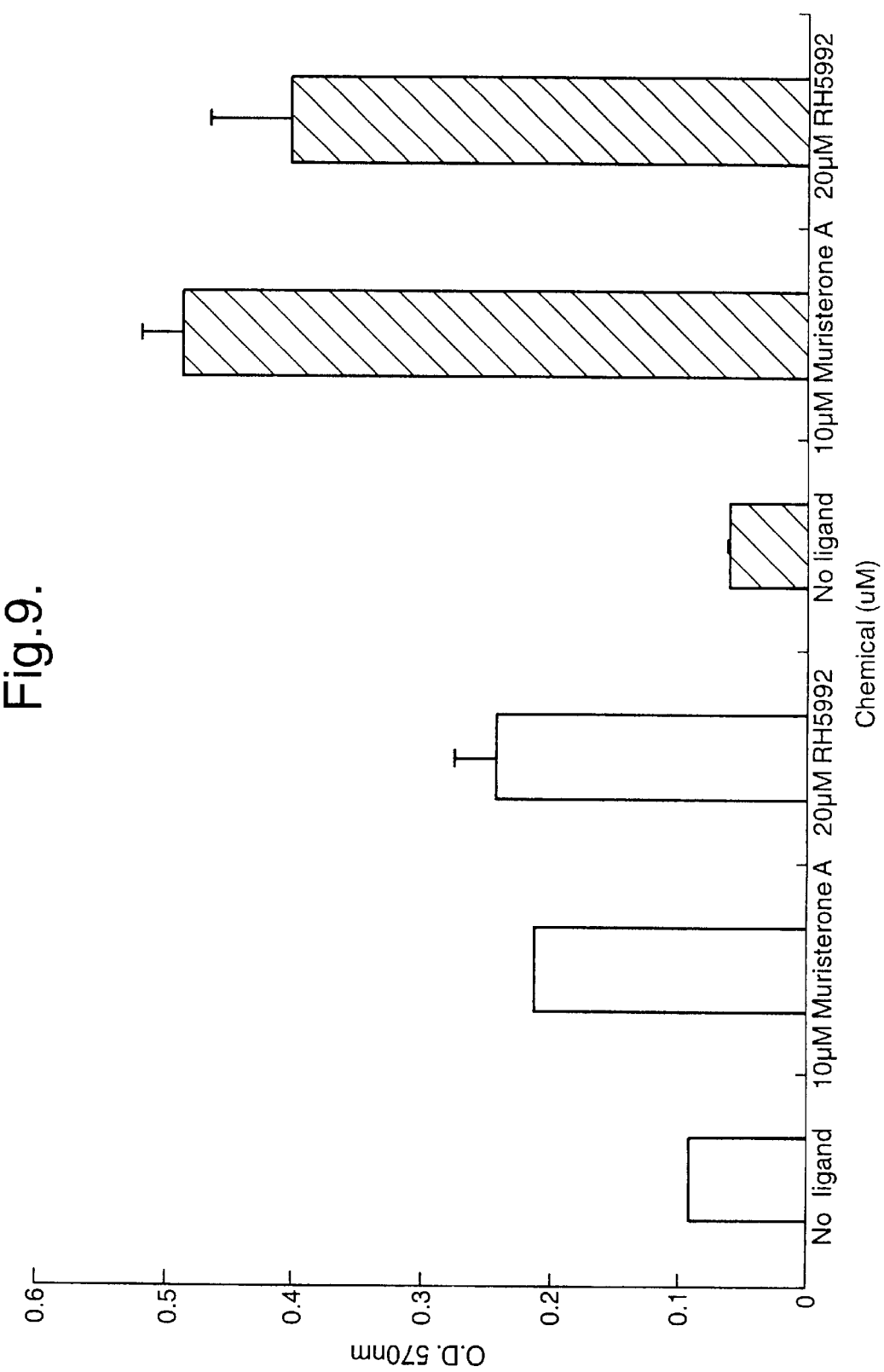
FIG. 9 is a graph which shows the effect of Muristerone A and RH5992 in reporter activity in HEK293 cells co-transfected with pcDNA3H3KHEcR alone (filled bars) or with αRXR (stripped bars)

Results—Native HEcR Drives Transient Reporter Gene Expression in Mammalian Cells Co-transfection of pcDNA3H3KHEcR (Effector) and reporter constructs into Human Epithelial Kidney 293 cells (HEK293) in the presence of either Muristerone A or RH5992 resulted in a 2–3 fold induction of reporter activity compared to the no chemical controls (FIG. 9). The HEK293 cells were used since they are known to have constitutive levels of αRXR which have been demonstrated to be necessary for Drosophila EcR activation by Muristerone A (Yao., et al., 1993). Moreover, to further investigate the need for RXR interactions, a αRXR was co-transfected into HEK293 cells (along with the effector and reporter) resulting in a 9 fold induction of reporter activity compared to the untreated cells (FIG. 9). The co-transfection of αRXR with reporter and effector increased by four fold the reporter activity compared to cells transfected with effector and reporter alone. Induction was observed both in the presence of either Muristerone A or RH5992. These data clearly demonstrate that the cDNA HEcR encodes a functional ecdysone receptor. Moreover, The ability of HEcR to complex with αRXR and bind Muristerone A or RH5992 provide evidence for the usage of the entire HEcR as a component of a mammalian gene switch. In particular, it offers the advantage of reducing uninduced expression of target gene since ecdysone receptor and response elements are not present in mammalian cells.

EXAMPLE III

Chimeric Constructs and Ligand Validation in Maize Protoplasts

In order to apply the ecdysone receptor as an inducible system it was deemed necesary to simplify the requirements of the system by avoiding the need of a heterodimer formation to obtain an active complex. The glucocorticoid receptor is known to form homodimers and chimeric constructs of the glucocorticoid receptor transactivating and DNA binding domains fused to the ecdysone receptor hinge and ligand binding domains have been shown to be active as homodimers in mammalian cells in the presence of Muristerone A (an ecdysone agonist)(Christopherson et al., 1992). However, the chimeric receptor is not responsive to 20-hydroxyecdysone (Christopherson et al., 1992).

The analysis of the activation of the glucocorticoid/ Heliothis ecdysone chimeric receptor entailed the production of two other control effector constructs. The first one of the constructs contained the intact glucocorticoid receptor while the second one contained a glucocorticoid/Drosophila ecdysone chimeric receptor.

Effector Constructs (i) Glucocorticoid Receptor Maize Expression Construct

The glucocorticoid receptor DNA for the Maize transient expression construct was produced via the polymerase chain reaction (PCR) of Human Fibrosarcoma cDNA (HT1080 cell line, ATCC#CC1121) library (Clontech)(see Hollenberg et al., 1985). The PCR approach taken was to amplify the 2.7 kb fragment encoding the glucocorticoid receptor in two segments. The first segment entails the N-terminal end up to and including the DNA binding domain while the second fragment begins with the hinge region (amino acid 500) thought to the end of the reading frame. Thus, the PCR primer for the N-terminal end segment was designed to contain an EcoRI site and the Kozak consensus sequence for translation initiation GREcoRI 5'attgaattccaccatggactccaaagaatcattaactc 3' (SEQ ID NO: 37).

The 3'end primer contains a XhoI site in frame with the reading frame at amino acid 500 of the published sequence: GRXhoI 5' gagactcctgtagtggcctcgagcattccttttattttttc 3' (SEQ ID NO: 38).

The second fragment of the glucocorticoid receptor was produced with a 5' end oligonucleotide containing an XhoI site in frame with the open reading frame at the begining of the hinge region (amino acid 500): GRHinge 5' attctcgagattcagcaggccactacaggag 3' (SEQ ID NO: 39) while the 3' end oligonucleotide contained an EcoRI site 400 bp after the stop codon: GRStop 5' attgaattcaatgctatcgtaactatacaggg 3' (SEQ ID NO: 40).

The glucocorticoid receptor PCR was carried out using Vent polymerase (Biolabs) under hot start conditions followed by 15 cycles of denaturing (94° C. for 1 minute), annealing (66° C. for 1 minute) and DNA synthesis (72° C. for 3 minute). The template was produced by making first strand cDNA as described in the TA cloning kit (Invitrogen) after which the PCR was carried out in 10 mM KCl, 10 mM $(NH_4)_2SO_4$, 20 mM TRIS-HCl pH 8.8, 2 mM $MgSO_4$, 0.1% (v/v) Triton X-100, 200 mM dNTPs, 100 ng of each Primer and 2 U of Vent Polymerase. The PCR products was restriction enzyme digested with EcoRI and XhoI and subcloned into pBluescript SK (pSK) EcoRI. The resulting plasmid pSKHGI was sequenced and found to lack any mutations from the published sequences (apart from those introduced in the PCR primers) (Hollenberg et al., 1985).

Figure 10:
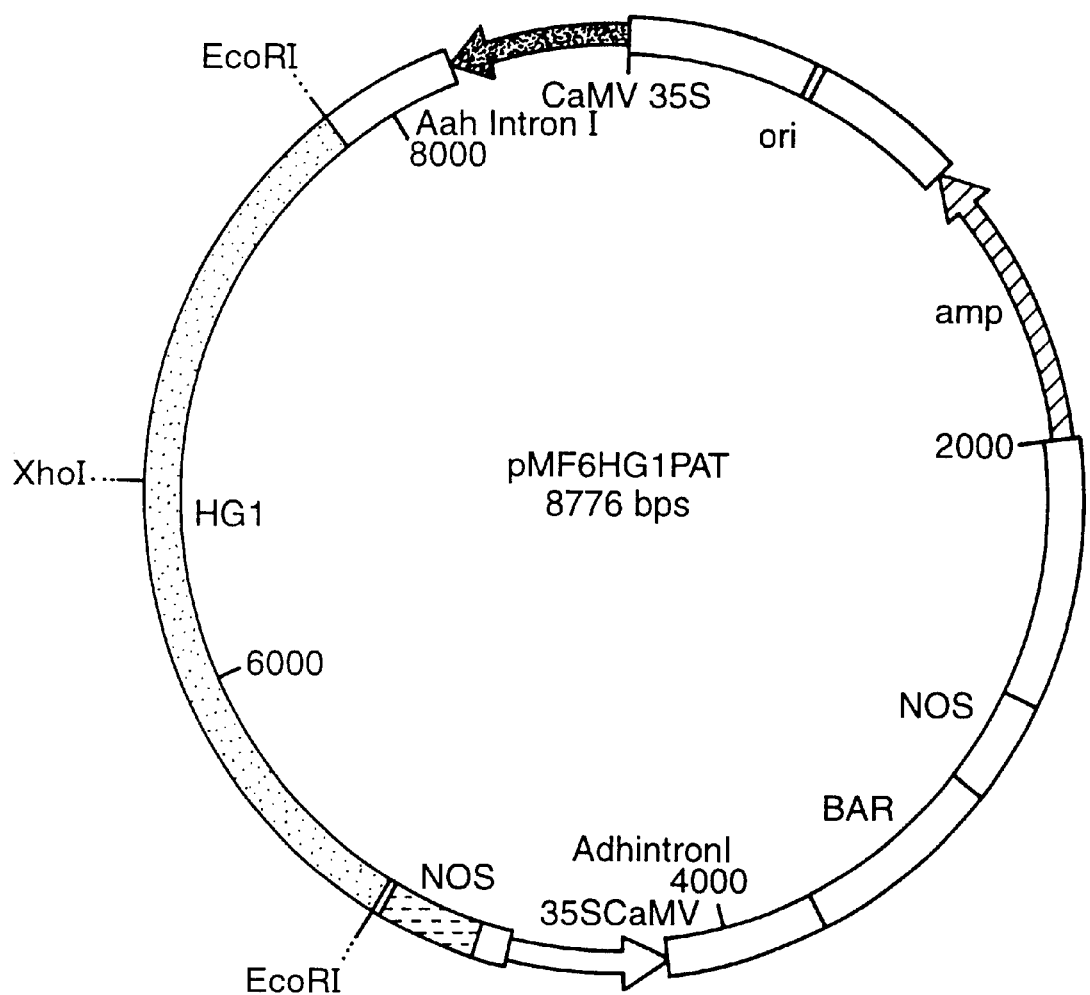
FIG. 10 shows a plasmid map of the Maize expression vector containing the Glucocorticoid receptor (HG1 or pMF6HG1PAT)
Figure 11:
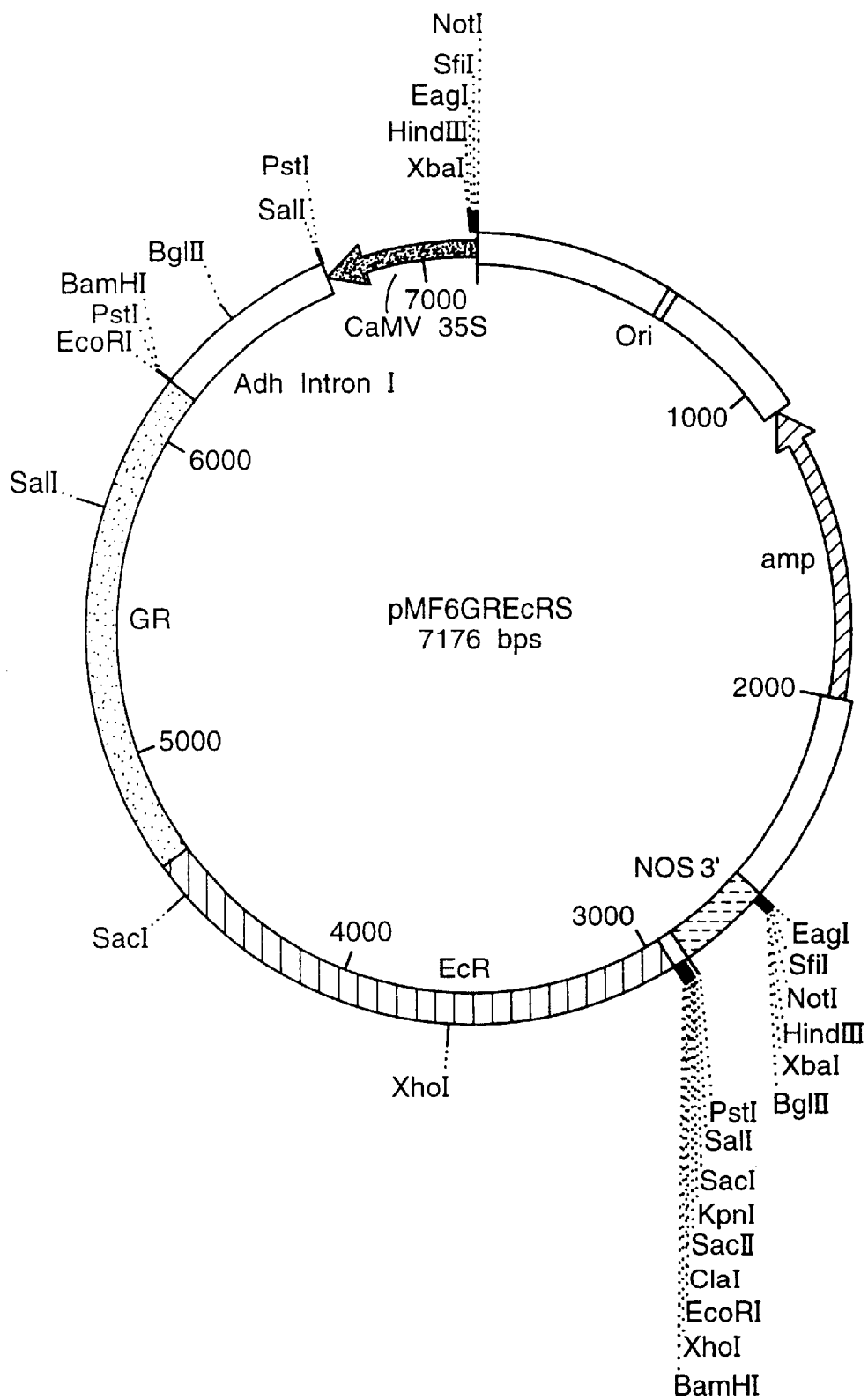
FIG. 11 shows a plasmid map of the maize expression vector containing the chimeric glucocorticoid/Drosophila ecdysone receptor pMF6GREcRS.
Figure 12:
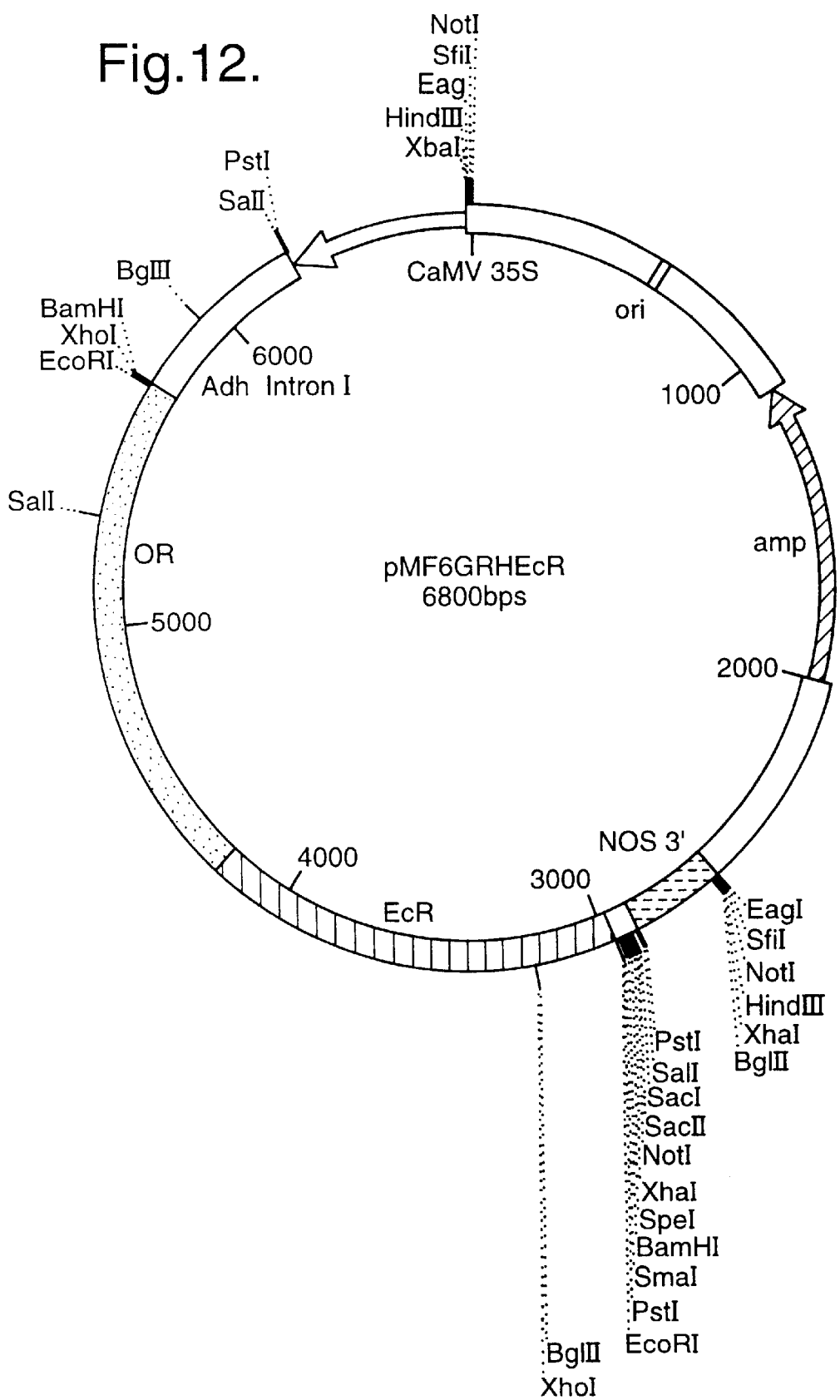
FIG. 12 shows a plasmid map of the maize expression vector containing the chimeric glucocorticoid/Heliothis ecdysone receptor pMF6GRHEcR.

The 2.7kb EcoRI fragment was subcloned into the vector pMF6PAT EcoRI resulting in pMF6HGIPAT (FIG. 10).

(ii) Maize Expression Construct Containing a Glucocorticoid/Drosophila Ecdysone Chimeric Receptor The glucocorticoid receptor portion of the chimeric receptor was isolated from pSKHGI by producing a 1.5 kb BamHI/XhoI restriction fragment containing the N-terminal end up to and including the DNA binding domain.

The Drosophila ecdysone receptor portion was isolated through PCR of first stand cDNA prepared from Drosophila adult mRNA. The PCR was carried out using a 5' oligonucleotide containing a SalI site (ie. Drosophila ecdysone receptor contains a XhoI site at the end of the ligand binding domain) which starts at the begining of the hinge region: amino acid 330, Ecr8 attgtcgacaacggccggaatggctcgtcccggag 3' (SEQ ID NO: 41).

The 3' end oligonucleotide contains an BamHI site adjacent to the stop codon: EcRstop 5' tcgggctttgttaggatcctaagccgtggtcgaatgctccgacttaac 3' (SEQ ID NO: 42).

The PCR was carried out under the conditions described for the amplification of the Glucocorticoid receptor and yielded a 1.6 kb fragment. The fragment was introduced into pSK SalI/BamHI and the sequence determined and compared to the published one (Koelle et al.,1991).

The maize transient expression plasmid was produced by introducing into pMF6 BamHI vector the 1.5 kb BamHI/ XhoI glucocorticoid receptor fragment and the 1.6 kb SalI/ BamHI Drosophila receptor portion to yield the chimeric plasmid pMF6GREcRS (FIG. 9).

(iii) Construction of the Glucocorticoid/Heliothis Ecdysone Chimeric Receptor Maize Transient Expression Plasmid The Glucocorticoid receptor portion of the chimera was produced as describe in Example II(ii). The production of the Heliothis ecdysone receptor portion involves the introduction of a SalI recognition site at the DNA binding/hinge domain junction (amino acid 229). The addition of the SalI site: Hecrsal 5'attgtcgacaaaggcccgagtgcgtggtgccggag 3' (SEQ ID NO: 43) was achieved via PCR mutagenesis making use of an unique AccI site 107 bp downstream of the juction point (or 1007 bp relative to Seq ID No 4): Hecracc 5' tcacattgcatgatgggaggcatg 3' (SEQ ID NO: 44).

The PCR was carried out using Taq polymerase (2.5 U) in a reaction buffer containing 100 ng of template DNA (pSK19R), 100 ng of Hecrsal and Hecracc, 20 mM TRIS-HCl pH 8.4, 50 mM KCl, 10 mM $MgCl_2$, 200 mM dNTPs. The reaction was carried out with an initial denaturation of 3 minutes followed by 15 cycles of denaturation (1 minute at 94° C.), annealing (1 minute at 60° C.) and DNA synthesis (1 minute at 72° C.). The DNA was restriction enzyme digested and subcloned into pSK SalI/SacI with the 1.2 kb AccI/SacI 3' end HecR fragment to yield pSK HeCRDEF (or containing the hinge and ligand binding domains of the Heliothis ecdysone receptor). The construction of the maize transient expression plasmid containing the Glucocorticoid/Heliothis ecdysone chimeric receptor involved the ligation of pMF6 EcoRI/SacI with the 1.5 kb EcoRI/XhoI fragment of Glucocorticoid receptor N-terminal end and the 1.2 kb SalI/SacI fragment of pSk HEcRDEF to yield pMF6GRHEcR (FIG. 10).

Reporter Plasmids

Two reporter plasmids were made by inserting the into p221.9 or p221.10 BamHI/HindIII vectors two pairs or oligonucleotides containing six copies of the glucocorticoid response element (GRE). The two sets of oligonucleotides were designed with restriction enzyme recognition sites so as to ensure insertion of the two pairs in the right orientation. The first oligonucleotide pair GRE1A/B is 82 nucletides long and when annealed result in a DNA fragment flanked with a HindIII site at the 5' end and a SalI site at the 3' end: GRE1A 5 'agcttcgactgtacaggatgttctagc-tactcgagtagctagaacatcctgtacagtcgagtagctagaacatctgtacag 3' (SEQ ID NO: 45) GRE1B 5'tcgactgtacaggatgttctagctactc-gactgtacaggatgttctagctactcgagtcgctagaacatcctgta cagtcga 3' (SEQ ID NO: 46).

The second pair of oligonucleotides is flanked by a SalI site at the 5' end and a BamHI site at the the 3' end GRE2A 5' tcgactagctagaacatcctgtacagtc-gagtagctagaacatcctgtacagtcgagtagctagaacatcctgtacag 3' (SEQ ID NO: 47) GRE2B 5' gatcctgtacaggatgtttctagc-tactcgactgtacaggatgttctagctactcgactgtacaggatgttctagctag 3' (SEQ ID NO: 48).

Figure 13:
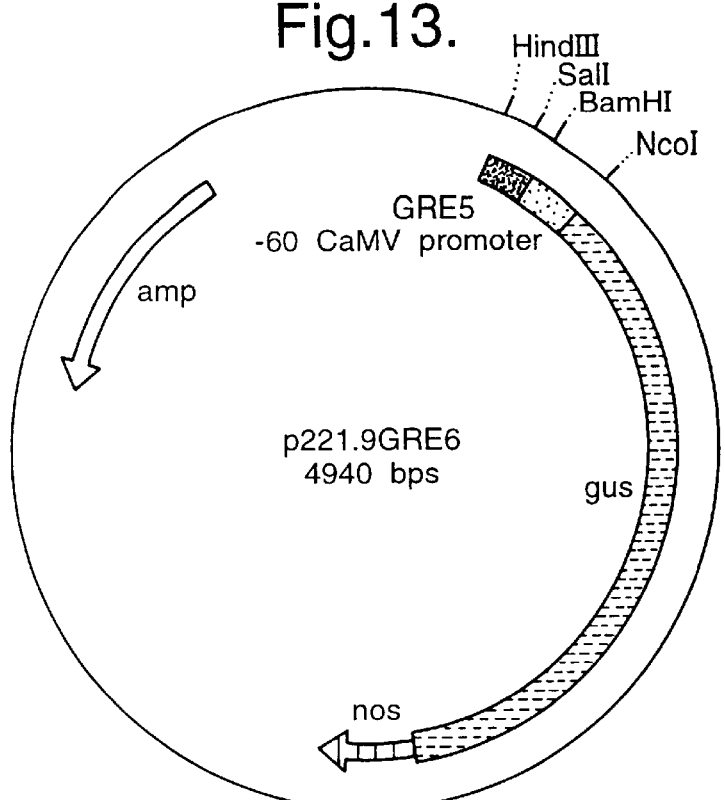
FIG. 13 shows a plasmid map of the plant reporter Plasmid containing the glucocorticoid response elements fused to the −60 S35CaMV promoter fused to GUS, p221.9GRE6.
Figure 14:
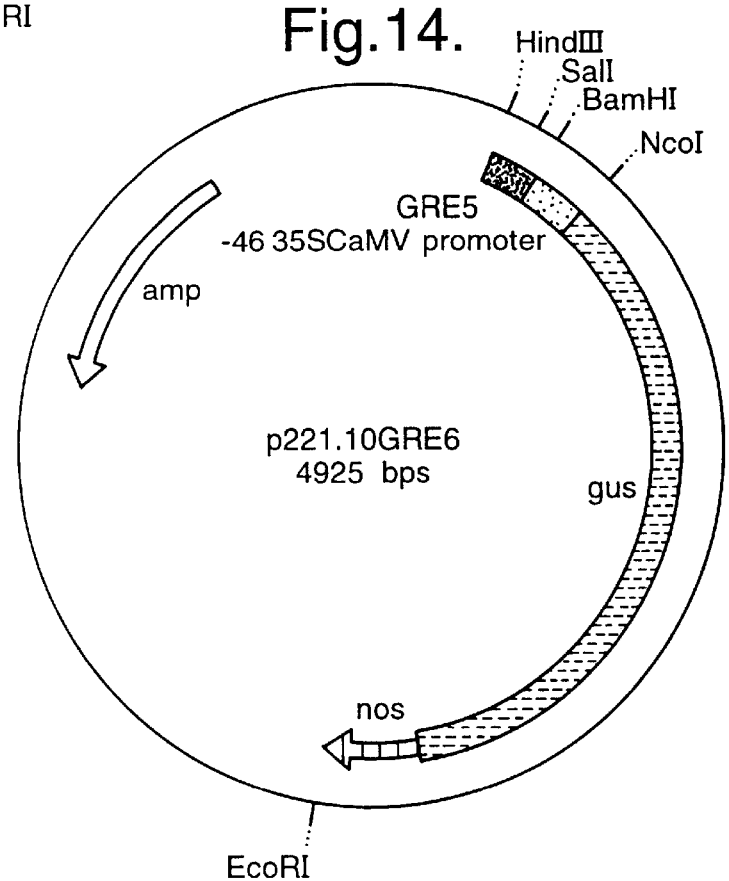
FIG. 14 shows a plasmid map of the plant reporter plasmid containing the glucocorticoid response elements fused to the −46 S35CaMV promoter fused to GUS, p221.10GRE6.

The resulting plasmids were named p221.9GRE6 (FIG. 13) and p221.10GRE6 (FIG. 14)(used in later Example). The difference between p221.9 and p221.10 plasmid is that p221.9 contains the −60 35SCaMV minimal promotor while p221.10 (p221.10GRE6) contains the −46 35SCaMV minimal promotor.

Method

Protoplasts were isolated from a maize suspension culture derived from BE70×A188 embryogenic callus material, which was maintained by subculturing twice weekly in $MS0.5_{mod}$. (MS medium supplemented with 3% sucrose, 690 mg/l proline, 1 g/l myo-inositol, 0.2g/l casein acid hydrolysate, 0.5 mg/l 2,4-D, pH5.6). Cells from suspensions two days post subculture were digested in enzyme mixture (2.0% Cellulase RS, 0.2% Pectolyase Y23, 0.5M Mannitol, 5 mM $CaCl_2 2H_2O$, 0.5% MES, pH5.6, ~660 mmol/kg) using ~10 ml/g cells, incubating at 25° C., dim light, rotating gently for ~2 hours. The digestion mixture was sieved sequentially through 250 μm and 38 μm sieves, and the filtrate centrifuged at 700 rpm for 3.5 minutes, discarding the supernatant. The protoplasts were resuspended in wash buffer (0.358M KCl, 1.0 mM $NH_4NO_3$, 5.0 mM $CaCl_2 2H_2O$, 0.5 mM $KH_2PO_4$, pH4.8, ~670 mmol/kg) and pelleted as before. This washing step was repeated. The pellet was resuspended in wash buffer and the protoplasts were counted. Transformation was achieved using a Polyethylene glycol method based on Negrutiu et.al. Protoplasts were resuspended at $2×10^6$/ml in MaMg medium (0.4M Mannitol, 15 mM $MgCl_2$, 0.1% MES, pH5.6, ~450 mmol/kg) aliquotting 0.5 ml/treatment (i.e. $1×10^6$ protoplasts/treatment). Samples were heat shocked at 45° C. for 5 minutes then cooled to room temperature. 10 μg each of p221.9GRE6 and pMF6HR1PAT (GR) (1 mg/ml)/treatment were added and mixed in gently, followed by immediate addition of 0.5 ml warm (~45° C.) PEG solution (40% PEG 3,350MW in 0.4M Mannitol, 0.1M $Ca(NO_3)_2$, pH8.0), which was mixed in thoroughly but gently. Treatments were incubated at room temperature for 20–25 minutes, then 5 ml 0.292M KCl (pH5.6, ~530 mmol/kg) was added step-wise, 1 ml at a time, with mixing. The treatments were incubated for a further 10–15 minutes prior to pelleting the protoplasts by centrifuging as before. Each protoplast treatment was resuspended in 1.5 ml culture medium (MS medium, 2% sucrose, 2 mg/l 2,4-D, 9% Mannitol, pH5.6, ~700 mmol/kg)+/−0.0001M dexamethasone (glucocorticoid). The samples were incubated in 3 cm dishes at 25° C., dark, for 24–48 hours prior to harvesting. Fluorometric assays for GUS activity were performed with the substrate 4-methylumbelliferyl-D-glucuronide using a Perkin-Elmer LS-35 fluorometer (Jefferson et al., 1987). Protein concentration of tissue homogenates were determined by the Bio-Rad protein assay (Bradford, 1976). The method was repeated for each effector construct.

Results

Reporter Gene Assay

A reporter gene construct (p221.9GRE6) was generated containing the GUS reporter gene under the control of a −60 CaMV 35S promoter with 6 copies of the glucocorticoid response element. To test this construct was functional in maize protoplasts a co-transformation assay was performed with the reporter construct p221.9GRE6 and the effector construct pMF6HR1PAT (GR) construct containing the entire glucorticoid receptor.

Figure 15:
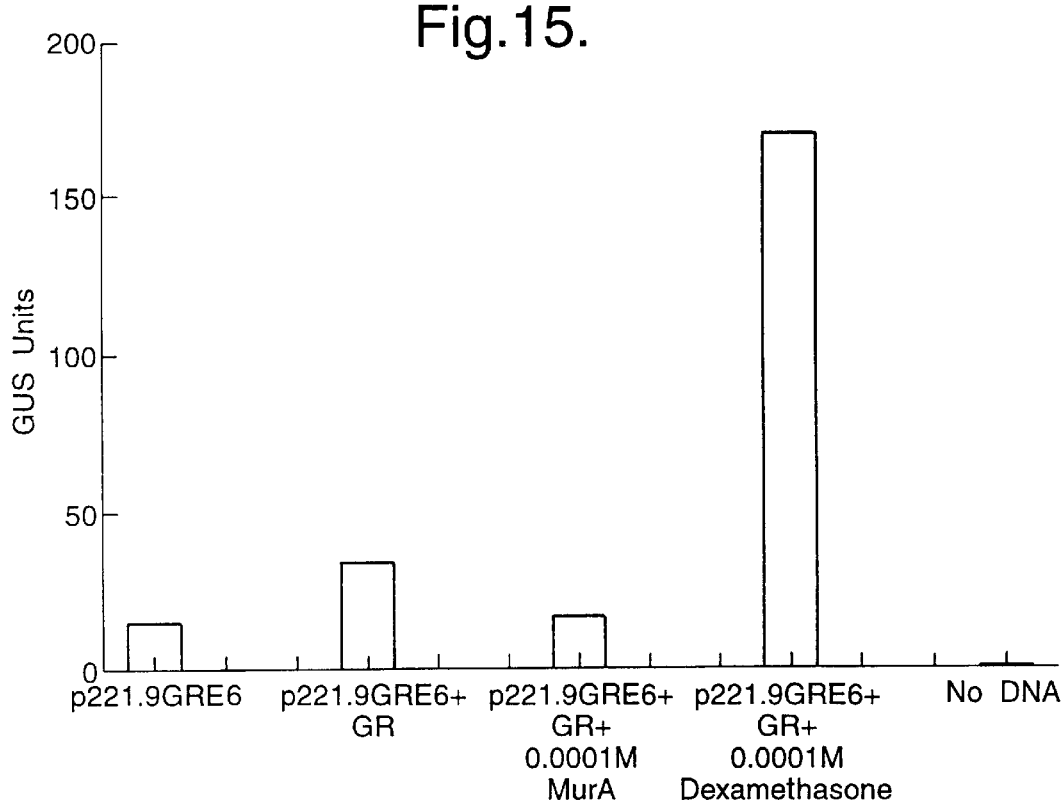
FIG. 15 shows a graph showing the effect of Muristerone A and Dexamethasone in Maize AXB protoplasts transformed with pMF6HG1PAT (GR) and p221.9GRE6 (reporter)

FIG. 15 shows that Reporter p221.9GRE6 alone or reporter plus effector pMF6HR1PAT (GR) with no activating chemical gave no significant expression. When reporter plus effector were co-transformed into maize protoplasts in the presence of 0.0001M dexamethasone (glucocorticoid), a significant elevation of marker gene activity was observed (FIG. 15). The response is specific to glucorticoid as the steroid Muristerone A does not lead to induced levels of expression. These studies clearly show the reporter gene construct p221.9GRE6 is capable of monitoring effector/ligand mediated gene expression.

Chimeric Ecdysone Effector Constructs Mediate Inducible Expression in Maize Transient Protoplasts Assays A chimeric effector plasmid pMF6GREcRS was constructed, containing the ligand binding domain from the Drosophila ecdysone receptor and the DNA binding and transactivation domain from the glucorticoid receptor. To confirm the reporter gene construct p221.9GRE6 could respond to a chimeric ecdysone effector construct, a series of co-transformation into maize protoplasts was performed.

Figure 16:
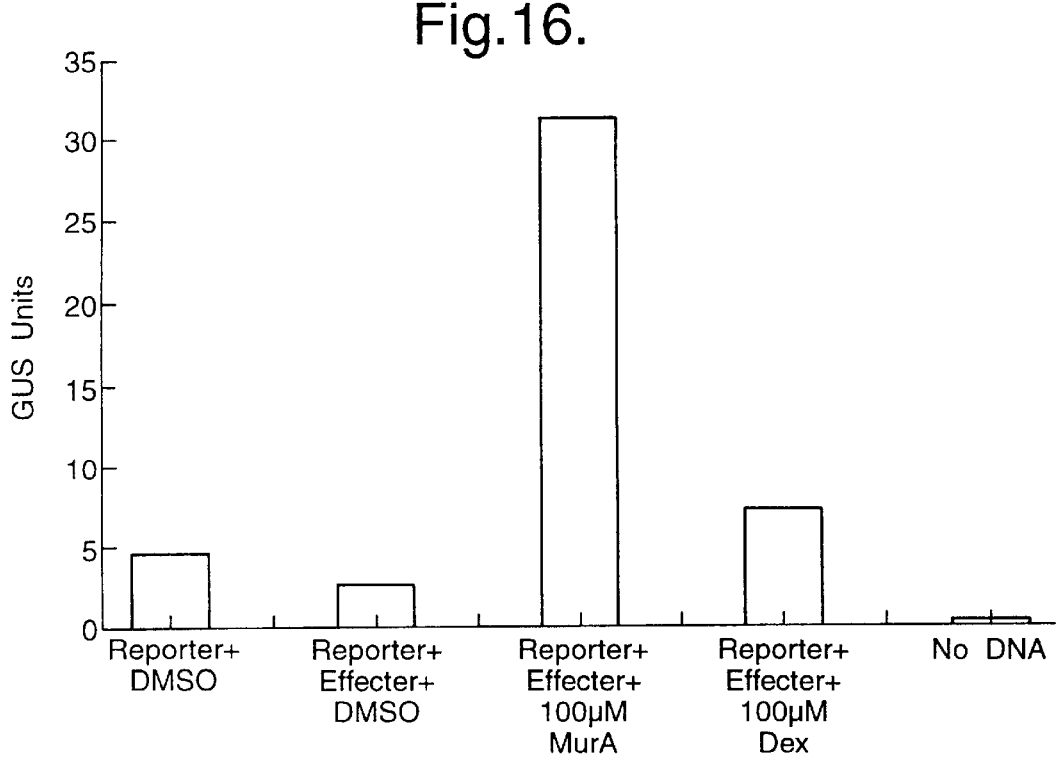
FIG. 16 shows a graph showing the effect of Muristerone A and Dexamethasone in Maize AXB protoplasts transformed with pMF6GREcRS (effector) and p221.9GRE6 (reporter)

FIG. 16 shows that reporter (p221.9GRE6) alone or reporter plus effector (pMF6GREcRS) with no activating chemical, gave no significant expression in maize protoplasts. When reporter plus effector were co-transformed into maize protoplasts in the presence of 100 pM Muristerone A, a significant elevation of marker gene activity was observed. The response was specific to Muristerone A, as the steroid dexamethasone did not lead to induced levels of expression. These studies clearly showed the reporter gene construct p221.9GRE6 is capable of monitoring chimeric ecdysone effector/ligand mediated gene expression.

Figure 17:
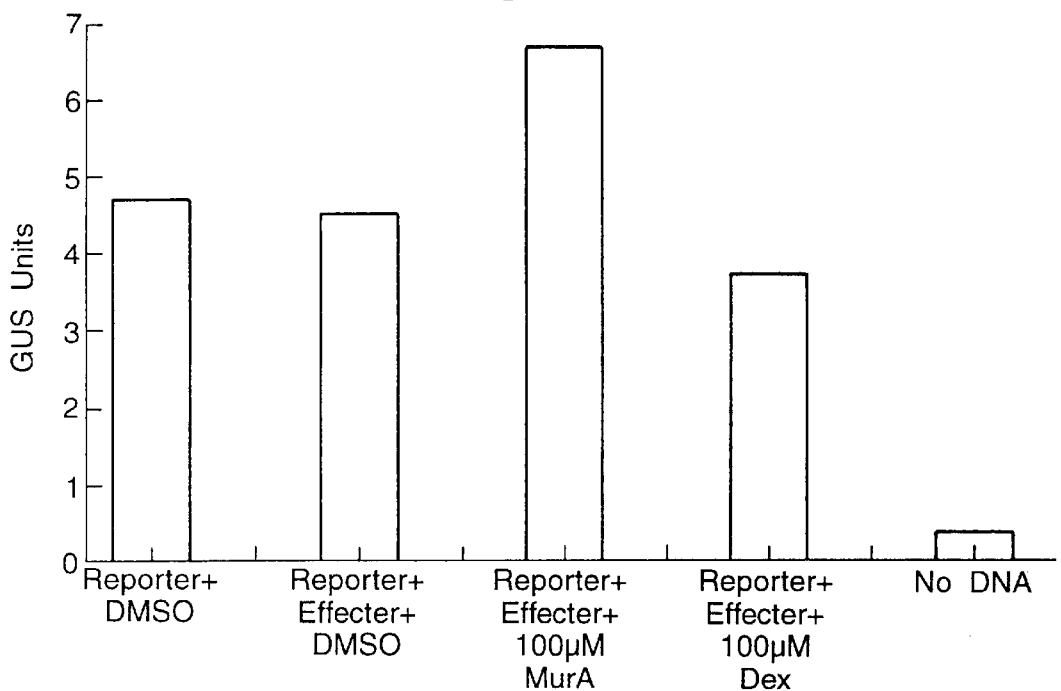
FIG. 17 shows a graph showing the effect of Muristerone A and Dexamethasone in Maize AXB protoplasts transformed with pMF6GRHEcR (effector) and p221.9GRE6 (reporter)

A second chimeric effector construct pMF6GRHEcR, was generated containing the ligand binding domain from Heliothis ecdysone receptor. When co-transformed into maize protoplasts with the reporter plasmid p221.9GRE6, no response to 100 μM Muristerone or 100 μM dexamethasone was observed (FIG. 17). These data clearly show the Drosophila and Heliothis ligand binding domains exhibit different properties.

Figure 18:
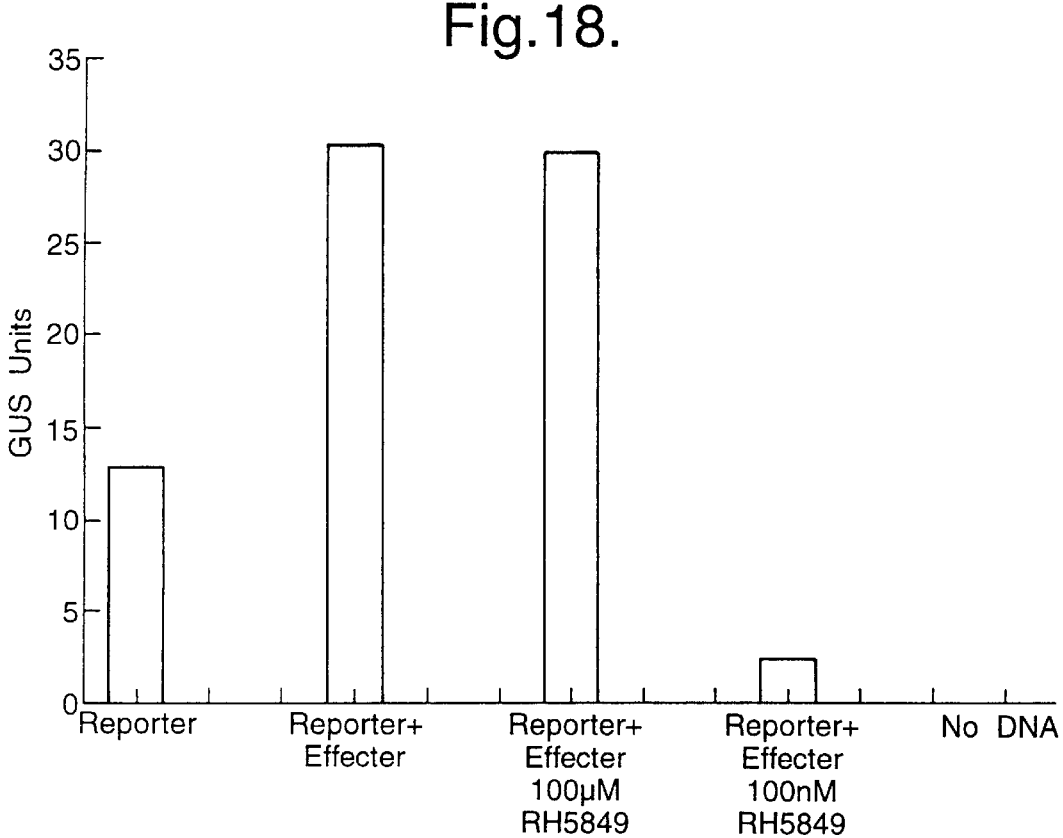
FIG. 18 shows a graph showing the effect of RH5849 in Maize AXB protoplasts transformed with pMF6GREcRS (effector) and p221.9GRE6 (reporter)
Figure 19:
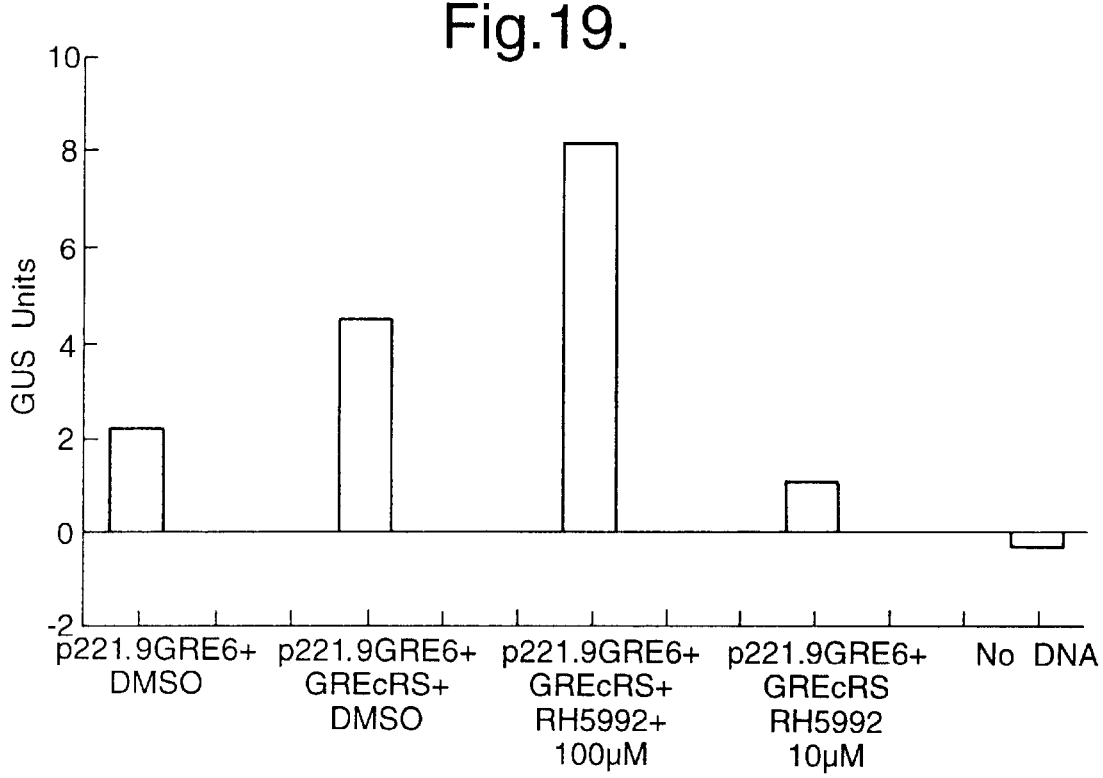
FIG. 19 shows a graph showing the effect of RH5992 in Maize AXB protoplasts transformed with pMF6GREcRS (effector) and p221.9GRE6 (reporter)

When the effector plasmid pMF6GREcRS, containing the ligand binding domain from Drosophila, was tested with the reporter p221.9GRE6 in presence of the non-steroidal ecdysone agonists RH5849 and RH5992 (mimic), no chemical induced reporter gene activity was observed (FIGS. 18 and 19).

Figure 20:
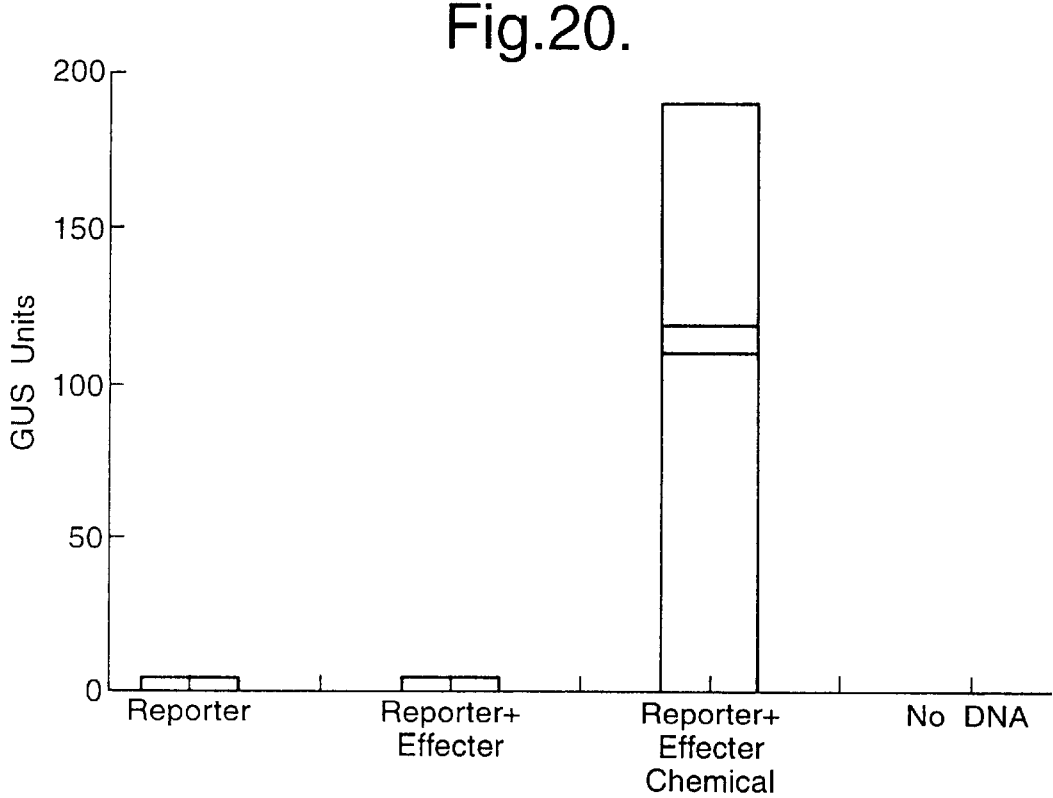
FIG. 20 shows a graph showing the effect of RH5992 in Maize AXB protoplasts transformed with pMF6GRHEcR (effector) and p221.9GRE6 (reporter)
Figure 21:
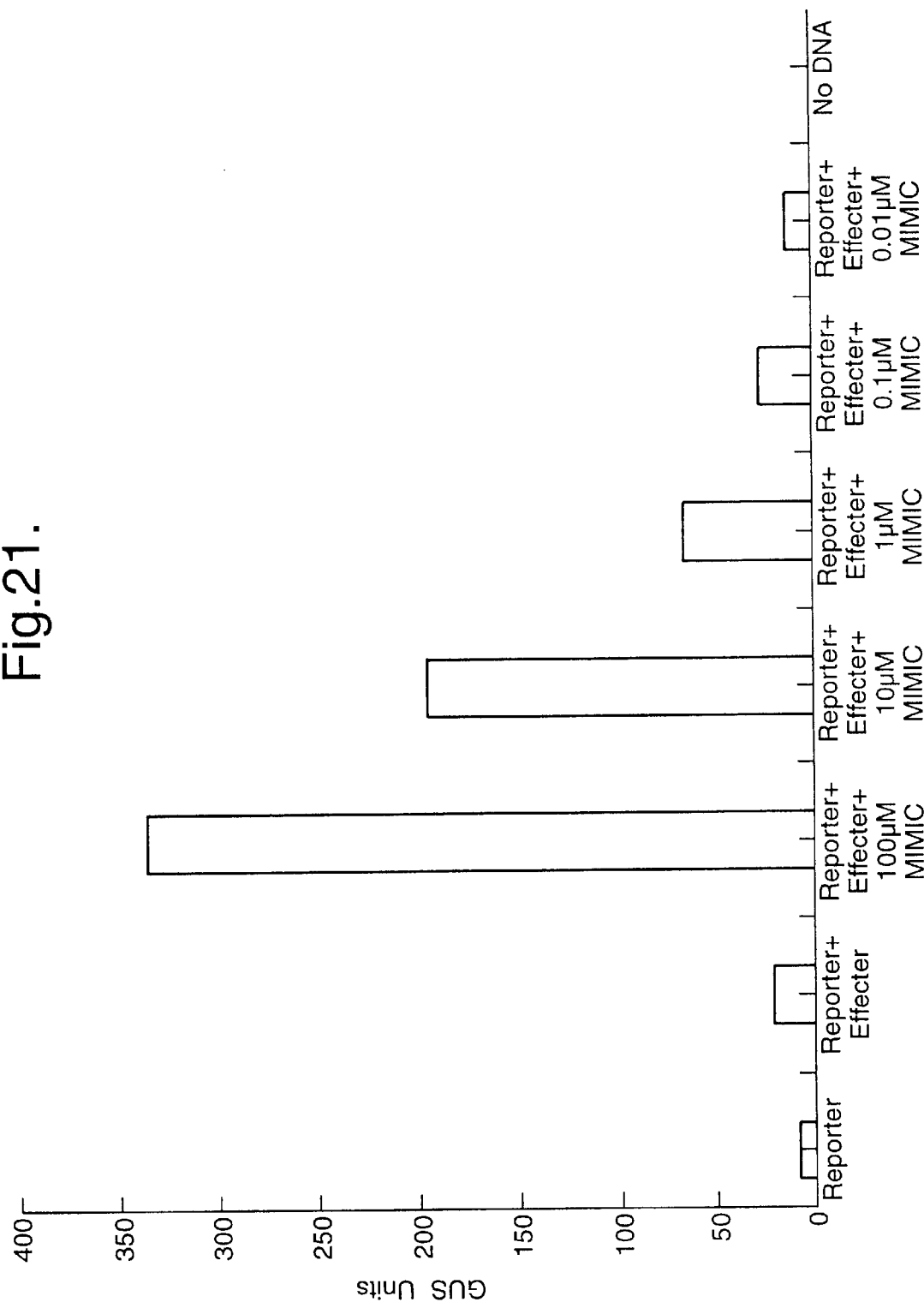
FIG. 21 shows a graph which shows the dose response effect of RH5992 in Maize AXB protoplasts transformed with pMF6GRHEcR (effector) and p221.9GRE6 (reporter)

When the effector plasmid pMF6GRHEcR, containing the ligand binding domain from Heliothis, was tested with the reporter p221.9GRE6 in presence of the non-steroidal ecdysone agonists RH5992 (mimic), significant chemical induced reporter gene activity was observed (FIG. 20). These data demonstrate the ligand binding domain from Heliothis has different properties to the Drosophila receptor in that the former responded to the non-steroidal ecdysteroid agonist RH5992. FIG. 21 demonstrates the effector plasmid pMF6GRHEcR confers RH5992 dependant inducibility on the reporter p221.9GRE6 in a dose responsive manner. Induction was observed in a range from 1 μM–100 μM RH5992.

EXAMPLE IV

Testing of Effector Vectors in Tobacco Protoplasts

The experiments carried out in the previous example demonstrated the specific effect of RH5992 (mimic) on pMF6GRHEcR in maize protoplasts. It is the aim in this example to show the generic application to plants of the glucocorticoid/Heliothis ecdysone chimeric receptor switch system. Tobacco shoot cultures cv. Samsun, were maintained on solidified MS medium+3% sucrose in a controlled environment room (16 hour day/8 hour night at 25° C., 55% R.H), were used as the source material for protoplasts. Leaves were sliced parallel to the mid-rib, discarding any large veins and the slices were placed in CPW13M 13% Mannitol, pH5.6, ~860 mmol/kg) for ~1 hour to pre-plasmolyse the cells. This solution was replaced with enzyme mixture (0.2% Cellulase R10, 0.05% Macerozyme R10 in CPW9M (CPW13M but 9% Mannitol), pH5.6, ~600 mmol/kg) and incubated in the dark at 25° C. overnight (~16 hours). Following digestion, the tissue was teased apart with forceps and any large undigested pieces were discarded. The enzyme mixture was passed through a 75 μm sieve and the filtrate was centrifuged at 600 rpm for 3.5 minutes, discarding the supernatant. The pellet was resuspended in 0.6M sucrose solution and centrifuged at 600 rpm for 10 minutes. The floating layer of protoplasts was removed using a pasteur pipette and diluted with CPW9M (pH5.6, ~560 mmol/kg). The protoplasts were again pelleted by centrifuging at 600 rpm for 3.5 minutes, resuspended in CPW9M and counted. A modified version of the PEG-mediated transformation above was carried out. Protoplasts were resuspended at $2 \times 10^6$/ml in MaMg medium and aliquotted using 200 μl/treatment (i.e. $4 \times 10^5$ protoplasts/treatment). 20 μg each of pMF6GRHEcRS and p221.9GRE6 DNA (1 mg/ml) were added followed by 200 μl PEG solution and the solutions gently mixed. The protoplasts were left to incubate at room temperature for 10 minutes before addition of 5 ml MSP19M medium (MS medium, 3% sucrose, 9% Mannitol, 2 mg/l NAA, 0.5 mg/l BAP, pH5.6, ~700 mmol/kg)+/−10 μM RH5992. Following gentle mixing, the protoplasts were cultured in their tubes, lying horizontally at 25° C., light. The protoplasts were harvested for the GUS assay after ~24 hours.

Effector Construct (i) Construction of a Dicotyledonous Expression Vector

Figure 22:
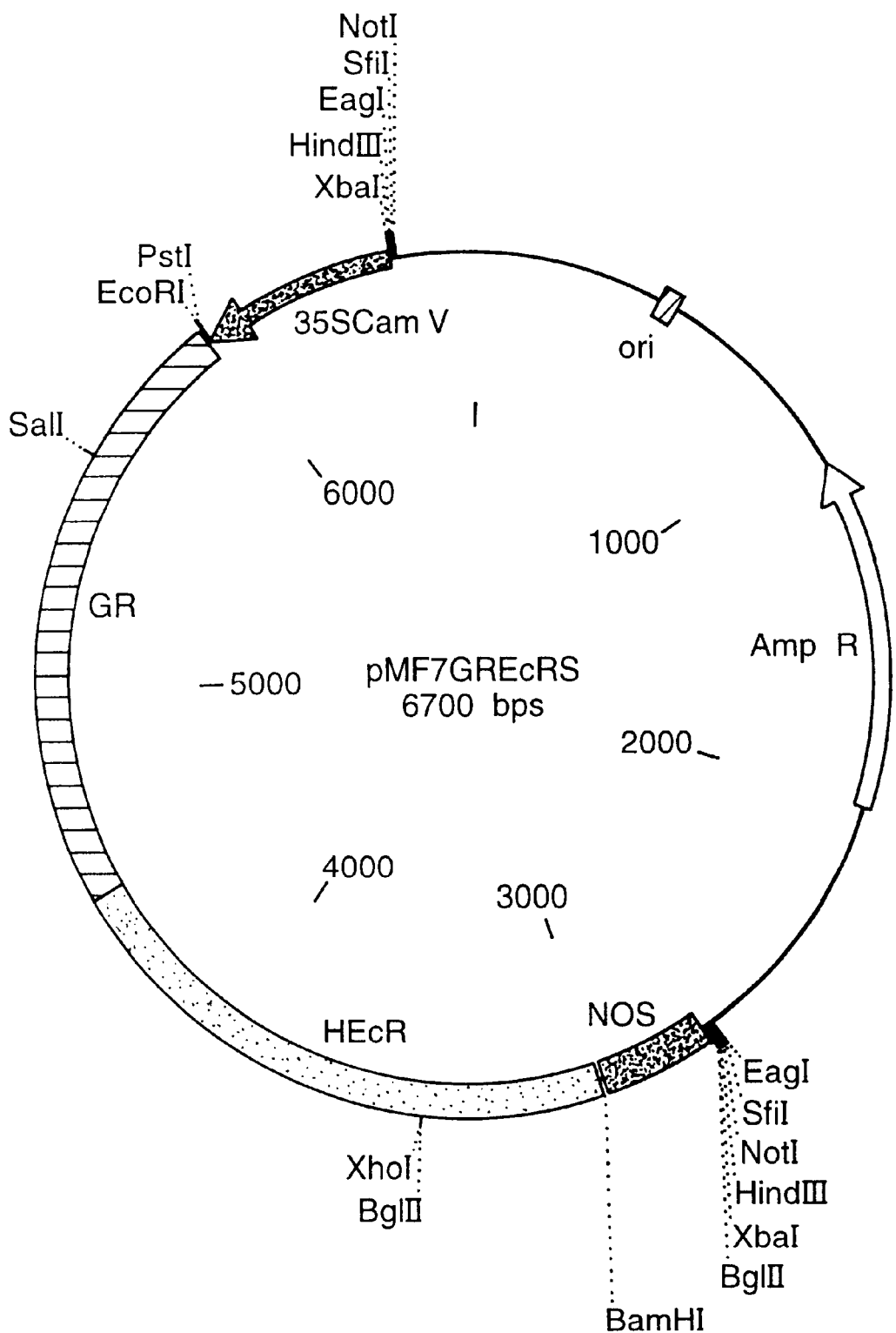
FIG. 22 shows a plasmid map of the tobacco expression vector containing the chimeric glucocorticoid/Drosophila ecdysone receptor, pMF7GREcRS.
Figure 23:
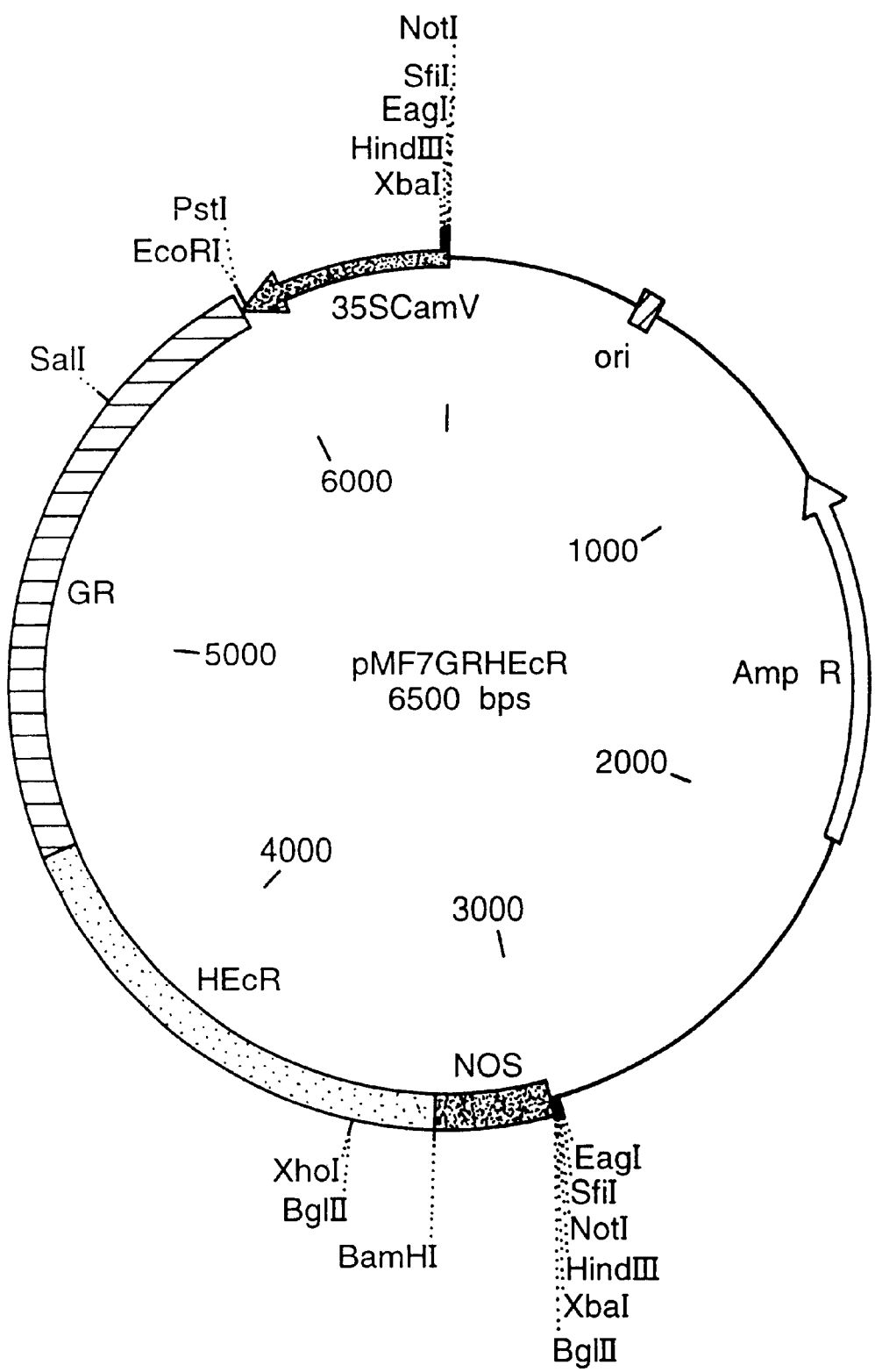
FIG. 23 shows a plasmid map of the tobacco expression vector containing the chimeric glucocorticoid Heliothis ecdysone receptor, pMF7GRHEcR.

The vector produced is a derivative of pMF6. pMF6GREcRS was restriction enzyme digested with PstI to produce 3 fragments namely, 3.4(Adh Intronless pMF6), 3.2(GREcRS) and 0.5(Adh intron I) kb). Isolation and religation of the 3.4 and 3.2 kb fragments resulted in pMF7GREcRS (FIG. 22). pMF7GREcRS was restriction enzyme digested with EcoRI/SacI resulting in the 3.4 kb pMF7 EcoRI/SacI vector which when isolated and purified was ligated to a 1.5 kb EcoRI/XhoI N-terminal end of the glucocorticoid receptor and the 1.2 kb SalI/SacI Heliothis ecdysone C-terminal end sequences to produce pMF7GRHEcR (FIG. 23).

Reporter Plasmid

The reporter plasmids constructed for the maize transient experiments were the same as those used without alteration in the tobacco leaf protoplast transient expression experiments.

Results—Chimeric Ecdysone Effector Constructs Mediate Inducible Expression in Tobacco Transient Protoplast Assays Experiments were performed to demonstrate that the effector plasmid pMF6GRHEcR can confer chemical dependant inducible expression on the reporter p221.9GRE6 in tobacco mesophyll protoplasts.

Figure 24:
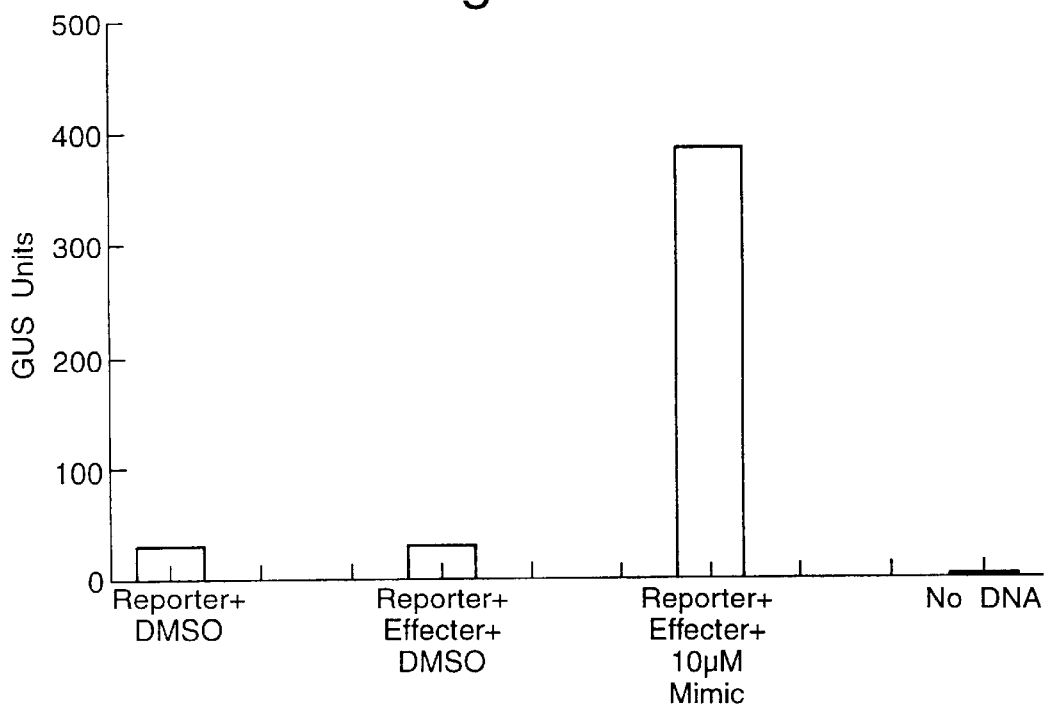
FIG. 24 shows a graph which shows the effect of RH5992 in Tobacco mesophyll protoplasts transformed with pMF6GRHEcR (Effector) and p221.9GRE6 (reporter)

FIG. 24 shows that reporter (p221.9GRE6) alone or reporter plus effector (pMF7GRHEcR) with no activating chemical, gave no significant expression in tobacco protoplasts. When reporter plus effector were co-transformed into tobacco protoplasts in the presence of 10 μM RH5992, a significant elevation of marker gene activity was observed. These data show a chimeric ecdysone effector construct, containing the Heliothis ligand binding domain can confer non-steroidal ecdysteroid dependant expression on reporter gene constructs in both monocotyledonous and dicotyledonous species.

EXAMPLE V

Chimeric Activity in Mammalian Cells

Figure 25:
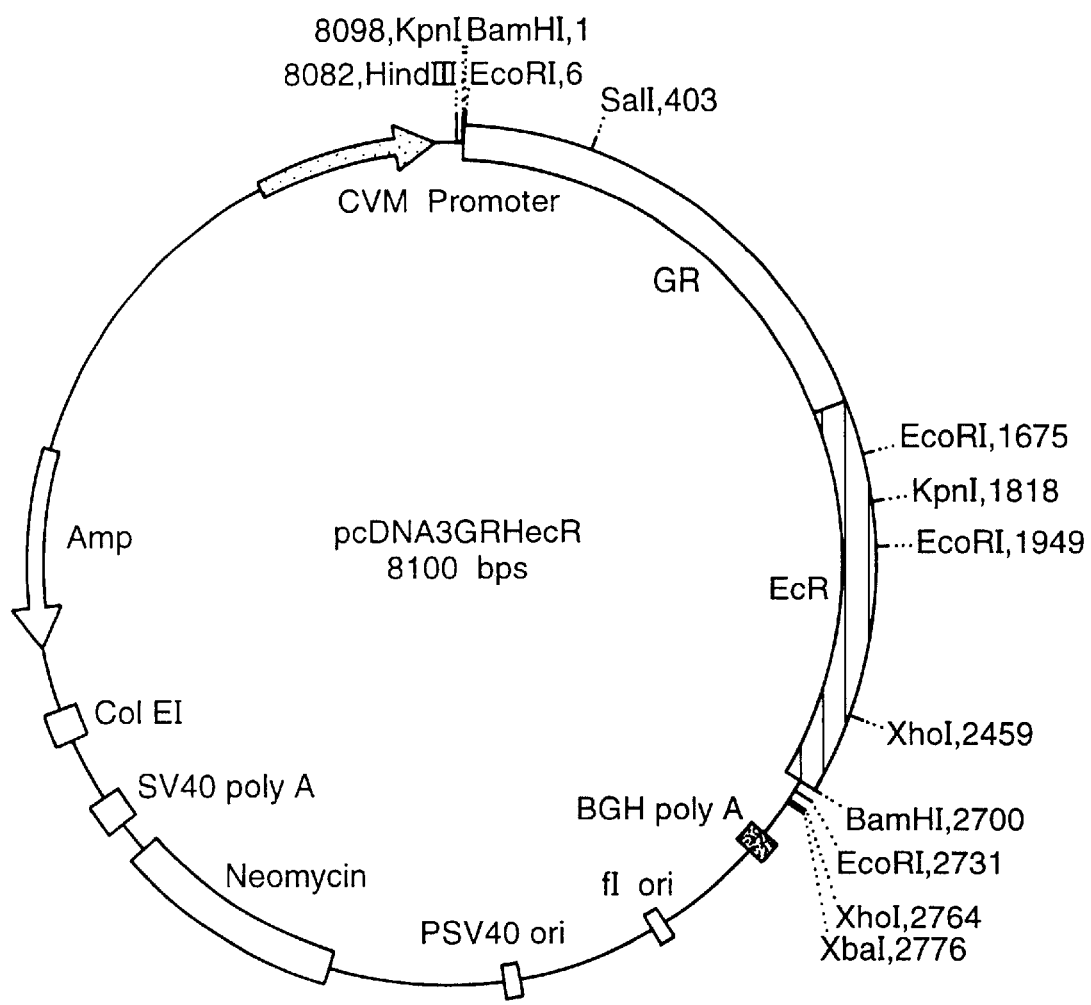
FIG. 25 shows a plasmid map of the mammalian expression vector containing the chimeric glucocorticoid/Heliothis ecdysone receptor, pcDNA3GRHEcR.

Effector Constructs (i) Construction of Glucocorticoid/Heliothis Ecdysone Chimeric Receptor The mammalian expression vector used in this experiment was pcDNA3 (Invitrogen). The GRHEcR 2.7 kb BamHI DNA fragment (isolated from pMF6GRHEcR) was introduced into the pcDNA3 BamHI vector. The recombinants were oriented by restriction enzyme mapping. The DNA sequence of the junctions was determined to ensure correct orientation and insertion (pcDNA3GRHEcR, FIG. 25).

Reporter Construct

The reporter plasmid for mammalian cell system was produced by taking pSWBGAL plasmid and replacing the CRESW SpeI/ClaI fragment for a synthetic 105 bp DNA fragment containing 4 copies of the glucocorticoid response element (GRE) and flanked by SpeI at the 5' end and AflII at the 3' end.

The oligonucleotides were synthesised using the sequences: GREspeI 5'ctagttgtacaggatgttctagctactc-gagtagctagaacatcctgtacagtcgagtagctagaacatcctgtacagtcgagtagctagaacatcctgtacac 3' (SEQ ID NO: 49) GREafl2 5'ttaagtgtacaggatgttctagctactcgactgtacaggatgttctagctactc-gactgtacaggatgttctagctactcgagtagctagaacatcctgtacaa 3' (SEQ ID NO: 50).

Figure 26:
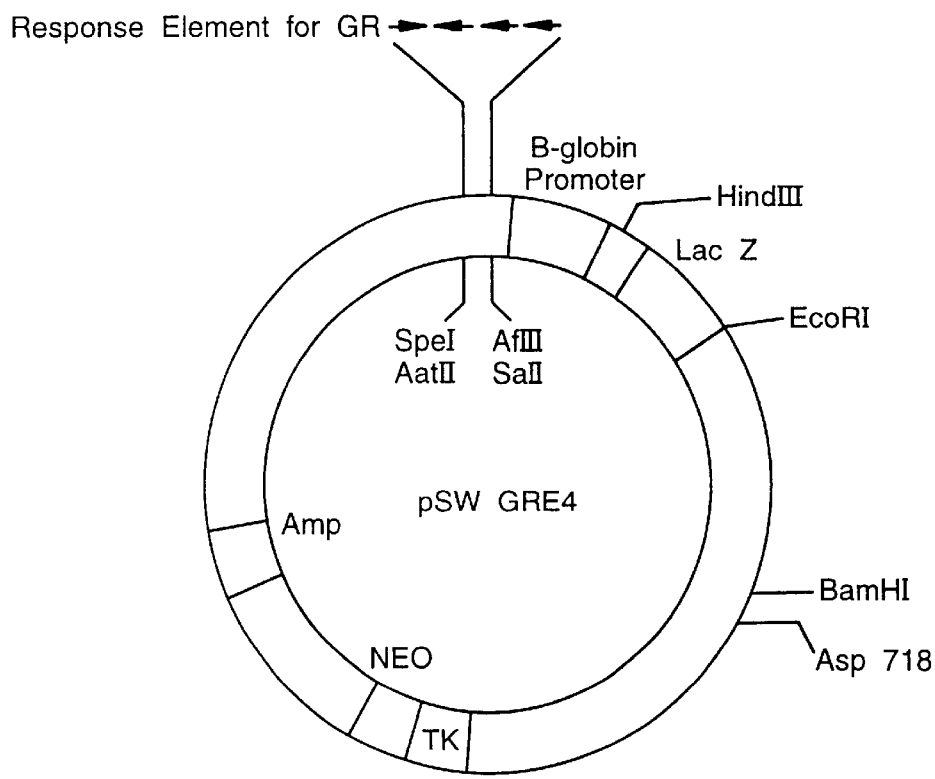
FIG. 26 shows a plasmid map of the reporter plasmid pSWGRE4.

The two oligonucleotides were purified annealed and ligated to pSWBGAL SpeI/AflII to produce pSWGRE4 (FIG. 26).

Figure 27:
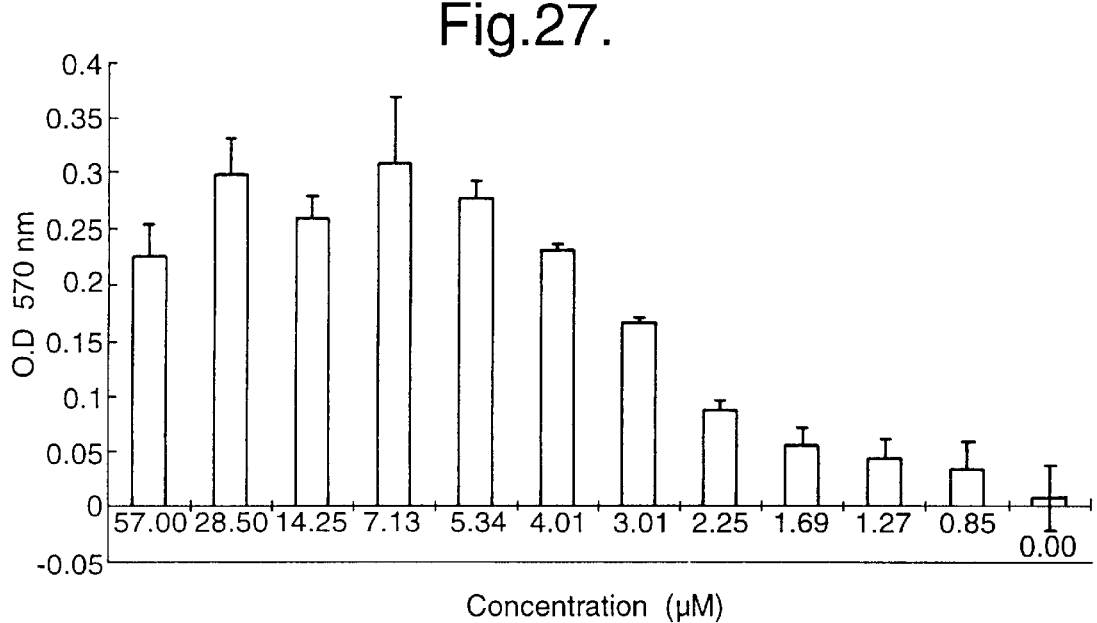
FIG. 27 shows a graph which shows a RH5992 dose response curve of CHO cells transfected with pcDNA3GRHEcR and pSWGRE4.
Figure 28:
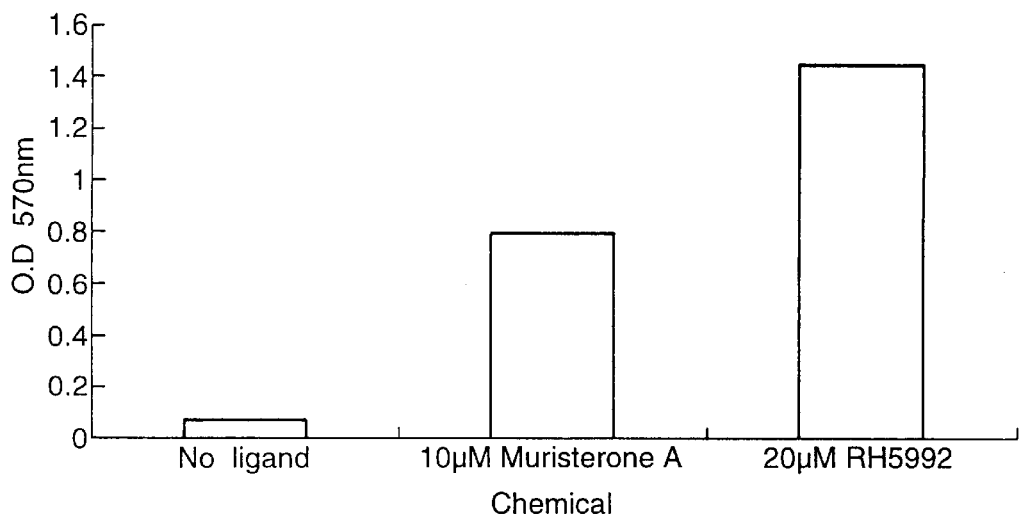
FIG. 28 shows a graph which shows the effect of Muristerone A and RH5992 on HEK293 cells co-transfected with pcDNA3GRHEcR and pSWGRE4.

Results—Chimeric HEcR Drives Transient Reporter Gene Expression in Mammalian Cells No expression was detected when a reporter gene construct pSWGRE4, comprising of a minimal β-globin promoter containing four copies of the glucocorticoid response element, fused to a β-galactosidase reporter gene, was introduced into CHO cells. Similarly, no expression was detected when pSWGRE4 and an effector plasmid pCDNA3GRHEcR, containing the transactivation and DNA binding domain from the glucocorticoid receptor and the ligand binding domain from the Heliothis ecdysone receptor, under the control of the CMV promoter were co-transformed into CHO-K1 or HEK293 cells. When co-transformed CHO (FIG. 27) and HEK293 cells (FIG. 28) were incubated in the presence of the non-steroidal ecdysone agonists RH5992 (mimic), significant chemical induced reporter gene activity was observed. Equally, induction of reporter activity was observed when HEK293 cells transfected with pcDNA3GRHEcR and reporter were treated with Muristerone A (FIG. 28).

EXAMPLE VI

Screening System Allows New Chemical Activators and Modified Ligand Binding Domains to be Tested in Mammalian Cells The basis of a screening system are in place after the demonstration that the chimeric receptor was activated in the presence of RH5992. A screen was carried out using CHO cells transiently transfected with both pSWGRE4 (reporter) and pcDNA3GRHEcR (effector) constructs. In the first instance 20 derivatives compounds of RH5992 were screened. It was observed that 7 out of the 20 compounds gave an increased reporter gene activity compared to untreated cells. A second screen was carried out in which 1000 randomly selected compounds were applied to transiently transfected CHO cells. Two compounds were found to activate reporter gene activity above that from the untreated controls. The second screen suggest that this cell based assay is a robust and rapid way to screen a small library of compounds, where a thousand compounds can be put through per week.

EXAMPLE V

Stably Transformed Tobacco Plants

Stable Tobacco Vectors

The components of the stable Tobacco vectors were put together in pBluescript prior to transfer into the binary vector. The production of stable transformed plants entails the production of a vector in which both components of the switch system (ie. effector and reporter) are placed in the same construct to then introduce into plants.

Figure 29:
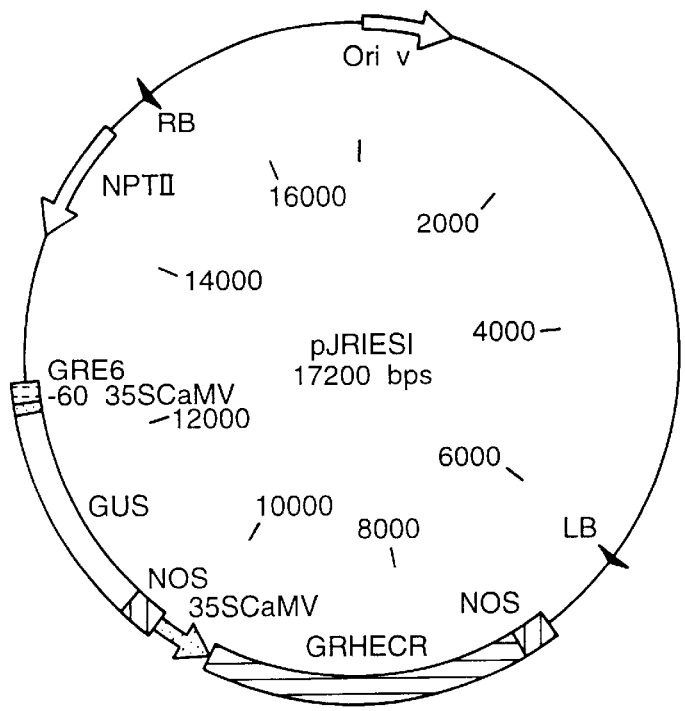
FIG. 29 shows a plasmid map of the binary vector ES1.
Figure 30:
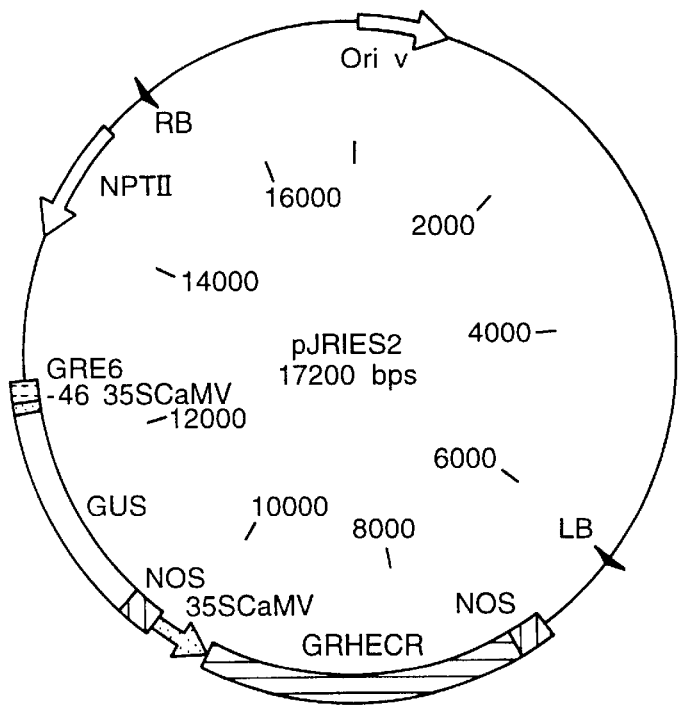
FIG. 30 shows a plasmid map of the binary vector ES2.
Figure 31:
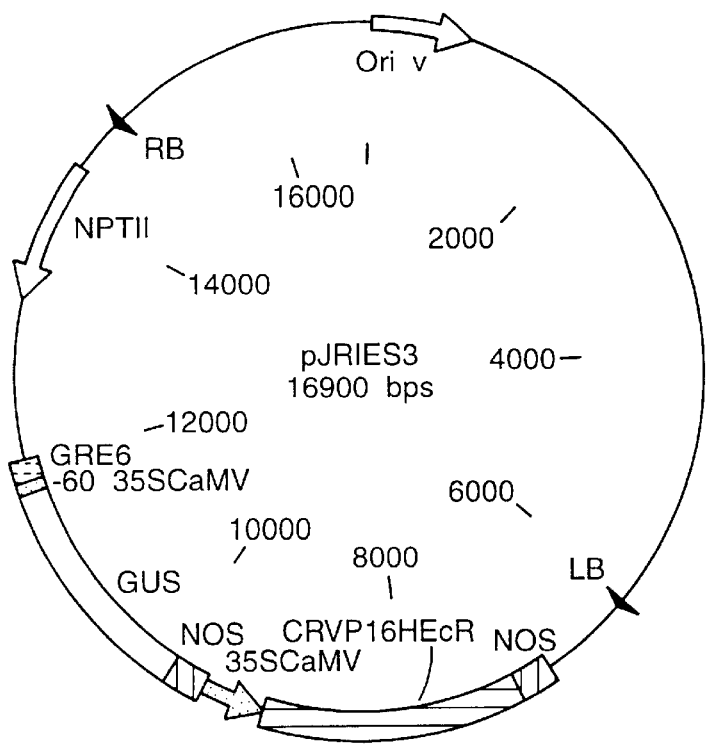
FIG. 31 shows a plasmid map of the binary vector ES3.
Figure 32:
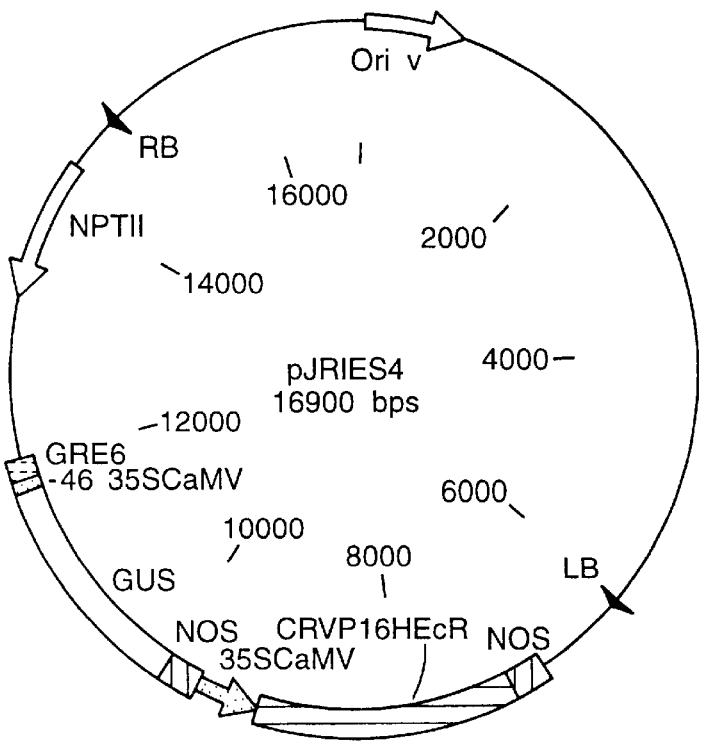
FIG. 32 shows a plasmid map of the binary vector ES4.

The methodology described below was used to produce four different stable Tobacco vectors. The method involves three steps:

1. pBluescript SK HindIII/EcoRI vector was ligated to either GRE6-4635SCaMVGUSNOS HindIII/EcoRI (from p221.10GRE6) or GRE6-6035SCaMVGUSNOS HindIII/EcoRI (from p221.9GRE6) resulting in plasmid pSK-46 and pSK-60.
2. This step involves the addition of the chimeric receptor (35SGRHEcRNOS or 35SGRVP16HEcRNOS) to pSK-60 or pSK-46. Thus a pSK-60 (or pSK-46) XbaI vector was ligated with either the 3.4kb 35SGRHEcRNOS XbaI or the 3.0 kb 35SGRVP16HEcRNOS XbaI DNA fragment to produce pSKES1 (pSKGRE6-6035SCaMVGUSNOS-35SGRHEcRNOS), pSKES2 (pSKGRE6-4635SCaMVGUSNOS-35SGRHEcRNOS), pSKES3 (pSKGRE6-6035SCaMVGUSNOS-35SGRVP16HEcRNOS) and pSKES4 (pSKGRE6-4635SCaMVGUSNOS-35SGRVP16HEcRNOS).
3. Transfer from pBluescript based vectors to binary vectors. The transfer of the ES 1 (FIG. 29) ES2 (FIG. 30), ES3 (FIG. 31) or ES4 (FIG. 32) DNA fragments into the binary vector JR1 involves five steps:
   (i) Restriction enzyme digestion of pSKES1 (ES2, ES3, and ES4) with ApaI and NotI to liberate the insert from the vector pBluescript.
   (ii) The two DNA fragments were BamHI methylated for 2 hours at 37° C. in TRIS-HCl, MgCl, 80 uM SAM (S-adenosylmethionine) and 20 U of BamHI methylase. (iii) Ligate a ApaI/NotI linker onto the fragment. The linker was designed to have an internal BamHI site: ApaBNot1 5' cattggatccttagc 3' (SEQ ID NO: 52) and ApaBNot2 5' ggccgctaaggatccaatgggcc 3' (SEQ ID NO: 52).
   (iv) Restriction enzyme digest the protected and linkered fragment with BamHI and fractionate the products on a 1%(w/v) Agarose gel. The protected DNA fragment (5.5 kb) was cut out of the gel and purified.
   (v) A ligation of JRI BamHI vector with the protected band was carried out to produce JRIES1 (JRIES2, JRIES3 or JRIES4). The DNA of the recombinant was characterised by restriction mapping and the sequence of the junctions determined.

The plant transformation construct pES1, containing a chimeric ecdysone receptor and a reporter gene cassette, was transferred into Agrobacterium tumefaciens LBA4404 using the freeze/thaw method described by Holsters et al. (1978). Tobacco (Nicotiana tabacum cv Samsun) transformants were produced by the leaf disc method (Bevan, 1984). Shoots were regenerated on medium containing 100 mg/l kanamycin. After rooting, plantlets were transferred to the glasshouse and grown under 16 hour light/8 hour dark conditions.

Results—Chimeric Ecdysone Effector Constructs Mediate Inducible Expression in Stably Tobacco Plants Transgenic tobacco plants were treated in cell culture by adding 100 μM RH5992 to MS media. In addition seedlings were grown hydroponically in the presence or absence of RH5992. In further experiments 5 mM RH5992 was applied in a foliar application to 8 week old glasshouse grown tobacco plants. In the three methods described uninduced levels of GUS activity were comparable to a wild type control, while RH5992 levels were significantly elevated.

Ecdysone Switch Modulation and Optimisation

EXAMPLE VIII

Yeast Indicator Strains for Primary Screen of Chemical Libraries

A set of yeast indicator strains was produced to use as a primary screen to find chemicals which may be used in the gene switch. The properties of the desired chemicals should include high affinity resulting in high activation but with different physico-chemical characteristics so as to increase the scope of application of the technology. Moreover, the production of this strain also demonstrates the generic features of this switch system.

Effector Vector

A base vector for yeast YCp15Gal-TEV-112 was generated containing:

Backbone—a modified version of pRS315 (Sikorski and Hieter (1989) Genetics 122, 19–27)-a shuttle vector with the LEU2 selectable marker for use in yeast;

ADH1 promoter (BamHI- Hind III fragment) and ADH1 terminator (Not I-Bam HI fragment) from pADNS (Colicelli et al PNAS 86, 3599–3603);

DNA binding domain of GAL4 (amino acids 1–147; GAL4 sequence is Laughon and Gesteland 91984) Mol. Cell Biol. 4, 260–267) from pSG424 (Sadowski and Ptashne (1989) Nuc. Acids Res. 17, 7539);

Activation domain—an acidic activation region corresponding to amino acids 1–107 of activation region B112 obtained from plasmid pB112 (Ruden et al (1991) Nature 350, 250–252).

The plasmid contains unique Eco RI, Nco I and Xba I sites between the DNA binding domain and activation domains.

Into this vector a PCR DNA fragment of the Heliothis ecdysone receptor containing the hinge, ligand binding domains and the C-terminal end was inserted. The 5' oligonucleotide is flanked by an NcoI restriction recognition site and begins at amino acid 259: HecrNcoI 5' aattccatggtac-gacgacagtagacgatcac 3' (SEQ ID NO: 65).

The 3' oligonucleotide is flanked by an XbaI site and encodes for up to amino acid 571: HecRXbaI 5' ctgaggtcta-gagacggtggcgggcggcc 3' (SEQ ID NO: 53).

Figure 33:
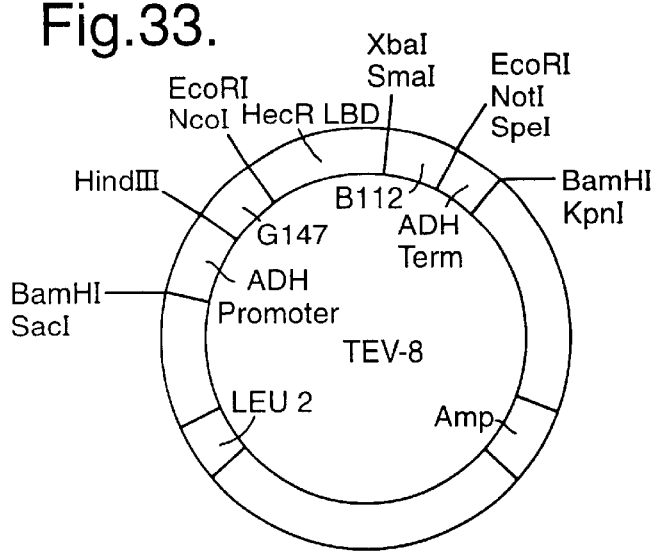
FIG. 33 shows a plasmid map of the effector construct TEV-B112 made to express the HEcR ligand binding domain in yeast.
Figure 34:
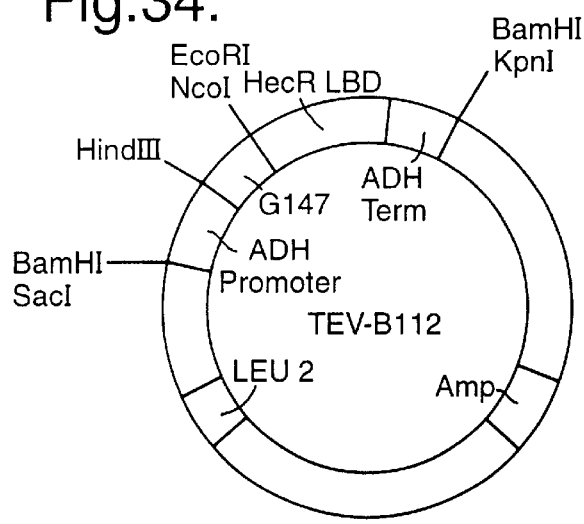
FIG. 34 shows a plasmid map of the effector construct TEV8 made to express the HEcR ligand binding domain in yeast.
Figure 35:
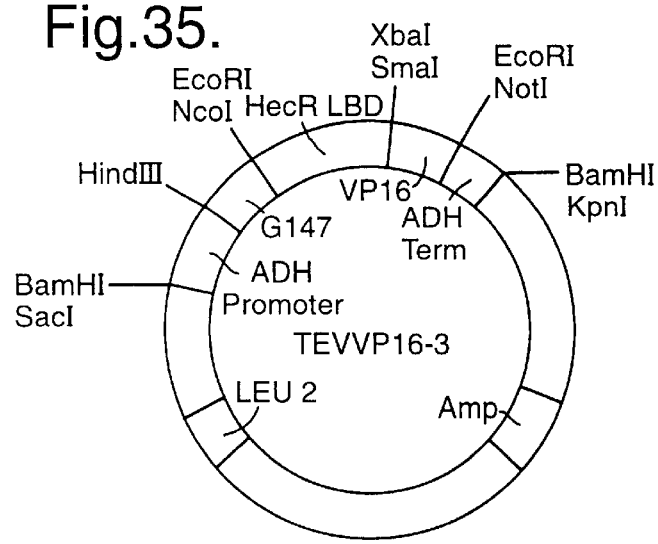
FIG. 35 shows a plasmid map of the effector construct TEVVP16-3 made to express the HEcR ligand binding domain in yeast.

The PCR was carried out using vent polymerase with the conditions described in Example IA. The fragment was restriction enzyme digested with NcoI and XbaI purified and ligated into YCp15GALTEV112 NcoI/XbaI vector to produce YGALHeCRB112 or TEV-B112 (FIG. 34). In order to reduce constitutive activity of the YGALHeCRB112 plasmid a YGALHeCR plasmid was produced in which the B112 activator was deleted by restriction enzyme digesting YGALHeCRB112 with XbaI/SpeI followed by ligation of the resulting vector (ie. SpeI and XbaI sites when digested produce compatible ends)(TEV-8, FIG. 33). An effector plasmid was constructed whereby the B112 transactivating domain was excised from YGalHecRB112 with XbaI and replaced with the VP16 transactivation domain DNA fragment (encoding amino acids 411 and 490 including the stop codon). The resulting vector was named YGalHecRVP16 or TEVVP16-3 (FIG. 35).

Reporter Construction for Yeast

The S. cerevisiae strain GGY1::171 (Gill and Ptashne (1987) Cell 51, 121–126), YT6:: 171 (Himmelfarb et al (1990) Cell 63, 1299-1309) both contain reporter plasmids consisting of the GALA-responsive GAL1 promoter driving the E. coli B-galactosidase gene. These plasmids are integrated at the URA3 locus. The reporter strain YT6::185 contains the reporter plasmid pJP185 (two synthetic GAL4 sites driving the B-galactosidase gene) integrated at the URA3 locus of YT6 (Himmelfarb et al). (Note- the parental strains YT6 and GGY1 have mutations in the GALA and GAL80 genes, so the reporter genes are inactive in the absence of any plasmids expressing GAL4 fusions).

Yeast Assay

Standard transformation protocols (Lithium acetate procedure) and selection of colonies by growth of cells on selective media (leucine minus medium in the case of the YCp15Gal-TEV-112 plasmid)- as described in Guthrie and Fink)1991) Guide to Yeast Genetics and Molecular Biology: Methods in Enzymology Vol. 194 Academic Press) and the reporter gene assay is a modification of that described in Ausabel et al (1993) Current Protocols in Molecular Biology (Wiley) Chapter 13).

Results—Automated Screening System Allows New Chemical Activators and Modified Ligand Binding Domains to be Tested in Yeast An effector vector pYGALHEcRB112 has been generated containing a GALA DNA binding domain, a B112 activation domain and the ligand binding region from Heliothis virescens. In combination with a GAL reporter vector, pYGA-LHEcRB112 form the basis of a rapid, high throughput assay which is cheap to run. This cell-based assay in yeast (Saccharomyces cerevisiae) will be used to screen for novel non-steroidal ecdysone agonists which may of commercial interest as novel insecticides or potent activators of the ecdysone gene switch system. The demonstration of an efficient system to control gene expression in a chemical dependant manner, forms the basis of an inducible system for peptide production in yeast.

The yeast screening system forms the basis of a screen for enhanced ligand binding using the lac Z reporter gene vector to quantitatively assay the contribution of mutation in the ligand binding domain. Alternatively, enhanced ligand binding capabilities or with a selection cassette where the lac Z reporter is replaced with a selectable marker such as uracil (URA 3), tryptophan (Trp1) or leucine (Leu2), and histidine (His). Constructs based on pYGALHEcRB112 with alterations in the ligand binding domain are grown under selection conditions which impair growth of yeast containing the wild type ligand binding domain. Those surviving in the presence of inducer are retested and then sequenced to identify the mutation conferring resistance.

EXAMPLE IX

Optimisation of Chimeric Receptor Using a Strong Transactivator

Construction of Mammalian Expression Plasmid with Chimeric Receptor Containing Herpex Simplex VP16 Protein Sequences The construction of this chimeric receptor is based on replacing the sequences encoding for the glucocorticoid receptor transactivating domain with those belonging to the VP16 protein of Herpex simplex. Thus PCR was used to generate three fragments all to be assembled to produce the chimeric receptor. The PCRs were carried out as described in Example II, iii. The first fragment includes the Kozak sequences and methionine start site of the glucocorticoid receptor to amino acid 152 of the glucocorticoid receptor. The oligonucleotides used for the generation of this fragment included an EcoRI site at the 5' end: GR1A 5' atat-gaattccaccatggactccaaagaatc 3' (SEQ ID NO: 54) and at the 3' end a NheI restriction enzyme recognition site: GR1B 5' atatgctagctgtgggggcagcagacacagcagtgg 3' (SEQ ID NO: 55).

The second fragment also belongs to the glucocorticoid receptor and begins with a NheI site in frame with amino acid 406: GR2A 5'atatgctagctccagctcctcaacagcaacaac 3' (SEQ ID NO: 56) and ends with a XhoI site at amino acid 500: GR2B 5'atatctcgagcaattccttttattttttc 3' (SEQ ID NO: 57).

The two fragments were introduced into pSKEcoRI/SacI in a ligation containing GR1A/B EcoRI/NheI, GR2A/B NheI/XhoI and HEcR SalI/SacI (from pSKHEcRDEF) to yield pSKGRDHEcR. The GR sequences and junctions of the ligation were found to be mutation free.

The third fragment to be amplified was a sequence between amino acid 411 to 490 of the herpes simplex VP16 protein. The amplified fragment was flanked with SpeI recognition sites. SpeI produces compatible ends to those of NheI sites. The oligonucleotides used: VP16C 5' attactagt-tctgcggccccccccgaccgat 3' (SEQ ID NO: 58) and VP16E 5' aattactagtcccaccgtactcgtcaattcc 3' (SEQ ID NO: 59) produced a 180 bp fragment which was restriction enzyme digested with SpeI and introduced into pSKGRΔHEcR NheI vector to produce pSKGRVP16HEcR. The DNA from the latter was sequenced and and found to be mutation free, the junctions were also shown to be in frame with those of the glucocorticoid receptor.

Figure 36:
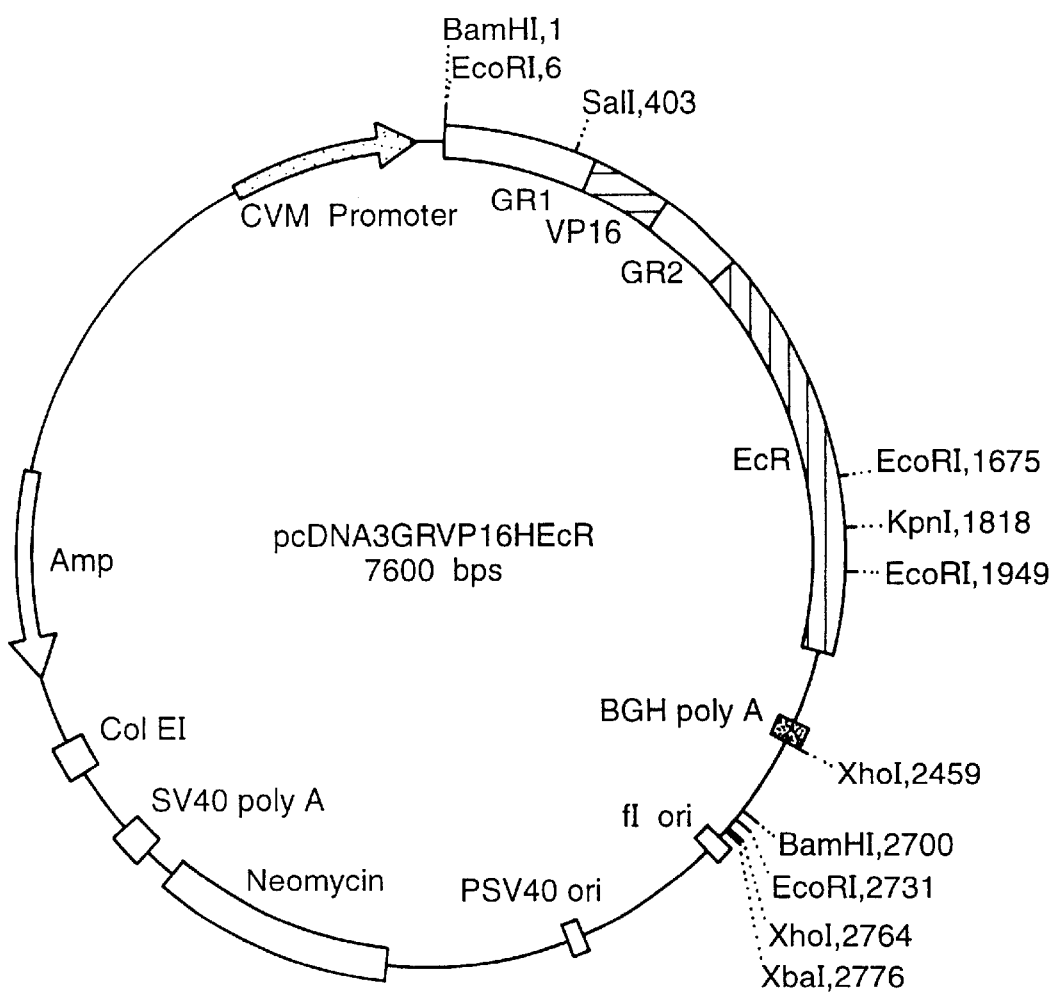
FIG. 36 shows a plasmid map of the mammalian expression vector containing the chimeric glucocorticoid VP16/Heliothis ecdysone receptor, pcDNA3GRVP16HEcR.

The 2.2 kb EcoRV/NotI GRVP16HEcR fragment was introduced into a pcDNA3 EcoRV/NotI vector resulting in pcDNA3GRVP16HEcR (FIG. 36).

Figure 37:
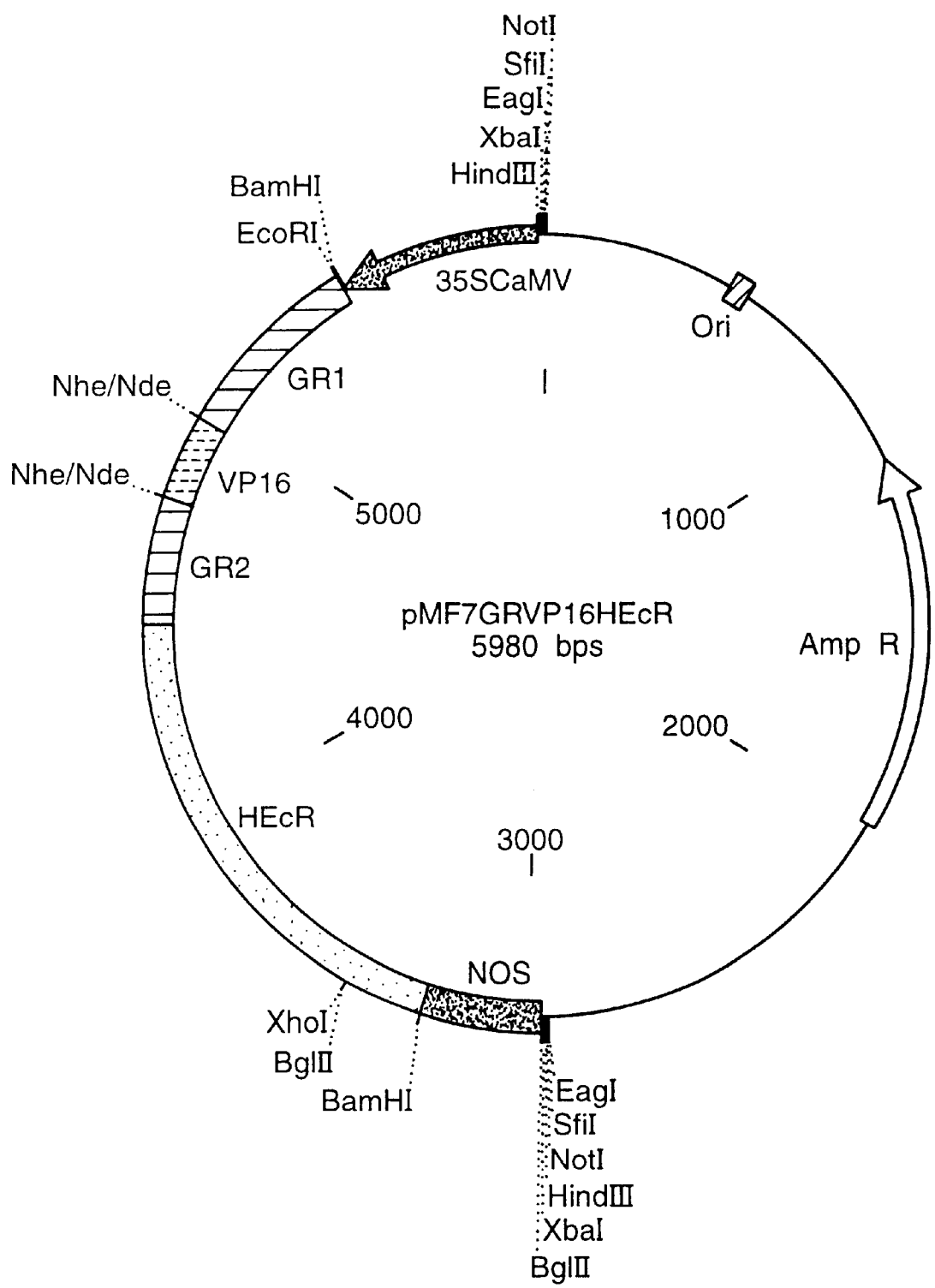
FIG. 37 shows a plasmid map of the maize expression vector containing the chimeric glucocorticoid VP16/Heliothis ecdsysone receptor, pMF6GRVP16HEcR.
Figure 38:
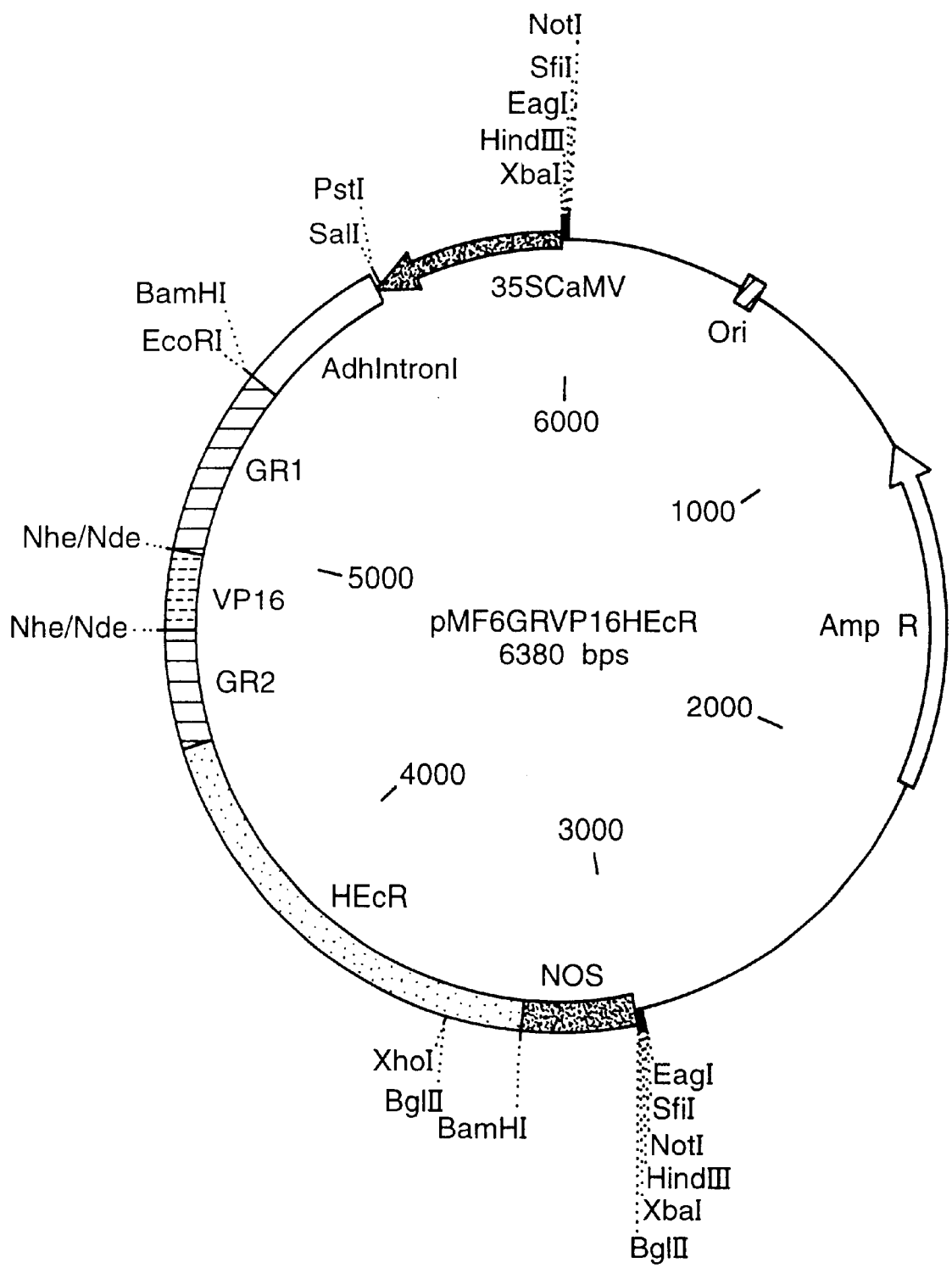
FIG. 38 shows a plasmid map of the maize expression vector containing the chimeric glucocorticoid VP16/Heliothis ecdsysone receptor, pMF7GRVP16HEcR.

Construction of Plant Transient Expression Effector Plasmids Containing the Chimeric Receptor with VP16 Sequences The same procedure was carried out to clone the GRVP16HeCR DNA fragment into tobacco(pMF7b) and maize(pMF6) expression vectors. A 2.2 kb BamHI DNA fragment was isolated from pcDNA3GRVP16HeCR and ligated in to the pMF6 BamHI (or pMF7b BamHI) vector to produce pMF6GRVP16HeCR (FIG. 37) (or pMF7GRVP16HeCR) (FIG. 38).

Results—Addition of Strong Activation Domains Enhance Ecdysone Switch System

Figure 39:
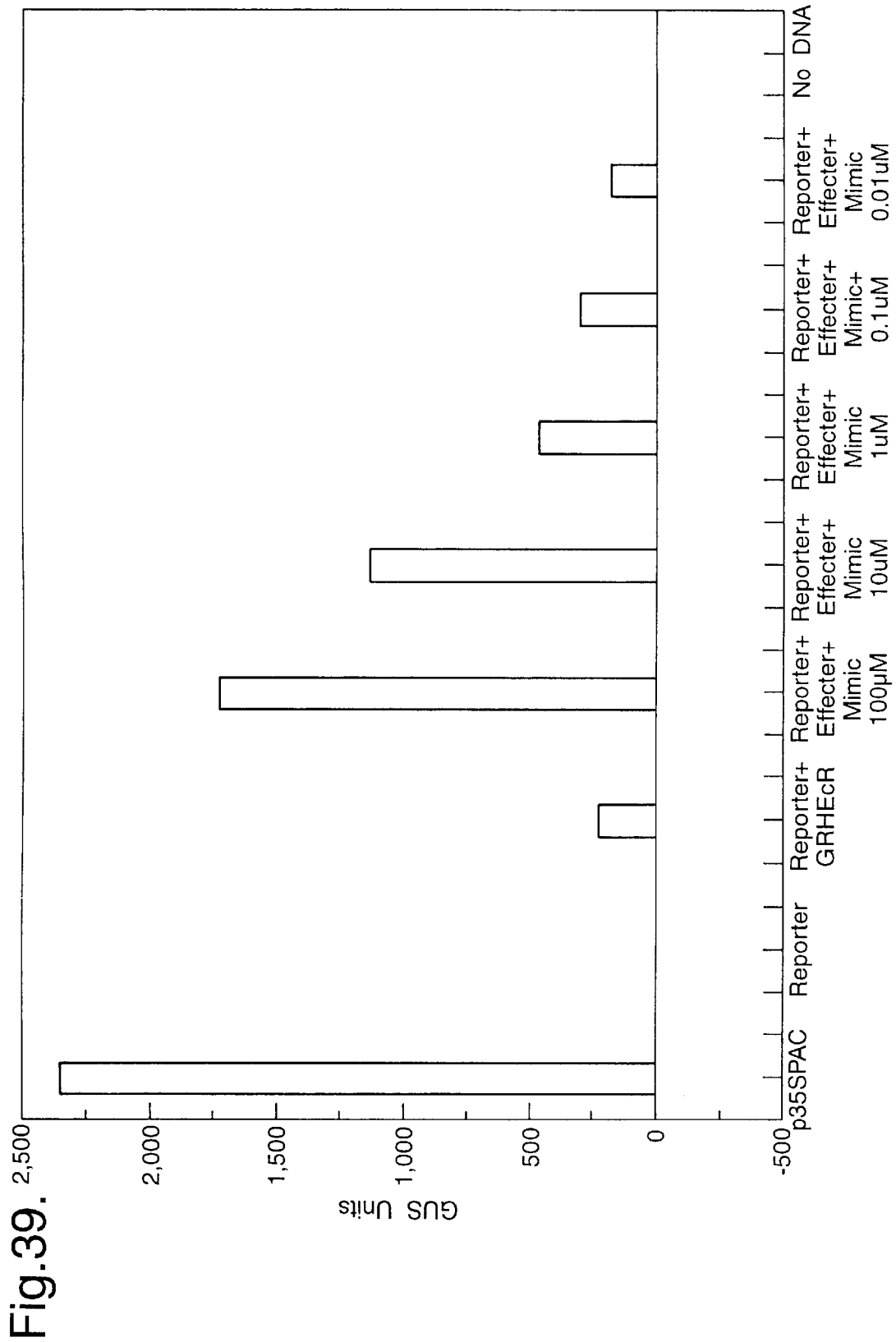
FIG. 39 shows a graph which shows the effect of RH5992 in Maize AXB protoplasts transformed with pMF6GRVP16HEcR (effector) and p221.9GRE6 (reporter)

The VP16 transactivation domain from herpes simplex virus has been added to a maize protoplast vector pMF6GRHEcR to generate the vector pMF6GRVP16HEcR. When co-transformed into maize protoplasts with the reporter construct p221.9GRE6, in the presence of 100 μM RH5992, enhanced levels of expression were seen over pMF6GRHEcR. FIG. 39, shows that RH5992 is able to induce GUS levels comparable to those observed with the positive control (p35SCaMVGUS), moreover, a dose response effect is observable.

VP16 enhanced vectors (pES3 and pES4) have been generated for stable transformation of tobacco. Following transformation transgenic progeny containing pES3 and pES4, gave elevated GUS levels following treatment with RH5992, relative to comparable transgenic plants containing the non-VP16 enhanced vectors pES 1 and pES2.

An enhanced mammalian vector pcDNA3GRVP16HEcR was prepared for transient transfection of mammalian cell lines. Elevated reporter gene activities were obtained relative to the effector construct (pCDNA3GRHEcR) without the VP16 addition.

"Acidic" activation domains are apparently "universal" activators in eukaryotes (Ptashne (1988) Nature 335 683–689). Other suitable acidic activation domains which have been used in fusions are the activator regions of GAL4 itself (region I and region II; Ma and Ptashne (Cell (1987) 48, 847–853), the yeast activator GCN4 (Hope and Struhl (1986) Cell 46, 885–894) and the herpes simplex virus VP16 protein (Triezenberg et al (1988) Genes Dev. 2, 718–729 and 730–742).

Other acidic and non-acidic transcriptional enhancer sequences for example from plant fungal and mammalian species can be added to the chimeric ecdysone receptor to enhance induced levels of gene expression.

Chimeric or synthetic activation domains can be generated to enhance induced levels of gene expression.

EXAMPLE X

Optimisation by Replacement of Heliothis Ligand Binding Domain in Chimeric Effector for that of an Ecdysone Ligand Binding Domain of Another Species Mutagenesis of the ecdysone ligand binding domain results in the increased sensitivity of the chimeric receptor for activating chemical. This can be achieved by deletions in the ligand binding domain, use of error prone PCR (Caldwell et al., PCR Meth. Applic 2, 28–33 1992), and in vitro DNA shuffling PCR (Stemmer, Nature 370, 389–391 1994). To enhance the efficacy of the listed techniques we have developed a screening system for enhanced levels of induced expression (see below).

An alternative strategy to the mutation of a known ligand binding domain is to identify insect species which are particularly sensitive to ecdysteroid agonists. For example *Spodoptera exigua* is particularly sensitive to RH 5992. To investigate the role of the ecdysone receptor ligand binding domain in increased sensitivity to RH5992 we have isolated corresponding DNA sequences from of *S. exigua* (FIG. 40, Sequence ID No. 6). FIG. 41, Sequence ID No. 7 shows a protein alignment of the hinge and ligand binding domains of the *Heliothis virescens* and *Spodoptera exigua* ecdysone receptors. The protein sequence between the two species is well conserved.

Results—Manipulation of the Ligand Binding Domain Leads to Enhanced Induced Expression Isolation of an ecdysone ligand binding domain from another lepidopteran species was carried out by using degenerate oligonucleotides and PCR of first strand cDNA (Perkin Elmer, cDNA synthesis Kit) of the chosen species. The degenerate oligonucleotides at the 5' end were HingxhoA and B and at the 3' end ligandxA/B

```
HingxhoA 5' attgctcgagaaagiccigagtgcgtigticc 3' (SEQ ID NO:60)
                       a t HingxhoB 5' attgctcgagaacgiccigagtgtgtigticc 3' (SEQ ID NO:61)
                       a c LigandxA 5' ttactcgagiacgtcccaiatctcttciaggaa 3' (SEQ ID NO:62)
                    a      t c    a ligandxB 5' ttactcgagiacgtcccaiatctcctciaagaa 3' (SEQ ID NO:63)
                    a      t t    a
```

RNA was extracted from 4th instar larvae of *Spodoptera exigua* since *Spodoptera exigua* appears to be more sensitive to RH5992 than Heliothis (Smagghe and Degheele, 1994). The first strand cDNA was used in PCR reactions under the following conditions 20 mM Tris-HCL (pH8.4), 50 mM KCl, 1.5 mM $MgCl_2$, 200 mM dNTPs (dATP,dCTP,dGTP and dTTP) and 0.02 U/ml Taq DNA polymerase and in the presence of 1ug of each Hinge (5'3') and Ligand (5'3') oligonucleotides. The PCR cycling conditions were 94° C. for 1 minute, 60° C. for 2 minutes and 72° C. for 1 minute and 35 cycles were carried out. A sample of the completed reaction was fractionated in a 1% agarose (w/v) 1×TBE gel, and the resulting 900 bp fragment was subcloned into pCRII vector (Invitrogen). The resulting clone (pSKSEcR 1-10) were further characterised and sequenced.

EXAMPLE X
Manipulation of Reporter Gene Promoter Regions can Modulate Chemical Induced Expression The context of the effector response element in the reporter gene promoter can be used to modulate the basal and induced levels of gene expression. Six copies of the glucorticoid response element were fused to 46 bp or 60 bp of the CaMV 35S promoter sequence. When used with the effector construct pMF7GRHEcRS the reporter gene construct containing 46 bp of the CaMV 35S promoter gave reduced basal and induced levels of GUS expression relative to the 60 bp reporter construct (FIG. 42).

Constructs for plant transformation (pES1 and ES2) have been generated to demonstrate the size of minimal promoter can be used to modulate the basal and induced levels of gene expression in plants.

The number and spacing of response elements in the reporter gene promoter can be adjusted to enhance induced levels of trans-gene expression.

The utility of a two component system (effector and reporter gene cassettes) allows the spatial control of induced expression. Trans-gene expression can be regulated in an tissue specific, organ specific or developmentally controlled manner. This can be achieved by driving the effector construct from a spatially or temporally regulated promoter.

REFERENCES

Allan, G. F., Tsai, S. Y., Tsai, M.-J. and O'Malley, B. W. (1992a) P.N.A.S. 89, 11750–11754.

Allan, G. F., Leng, X., Tsai, S. Y., Weigel, N. L., Edwards, D. P., Tsai, M.-J. and O'Malley, B. W. (1992b) J. Biol. Chem 267, 19513–19520.

Ashburner, M (1990) Cell 61, 1–3.

Beato, M. (1989) Cell 56, 335–344.

Carlberg, C., Bendik, I., Wyss, A., Meier, E., Sturzenbecker, L. J., Grippo, J. F. and Hunziker, W. (1993) Nature 361, 657–660.

Christopherson, K. S., Mark., M. R., Bajaj, V. and Godowski, P. J. (1992) P.N.A.S. 89, 6314–6318.

Evans, R. M. (1988) Science 240, 889–895.

Green, S. and Chambon, P. (1988) TIGs 11, 309–314.

Heyman, R. A., Mangelsdorf, D. J., Dyck, J. A., Stein, R. B., Eichele, G., Evans, R. M. and Thaller, C. (1992) Cell 68, 397–406.

Hirst,M. C., Bassett, J. H. D., Roche, A. and Davies, K. E. (1992) Trends in Genetics 8, 6–7.

Hogness, D. S., Talbot, W. S., Bender, M. T. and Koelle, M. (1992) X Ecdysone Workshop, Liverpool. Abstract.

Hollenberg, S. M., Weinberger, C., Ong, E. S., Cerelli, G., Oro, A., Lebo, R., Thompson, E. B., Rosenfeld, M. G. and Evans, R. M. (1985) Nature 318, 635–641.

Kliewer, S. A., Umesono, K., Mangeldorf, D. J. and Evans, R. M. (1992) Nature 355, 446–449.

Koelle, M. R., Talbot, W. S., Segraves, W. A., Bender, M. T., Cherbas, P. and Hogness, D. S. (1991) Cell 67, 59–77.

Krust et al, (1986) The EMBO Journal 5, 891–897.

Leid, M., Kastner, P., Lyons, R., Nakshatri, H., Saunders, M., Zacharewski, T., Chen, J-Y., Staud, A., Garnier, J-M., Mader, S. and Chambon, P. (1992a) Cell 68, 377–395.

Leid, M., Kastner, P and Chambon, P. (1992b) TIBs 17,427–433.

Mangelsdorf, D. J., Borgmeyer, V., Heymann, R. A., Zhou, J. Y., Ong, E. S., Oro, A. E., Kakizuka, A. and Evans, R. M. (1992) Genes and Development 6, 329–344.

Oro, A. E., Mckeown, M. and Evans, R. M. (1990) Nature 347, 298–301.

Riddihough, G. and Pelham, H. R. B. (1987) EMBO Journal 6, 3729–3734.

Segraves, W. A. (1991) Cell 67, 225–228.

Segraves, W. A. and Hogness, D. S. (1990) Genes and Development 4, 204–219.

Smagghe, G. and Degheele, D (1994) Pestic. Sci. 42, 85–92.

Stemmer, W. P. (1994) Nature 370, 389–391.

Thummel, C. S., Burtis, K. S. and Hogness, D. S. (1990) Cell 61, 101–111.

Vegeta, E., Allan, G. F., Schrader, W. T., Tsai, M-J., McDonnell, D. P. and O'Maley, B. W. (1992) Cell 69, 703–713

Yao, T. P., Segraves, W. A., Oro, A. E., Mckeown, M. and Evans, R. M. (1992) Cell 71, 63–72.

Yao, T-P., Forman, B. M., Jlang, Z., Cherbas, L., Chen, J-Don., Mckeown, M., Cherbas, P. and Evans, R. M. (1993) Nature 366, 476–479.

Yu, V. C., Delsert, C., Andersen, B., Holoway, J. M., Kim, S. Y., Boutin, J-M., Glass, C. K. and Rosenfeld, M. G. (1991) Cell 67, 1251–1266.

SEQUENCE LISTING

```
<160> NUMBER OF SEQ ID NOS:   65

<210> SEQ ID NO 1
<211> LENGTH: 116
<212> TYPE: DNA
<213> ORGANISM: Heliothis virescens

<400> SEQUENCE: 1
tgcgaggggt gcaaggagtt cttcaggcgg agtgtaacca aaaatgcagt g tacatatgc      60 aaattcggcc atgcttgcga aatggatatg tatatgcgga gaaaatgcca a gagta        116

<210> SEQ ID NO 2
<211> LENGTH: 1934
<212> TYPE: DNA
<213> ORGANISM: Heliothis virescens
```

<400> SEQUENCE: 2

```
tccactggtg ttttcaccac cacagaaaag gcctctgctc atttagaggg t ggtgctaag      60
aaggtcatca tctcctgctg cccagcgctg acccatgttc gtcgttggtg t caaccttga    120
agcagtatga cccctcttac aaggtcatct ccaacgcctc ctgcacaacc a actgcctcg    180
ctcctctcgc taaggtcatc catgacaact tcgagatcat tgaaggtctg a tgaccactg    240
tacacgccac cactgccacc cagaagacag tggatggacc ctctggtaaa c tgtggcgtg    300
atggccgtgg tgctcagcag aatatcattc cgcggaatt ccccagccgc a gctagctaa    360
cctgcagcag acacaacccc taccttccat gccgttacca atgccaccga c aacacccaa    420
atcagaaaac gagtcaatgt catcaggtcg tgaggaactg tctccagctt c gagtgtaaa    480
cggctgcagc acagatggcg aggcgaggcg gcagaagaaa ggcccagcgc c gaggcagca    540
agaagagcta tgtcttgtct gcggcgacag agcctccgga tatcactaca a cgcgctcac    600
atgtgaaggg tgtaaaggtt tcttcaggcg gagtgtaacc aaaaatgcag t gtacatatg    660
caaattcggc catgcttgcg aaatggatat ctatatgcgg agaaaatgtc a ggagtgtcg    720
gttgaagaaa tgtcttgcgg tgggcatgag gcccgagtgc gtggtgccgg a gaaccagtg    780
tgcaatgaaa cggaaagaga aaaggcgca gagggaaaaa gacaaattgc c cgtcagtac    840
gacgacagta gacgatcaca tgcctcccat catgcaatgt gaccctccgc c cccagaggc    900
cgctagaatt ctggaatgtg tgcagcacga ggtggtgcca cgattcctga a tgagaagct    960
aatggaacag aacagattga agaacgtgcc cccctcact gccaatcaga a gtcgttgat   1020
cgcaaggctc gtgtggtacc aggaaggcta tgaacaacct tccgaggaag a cctgaagag   1080
ggttacacag tcggacgagg acgacgaaga ctcggatatg ccgttccgtc a gattaccga   1140
gatgacgatt ctcacagtgc agctcatcgt agaattcgct aagggcctcc c gggcttcgc   1200
caagatctcg cagtcggacc agatcacgtt attaaaggcg tgctcaagtg a ggtgatgat   1260
gctccgagtg gctcggcggt atgacgcggc caccgacagc gtactgttcg c gaacaacca   1320
ggcgtacact cgcgacaact accgcaaggc aggcatggcg tacgtcatcg a ggacctgct   1380
gcacttctgt cggtgcatgt actccatgat gatggataac gtgcattatg c gctgcttac   1440
agccattgtc atcttctcag accggcccgg gcttgagcaa cccctgttgg t ggaggacat   1500
ccagagatat tacctgaaca cgctacgggt gtacatcctg aaccagaaca g cgcgtcgcc   1560
ccgcggcgcc gtcatcttcg gcgagatcct gggcatactg acggagatcc g cacgctggg   1620
catgcagaac tccaacatgt gcatctccct caagctgaag aacaggaagc t gccgccgtt   1680
cctcgaggag atctgggacg tggcggacgt ggcgacgacg cgacgccgg t ggcggcgga   1740
ggcgccggcg cctctagccc ccgccccgcc cgcccggccg cccgccaccg t ctagcgcgc   1800
ctcaggagag aacgctcata gactggctag ttttagtgaa gtgcacggac a ctgacgtcg   1860
acgtgatcaa cctatttata aggactgcga attttaccac ttaagagggc a cacccgtac   1920
ccgatttcgt acgg                                                      1934
```

<210> SEQ ID NO 3
<211> LENGTH: 2464
<212> TYPE: DNA
<213> ORGANISM: Heliothis virescens
<220> FEATURE:
<221> NAME/KEY: Unsure
<222> LOCATION: (2241)..(2241)
<223> OTHER INFORMATION: Unsure

<400> SEQUENCE: 3

```
cgctggtata acaacggacc attccagacg ctgcgaatgc tcgaggagag c tcgtctgag    60
gtgacgtcgt cttcagcact gggcctgccg ccggctatgg tgatgtcccc g gaatcgctc   120
gcgtcgcccg agatcggcgg cctggagctg tggggctacg acgatggcat c acttacagc   180
atggcacagt cgctgggcac ctgcaccatg gagcagcagc agcccagccg c agcagcag   240
ccgcagcaga cacaacccct accttccatg ccgttaccaa tgccaccgac a acacccaaa   300
tcagaaaacg agtcaatgtc atcaggtcgt gaggaactgt ctccagcttc g agtgtaaac   360
ggctgcagca cagatggcga ggcgaggcgg cagaagaaag cccagcgcc g aggcagcaa    420
gaagagctat gtcttgtctg cggcgacaga gcctccggat atcactacaa c gcgctcaca   480
tgtgaagggt gtaaaggttt cttcaggcgg agtgtaacca aaaatgcagt g tacatatgc   540
aaattcggcc atgcttgcga atggatatc tatatgcgga gaaaatgtca g gagtgtcgg   600
ttgaagaaat gtcttgcggt gggcatgagg cccgagtgcg tggtgccgga g aaccagtgt   660
gcaatgaaac ggaaagagaa aaaggcgcag agggaaaaag acaaattgcc c gtcagtacg   720
acgacagtag acgatcacat gcctcccatc atgcaatgtg accctccgcc c ccagaggcc   780
gctagaattc tggaatgtgt gcagcacgag gtggtgccac gattcctgaa t gagaagcta   840
atggaacaga acagattgaa gaacgtgccc cccctcactg ccaatcagaa g tcgttgatc   900
gcaaggctcg tgtggtacca ggaaggctat gaacaacctt ccgaggaaga c ctgaagagg   960
gttacacagt cggacgagga cgacgaagac tcggatatgc cgttccgtca g attaccgag  1020
atgacgattc tcacagtgca gctcatcgta gaattcgcta agggcctccc g ggcttcgcc  1080
aagatctcgc agtcggacca gatcacgtta ttaaaggcgt gctcaagtga g gtgatgatg  1140
ctccgagtgg ctcggcggta tgacgcggcc accgacagcg tactgttcgc g aacaaccag  1200
gcgtacactc gcgacaacta ccgcaaggca ggcatggcgt acgtcatcga g gacctgctg  1260
cacttctgtc ggtgcatgta ctccatgatg atggataacg tgcattatgc g ctgcttaca  1320
gccattgtca tcttctcaga ccggcccggg cttgagcaac cctgttggt g gaggacatc  1380
cagagatatt acctgaacac gctacggtgt acatcctga accagaacag c gcgtcgccc  1440
cgcggcgccg tcatcttcgg cgagatcctg gcatactga cggagatccg c acgctgggc  1500
atgcagaact ccaacatgtg catctccctc aagctgaaga acaggaagct g ccgccgttc  1560
ctcgaggaga tctgggacgt ggcggacgtg gcgacgacgg cgacgccggt g gcggcggag  1620
gcgccggcgc ctctagcccc cgccccgccc gcccggccgc ccgccaccgt c tagcgcgcc  1680
tcaggagaga acgctcatag actggctagt tttagtgaag tgcacggaca c tgacgtcga  1740
cgtgatcaac ctatttataa ggactgcgaa ttttaccact taagagggca c acccgtacc  1800
cgatttcgta cgtattcggt gaccgacgac gatgcagagc gtgtgtaatg t gaatatatg  1860
tgttgttgaa cgatttggag aatatatatt ggtgttgctg ttcgggcccg c acgccgtcg  1920
ccggtcggcg gcgatcgcgg cgcccgcggc ttcagttta tttcgtttac g actgagttg  1980
gtcactcgga tacgactgta tgataagact tcgttcgata agtacaccta c taaattaca  2040
catacgtacg tagcttacga gagttattag agacaaagaa tataagaaga a gatgtttct  2100
attgggtgaa aagttgatag ttatgtttat ttaccaaaat taacaataat a cgttgatta  2160
accttttcgag tataatattg tgatgagtcg tccgctgtcc acgtcgccgt c acatgtttg  2220
tttctgatgc acacgtgagg ngcgttatcg tgtttcatgg ttccatcgtc c tgtgcccgc  2280
gaccctcgac taaatgagta atttaattta ttgctgtgat tacatttaa t gtgttgatt  2340
```

-continued

| | | |
|---|---|---|
| atctaccata gggtgatata agtgtgtctt attacaatac aaagtgtgtg t cgtcgatag | 2400 | |
| cttccacacg agcaagcctt ttgtttaagt gatttactga catggacact c gacccggaa | 2460 | |
| cttc | 2464 | |

<210> SEQ ID NO 4
<211> LENGTH: 2745
<212> TYPE: DNA
<213> ORGANISM: Heliothis virescens
<220> FEATURE:
<221> NAME/KEY: Unsure
<222> LOCATION: (2522)..(2522)
<223> OTHER INFORMATION: Unsure

<400> SEQUENCE: 4

| | |
|---|---|
| actcgcgtgc tcttctcacc tgttgctcgg attgtgttgt actagaaaaa a gttgtcgcc | 60 |
| gctcgaacga gacttccgag tcctattgga ttgcacgaaa gtcgagacag t ggatagcga | 120 |
| ttcggtttcg tttgaacgtt gcgtagacga gtggtgcatg tccatgagtc g cgtttagat | 180 |
| agtttagtgc gaggaaaaag tgaagtgaaa gccttcctcg gaggatgtcc c tcggcgctc | 240 |
| gtggataccg gaggtgtgac acgctcgccg acatgagacg ccgctggtat a caacggac | 300 |
| cattccagac gctgcgaatg ctcgaggaga gctcgtctga ggtgacgtcg t cttcagcac | 360 |
| tgggcctgcc gccggctatg gtgatgtccc cggaatcgct cgcgtcgccc g agatcggcg | 420 |
| gcctggagct gtggggctac gacgatggca tcacttacag catggcacag t cgctgggca | 480 |
| cctgcaccat ggagcagcag cagccccagc cgcagcagca gccgcagcag a cacaacccc | 540 |
| taccttccat gccgttacca atgccaccga caacacccaa atcagaaaac g agtcaatgt | 600 |
| catcaggtcg tgaggaactg tctccagctt cgagtgtaaa cggctgcagc a cagatggcg | 660 |
| aggcgaggcg gcagaagaaa ggcccagcgc cgaggcagca agaagagcta t gtcttgtct | 720 |
| gcggcgacag agcctccgga tatcactaca acgcgctcac atgtgaaggg t gtaaaggtt | 780 |
| tcttcaggcg gagtgtaacc aaaaatgcag tgtacatatg caaattcggc c atgcttgcg | 840 |
| aaatggatat ctatatgcgg agaaaatgtc aggagtgtcg gttgaagaaa t gtcttgcgg | 900 |
| tgggcatgag gcccgagtgc gtggtgccgg agaaccagtg tgcaatgaaa c ggaaagaga | 960 |
| aaaggcgca gagggaaaaa gacaaattgc ccgtcagtac gacgacagta g acgatcaca | 1020 |
| tgcctcccat catgcaatgt gaccctccgc ccccagaggc cgctagaatt c tggaatgtg | 1080 |
| tgcagcacga ggtggtgcca cgattcctga atgagaagct aatggaacag a acagattga | 1140 |
| agaacgtgcc cccctcact gccaatcaga agtcgttgat cgcaaggctc g tgtggtacc | 1200 |
| aggaaggcta tgaacaacct tccgaggaag acctgaagag ggttacacag t cggacgagg | 1260 |
| acgacgaaga ctcggatatg ccgttccgtc agattaccga gatgacgatt c tcacagtgc | 1320 |
| agctcatcgt agaattcgct aagggcctcc cgggcttcgc caagatctcg c agtcggacc | 1380 |
| agatcacgtt attaaaggcg tgctcaagtg aggtgatgat gctccgagtg g ctcggcggt | 1440 |
| atgacgcggc caccgacagc gtactgttcg cgaacaacca ggcgtacact c gcgacaact | 1500 |
| accgcaaggc aggcatggcg tacgtcatcg aggacctgct gcacttctgt c ggtgcatgt | 1560 |
| actccatgat gatggataac gtgcattatg cgctgcttac agccattgtc a tcttctcag | 1620 |
| accggcccgg gcttgagcaa cccctgttgg tggaggagat ccagagatat t acctgaaca | 1680 |
| cgctacgggt gtacatcctg aaccagaaca gcgcgtcgcc ccgcggcgcc g tcatcttcg | 1740 |
| gcgagatcct gggcatactg acggagatcc gcacgctggg catgcagaac t ccaacatgt | 1800 |
| gcatctccct caagctgaag aacaggaagc tgccgccgtt cctcgaggag a tctgggacg | 1860 |

-continued

```
tggcggacgt ggcgacgacg gcgacgccgg tggcggcgga ggcgccggcg c ctctagccc       1920 ccgccccgcc cgcccggccg cccgccaccg tctagcgcgc ctcaggagag a acgctcata       1980 gactggctag ttttagtgaa gtgcacggac actgacgtcg acgtgatcaa c ctatttata       2040 aggactgcga attttaccac ttaagagggc acacccgtac ccgatttcgt a cgtattcgg       2100 tgaccgacga cgatgcagag cgtgtgtaat gtgaatatat gtgttgttga a cgatttgga       2160 gaatatatat tggtgttgct gttcgggccc gcacgccgtc gccggtcggc g gcgatcgcg       2220 gcgcccgcgg cttcagtttt atttcgttta cgactgagtt ggtcactcgg a tacgactgt       2280 atgataagac ttcgttcgat aagtacacct actaaattac acatacgtac g tagcttacg       2340 agagttatta gagacaaaga atataagaag aagatgtttc tattgggtga a agttgata        2400 gttatgttta tttaccaaaa ttaacaataa tacgttgatt aacctttcga g tataatatt       2460 gtgatgagtc gtccgctgtc cacgtcgccg tcacatgttt gtttctgatg c acacgtgag       2520 gngcgttatc gtgtttcatg gttccatcgt cctgtgcccg cgaccctcga c taaatgagt       2580 aatttaattt attgctgtga ttacatttta atgtgttgat tatctaccat a gggtgatat       2640 aagtgtgtct tattacaata caaagtgtgt gtcgtcgata gcttccacac g agcaagcct       2700 tttgtttaag tgatttactg acatggacac tcgacccgga acttc                       2745
```

<210> SEQ ID NO 5
<211> LENGTH: 575
<212> TYPE: PRT
<213> ORGANISM: Heliothis virescens

<400> SEQUENCE: 5

```
Met Ser Leu Gly Ala Arg Gly Tyr Arg Arg C ys Asp Thr Leu Ala Asp
1               5                   10                  15

Met Arg Arg Arg Trp Tyr Asn Asn Gly Gly P he Gln Thr Leu Arg Met
            20                  25                  30

Leu Glu Glu Ser Ser Ser Glu Val Thr Ser S er Ser Ala Leu Gly Leu
        35                  40                  45

Pro Pro Ala Met Val Met Ser Pro Glu Ser L eu Ala Ser Pro Glu Ile
    50                  55                  60

Gly Gly Leu Glu Leu Trp Gly Tyr Asp Asp G ly Ile Thr Tyr Ser Met
65                  70                  75                  80

Ala Gln Ser Leu Gly Thr Cys Thr Met Glu G ln Gln Gln Pro Gln Pro
                85                  90                  95

Gln Gln Gln Pro Gln Gln Thr Gln Pro Leu P ro Ser Met Pro Leu Pro
            100                 105                 110

Met Pro Pro Thr Thr Pro Lys Ser Glu Asn G lu Ser Met Ser Ser Gly
        115                 120                 125

Arg Glu Glu Leu Ser Pro Ala Ser Ser Val A sn Gly Cys Ser Thr Asp
    130                 135                 140

Gly Glu Ala Arg Arg Gln Lys Lys Gly Pro A la Pro Arg Gln Gln Glu
145                 150                 155                 160

Glu Leu Cys Leu Val Cys Gly Asp Arg Ala S er Gly Tyr His Tyr Asn
                165                 170                 175

Ala Leu Thr Cys Glu Gly Cys Lys Gly Phe P he Arg Arg Ser Val Thr
            180                 185                 190

Lys Asn Ala Val Tyr Ile Cys Lys Phe Gly H is Ala Cys Glu Met Asp
        195                 200                 205

Ile Tyr Met Arg Arg Lys Cys Gln Glu Cys A rg Leu Lys Lys Cys Leu
```

```
           210                 215                 220
Ala Val Gly Met Arg Pro Glu Cys Val Val Pro Glu Asn Gln Cys Ala
225                 230                 235                 240

Met Lys Arg Lys Glu Lys Lys Ala Gln Arg Glu Lys Asp Lys Leu Pro
                245                 250                 255

Val Ser Thr Thr Thr Val Asp Asp His Met Pro Pro Ile Met Gln Cys
                260                 265                 270

Asp Pro Pro Pro Glu Ala Ala Arg Ile Leu Glu Cys Val Gln His
                275                 280                 285

Glu Val Val Pro Arg Phe Leu Asn Glu Lys Leu Met Glu Gln Asn Arg
290                 295                 300

Leu Lys Asn Val Pro Pro Leu Thr Ala Asn Gln Lys Ser Leu Ile Ala
305                 310                 315                 320

Arg Leu Val Trp Tyr Gln Glu Gly Tyr Glu Gln Pro Ser Glu Glu Asp
                325                 330                 335

Leu Lys Arg Val Thr Gln Ser Asp Glu Asp Glu Asp Ser Asp Met
                340                 345                 350

Pro Phe Arg Gln Ile Thr Glu Met Thr Ile Leu Thr Val Gln Leu Ile
                355                 360                 365

Val Glu Phe Ala Lys Gly Leu Pro Gly Phe Ala Lys Ile Ser Gln Ser
370                 375                 380

Asp Gln Ile Thr Leu Leu Lys Ala Cys Ser Ser Glu Val Met Met Leu
385                 390                 395                 400

Arg Val Ala Arg Arg Tyr Asp Ala Ala Thr Asp Ser Val Leu Phe Ala
                405                 410                 415

Asn Asn Gln Ala Tyr Thr Arg Asp Asn Tyr Arg Lys Ala Gly Met Ala
                420                 425                 430

Tyr Val Ile Glu Asp Leu Leu His Phe Cys Arg Cys Met Tyr Ser Met
                435                 440                 445

Met Met Asp Asn Val His Tyr Ala Leu Leu Thr Ala Ile Val Ile Phe
450                 455                 460

Ser Asp Arg Pro Gly Leu Glu Gln Pro Leu Leu Val Glu Asp Ile Gln
465                 470                 475                 480

Arg Tyr Tyr Leu Asn Thr Leu Arg Val Tyr Ile Leu Asn Gln Asn Ser
                485                 490                 495

Ala Ser Pro Arg Gly Ala Val Ile Phe Gly Glu Ile Leu Gly Ile Leu
                500                 505                 510

Thr Glu Ile Arg Thr Leu Gly Met Gln Asn Ser Asn Met Cys Ile Ser
                515                 520                 525

Leu Lys Leu Lys Lys Arg Lys Leu Pro Pro Phe Leu Glu Glu Ile Trp
530                 535                 540

Asp Val Ala Asp Val Ala Thr Thr Ala Thr Pro Val Ala Ala Glu Ala
545                 550                 555                 560

Pro Ala Pro Leu Ala Pro Ala Pro Ala Arg Pro Ala Thr Val
                565                 570                 575

<210> SEQ ID NO 6
<211> LENGTH: 948
<212> TYPE: DNA
<213> ORGANISM: Spodoptera exigua

<400> SEQUENCE: 6
aggccggagt gcgtggtgcc agaaaaccag tgtgcaatga aaggaaaga g aaaaaggca      60 caaagggaaa aagacaagtt gccagtcagt acaacgacag tggatgatca c atgcctccc    120
```

```
attatgcagt gtgatccacc gcctccagag gccgcaagaa ttcacgaggt g gtgccacga    180 ttcctgaatg aaaagctaat ggacaggaca aggctcaaga atgtgccccc t cactgccaa    240 ccagaagtcc ttaatagcga ggctggtctg gtaccaagaa ggctatgaac a gccatcaga   300 agaggatcta aaaagagtca cacagtcgga tgaagacgaa gaagagtcgg a catgccgtt   360 ccgtcagatc accgagatga cgatcctcac agtgcagctc attgttgaat t cgctaaggg   420 cctaccagcg ttcgcaaaga tctcacagtc ggatcagatc acattattaa a ggcctgttc   480 gagtgaggtg atgatgttgc gagtagctcg gcggtacgac gcggcgacag a cagcgtgtt   540 gttcgccaac aaccaggcgt acaccgcgca aactaccgc aaggcaggca t ggcctacgt    600 catcgaggac ctgctgcact ctgccggtc atgtactcc atgatgatgg a taacgtcca    660 ctatgcactg ctcactgcca tcgtcatttt ctcagaccga cccgggcttg a gctaaccct   720 gttggtggag gagatccaga gatattacct gaacacgctg cgggtgtaca t cctgaacca   780 gaacagtcgg tcgccgtgct gccctgtcat ctacgctaag atcctcggca t cctgacgga   840 gctgcggacc ctgggcatgc agaactccaa catgtgcatc tcactcaagc t gaagaacag   900 gaacgtgccg ccgttcttcg aggatatctg ggacgtcctc gagtaaaa                 948
```

<210> SEQ ID NO 7
<211> LENGTH: 319
<212> TYPE: PRT
<213> ORGANISM: Spodoptera exigua

<400> SEQUENCE: 7

```
Arg Pro Glu Cys Val Pro Glu Asn Gln C ys Ala Met Lys Arg Lys
1               5                   10                  15

Glu Lys Lys Ala Gln Arg Glu Lys Asp Lys L eu Pro Val Ser Thr Thr
                20                  25                  30

Thr Val Asp Asp His Met Pro Ile Met G ln Cys Asp Pro Pro
        35                  40                  45

Pro Glu Ala Ala Arg Ile Leu Glu Cys Val G ln His Glu Val Val Pro
    50                  55                  60

Arg Phe Leu Asn Glu Lys Leu Met Glu Gln A sn Arg Leu Lys Asn Val
65              70                  75                  80

Pro Pro Leu Thr Ala Asn Gln Lys Ser Leu I le Ala Arg Leu Val Trp
                85                  90                  95

Tyr Gln Glu Gly Tyr Glu Gln Pro Ser Glu G lu Asp Leu Lys Arg Val
                100                 105                 110

Thr Gln Ser Asp Glu Asp Asp Glu Asp Ser A sp Met Pro Phe Arg Gln
            115                 120                 125

Ile Thr Glu Met Thr Ile Leu Thr Val Gln L eu Ile Val Glu Phe Ala
    130                 135                 140

Lys Gly Leu Pro Gly Phe Ala Lys Ile Ser G ln Ser Asp Gln Ile Thr
145             150                 155                 160

Leu Leu Lys Ala Cys Ser Ser Gly Val Met M et Leu Arg Val Ala Arg
                165                 170                 175

Arg Tyr Asp Ala Ala Thr Asp Ser Val Leu P he Ala Asn Asn Gln Ala
            180                 185                 190

Tyr Thr Arg Asp Asn Tyr Arg Lys Ala Gly M et Ala Tyr Val Ile Glu
        195                 200                 205

Asp Leu Leu His Phe Cys Arg Cys Met Tyr S er Met Met Met Asp Asn
    210                 215                 220
```

```
Val His Tyr Ala Leu Leu Thr Ala Ile Val Ile Phe Ser Asp Arg Pro
225                 230                 235                 240

Gly Leu Glu Gln Pro Leu Leu Val Glu Glu Ile Gln Arg Tyr Tyr Leu
                245                 250                 255

Asn Thr Leu Arg Val Tyr Ile Leu Asn Gln Asn Ser Ala Ser Pro Arg
            260                 265                 270

Gly Ala Val Ile Phe Gly Glu Ile Leu Gly Ile Leu Thr Glu Ile Arg
        275                 280                 285

Thr Leu Gly Met Gln Asn Ser Asn Met Cys Ile Ser Leu Lys Leu Lys
    290                 295                 300

Lys Arg Lys Leu Pro Pro Phe Leu Glu Glu Ile Asp Trp Asp Val
305                 310                 315

<210> SEQ ID NO 8
<211> LENGTH: 116
<212> TYPE: DNA
<213> ORGANISM: Heliothis virescens

<400> SEQUENCE: 8
tactcttggc attttctccg catatacata tccatttcgc aagcatggcc g aatttgcat      60 atgtacactg cattttggt tacactccgc ctgaagaact ccttgcaccc c tcgca         116

<210> SEQ ID NO 9
<211> LENGTH: 1934
<212> TYPE: DNA
<213> ORGANISM: Heliothis virescens

<400> SEQUENCE: 9
ccgtacgaaa tcgggtacgg gtgtgccctc ttaagtggta aaattcgcag t ccttataaa     60 taggttgatc acgtcgacgt cagtgtccgt gcacttcact aaaactagcc a gtctatgag   120 cgttctctcc tgaggcgcgc tagacggtgg cgggcggccg gcgggcggg g cggggcta    180 gaggcgccgg cgcctccgcc gccaccggcg tcgccgtcct ggccgcacct g ccacgtccc   240 agatctcctc gaggaacggc ggcagcttcc tgttcttcag cttgagggag a tgcacatgt   300 tggagttctg catgcccagc gtgcggatct ccgtcagtat gcccaggatc t cgccgaaga   360 tgacggcgcc gcggggcgac gcgctgttct ggttcaggat gtacacccgt a gcgtgttca   420 ggtaatatct ctggatgtcc tccaccaaca ggggttgctc aagcccgggc c ggtctgaga   480 agatgacaat ggctgtaagc agcgcataat gcacgttatc catcatcatg g agtacatgc   540 accgacagaa gcgtagcagg tcctcgatga cgtacgccat gcctgccttg c ggtagttgt   600 cgcgagtgta cgcctggttg ttcgcgaaca gtacgctgtc ggtggccgcg t cataccgcc   660 gagccactcg gagcatcatc acctcacttg agcacgcctt aataacgtga t ctggtccg    720 actgcgagat cttggcgaag cccgggaggc ccttagcgaa ttctacgatg a gctgcactg   780 tgagaatcgt catctcggta atctgacgga acggcatatc cgagtcttcg t cgtcctcgt   840 ccgactgtgt aaccctcttc aggtcttcct cggaaggttg ttcatagcct t cctggtacc   900 acacgagcct tgcgatcaac gacttctgat ggcagtgag gggggcacg t tcttcaatc    960 tgttctgttc cattagcttc tcattcagga atcgtggcac cacctcgtgc t gcacacatt  1020 ccagaattct agcggcctct ggggcggag gtcacattg catgatggga g gcatgtgat   1080 cgtctactgt cgtcgtactg acgggcaatt tgtcttttc cctctgcgcc t tttctctt    1140 tccgtttcat tgcacactgg ttctccggca ccacgcactc gggcctcatg c ccaccgcaa   1200 gacatttctt caaccgacac tcctgacatt ttctccgcat atagatatcc a tttcgcaag  1260
```

-continued

```
catggccgaa tttgcatatg tacactgcat ttttggttac actccgcctg a agaaacctt   1320
tacacccttc acatgtgagc gcgttgtagt gatatccgga ggctctgtcg c cgcagacaa   1380
gacatagctc ttcttgctgc ctcggcgctg ggcctttctt ctgccgcctc g cctcgccat   1440
ctgtgctgca gccgtttaca ctcgaagctg gagacagttc ctcacgacct g atgacattg   1500
actcgttttc tgatttgggt gttgtcggtg gcattggtaa cggcatggaa g gtaggggtt   1560
gtgtctgctg caggttagct agctgcggct ggggaattcc gcgggaatga t attctgctg   1620
agcaccacgg ccatcacgcc acagtttacg acggagtcca tccactgtct t ctgggtggc   1680
agtggtggcg tgtacagtgg tcatcagacc ttcaatgatc tcgaagttgt c atggatgac   1740
cttagcgaga ggagcgaggc agttggttgt gcaggaggcg ttggagatga c cttgtaaga   1800
ggggtcatac tgcttcaagg ttgacaccaa cgacgaacat gggtcagcgc t gggcagcag   1860
gagatgatga ccttcttagc accaccctct aaatgagcag aggccttttc t gtggtggtg   1920
aaaacaccag tgga                                                    1934
```

```
<210> SEQ ID NO 10
<211> LENGTH: 2463
<212> TYPE: DNA
<213> ORGANISM: Heliothis virescens
<220> FEATURE:
<221> NAME/KEY: modified_base
<222> LOCATION: (224)..(224)
<223> OTHER INFORMATION: i
<400> SEQUENCE: 10
gaagttccgg gtcgagtgtc catgtcagta aatcacttaa acaaaaggct t gctcgtgtg     60
gaagctatcg acgacacaca ctttgtattg taataagaca cacttatatc a ccctatggt    120
agataatcaa cacattaaaa tgtaatcaca gcaataaatt aaattactca t ttagtcgag    180
ggtcgcgggc acaggacgat ggaaccatga aacacgataa cgcncctcac g tgtgcatca    240
gaaacaaaca tgtgacggcg acgtggacag cggacgactc atcacaatat t atactcgaa    300
aggttaatca acgtattatt gttaattttg gtaaataaac ataactatca a cttttcacc    360
caatagaaac atcttcttct tatattcttt gtctctaata actctcgtaa g ctacgtacg    420
tatgtgtaat ttagtaggtg tacttatcga acgaagtctt atcatacagt c gtatccgag    480
tgaccaactc agtcgtaaac gaaataaaac tgaagccgcg ggcgccgcga t cgccgccga    540
ccggcgacgg cgtgcgggcc cgaacagcaa caccaatata tattctccaa a tcgttcaac    600
aacacatata ttcacattac acacgctctg catcgtcgtc ggtcaccgaa t acgtacgaa    660
atcgggtacg ggtgtgccct cttaagtggt aaaattcgca gtccttataa a taggttgat    720
cacgtcgacg tcagtgtccg tgcacttcac taaaactagc cagtctatga g cgttctctc    780
ctgaggcgcg ctagacggtg gcgggcggcc gggcgggcgg ggcgggggct a gaggcgccg    840
gcgcctccgc cgccacccgg cgtccgttgc cgccacgtcc gccacgtccc a gatctcctc    900
gaggaacggc ggcagcttcc tgttcttcag cttgagggag atgcacatgt t ggagttctg    960
catgcccagc gtgcggatct ccgtcagtat gcccaggatc tcgccgaaga t gacggcgcc   1020
gcggggcgac gcgctgttct ggttcaggat gtacacccgt agcgtgttca g gtaatatct   1080
ctggatgtcc tccaccaaca ggggttgctc aagcccgggc cggtctgaga a gatgacaat   1140
ggctgtaagc agcgcataat gcacgttatc catcatcatg gagtacatgc a ccgacagaa   1200
gtgcagcagg tcctcgatga cgtacgccat gcctgccttg cggtagttgt c gcgagtgta   1260

-continued

```
cgcctggttg ttcgcgaaca gtacgctgtc ggtggccgcg tcataccgcc g agccactcg      1320
gagcatcatc acctcacttg agcacgcctt taataacgtg atctggtccg a ctgcgagat      1380
cttggcgaag cccgggaggc ccttagcgaa ttctacgatg agctgcactg t gagaatcgt      1440
catctcggta atctgacgga acggcatatc cgagtcttcg tcgtcctcgt c cgactgtgt      1500
aaccctcttc aggtcttcct cggaaggttg ttcatagcct tcctggtacc a cacgagcct      1560
tgcgatcaac gacttctgat tggcagtgag gggggcacg ttcttcaatc t gttctgttc       1620
cattagcttc tcattcagga atcgtggcac caccctcgtgc tgcacacatt c cagaattct     1680
agcggcctct gggggcggag ggtcacattg catgatggga ggcatgtgat c gtctactgt      1740
cgtcgtactg acgggcaatt tgtcttttc cctctgcgcc ttttctctt t ccgtttcat        1800
tgcacactgg ttctccggca ccacgcactc gggcctcatg cccaccgcaa g acatttctt     1860
caaccgacac tcctgacatt ttctccgcat atagatatcc atttcgcaag c atggccgaa     1920
tttgcatatg tacactgcat ttttggttac actccgcctg aagaaacctt t acacccttc     1980
acatgtgagc gcgttgtagt gatatccgga ggctctgtcg ccgcagacaa g acatagctc     2040
ttcttgctgc ctcggcgctg ggcctttctt ctgccgcctc gcctcgccat c tgtgctgca     2100
gccgtttaca ctcgaagctg gagacagttc ctcacgacct gatgacattg a ctcgttttc     2160
tgatttgggt gttgtcggtg gcattggtaa cggcatggaa ggtagggggtt g tgtctgctg    2220
cggctgctgc tgcggctggg gctgctgctg ctccatggtg caggtgccca g cgactgtgc     2280
catgctgtaa gtgatgccat cgtcgtagcc ccacagctcc aggccgccga t ctcgggcga    2340
cgcgagcgat tccggggaca tcaccatagc cggcggcagg cccagtgctg a agacgacgt    2400
cacctcagac gagctctcct cgagcattcg cagcgtctgg aatggtccgt t gttatacca    2460
gcg                                                                    2463
```

<210> SEQ ID NO 11
<211> LENGTH: 606
<212> TYPE: PRT
<213> ORGANISM: Bombyx mori

<400> SEQUENCE: 11

```
Met Arg Val Glu Asn Val Asp Asn Val Ser P he Ala Leu Asn Gly Arg
1               5                   10                  15

Ala Asp Glu Trp Cys Met Ser Val Glu Thr A rg Leu Asp Ser Leu Val
            20                  25                  30

Arg Glu Lys Ser Glu Val Lys Ala Tyr Val G ly Gly Cys Pro Ser Val
        35                  40                  45

Ile Thr Asp Ala Gly Ala Tyr Asp Ala Leu P he Asp Met Arg Arg Arg
    50                  55                  60

Trp Ser Asn Asn Gly Gly Phe Pro Leu Arg M et Leu Glu Glu Ser Ser
65                  70                  75                  80

Ser Glu Val Thr Ser Ser Ser Ala Leu Gly L eu Pro Pro Ala Met Val
                85                  90                  95

Met Ser Pro Glu Ser Leu Ala Ser Pro Glu T yr Gly Ala Leu Glu Leu
            100                 105                 110

Trp Ser Tyr Asp Asp Gly Ile Thr Tyr Asn T hr Ala Gln Ser Leu Leu
        115                 120                 125

Gly Ala Cys Asn Met Gln Gln Gln Leu G ln Pro Gln Gln Pro His
    130                 135                 140

Pro Ala Pro Pro Thr Leu Pro Thr Met Pro L eu Pro Met Pro Pro Thr
145                 150                 155                 160
```

```
Thr Pro Lys Ser Glu Asn Glu Ser Met Ser Ser Gly Arg Glu Glu Leu
                165                 170                 175
Ser Pro Ala Ser Ser Ile Asn Gly Cys Ser Ala Asp Ala Asp Ala Arg
            180                 185                 190
Arg Gln Lys Lys Gly Pro Ala Pro Arg Gln Gln Glu Glu Leu Cys Leu
        195                 200                 205
Val Cys Gly Asp Arg Ala Ser Gly Tyr His Tyr Asn Ala Leu Thr Cys
    210                 215                 220
Glu Gly Cys Lys Gly Phe Phe Arg Arg Ser Val Thr Lys Asn Ala Val
225                 230                 235                 240
Tyr Ile Cys Lys Phe Gly His Ala Cys Glu Met Asp Met Tyr Met Arg
                245                 250                 255
Arg Lys Cys Gln Glu Cys Arg Leu Lys Lys Cys Leu Ala Val Gly Met
                260                 265                 270
Arg Pro Glu Cys Val Ile Gln Glu Pro Ser Lys Asn Lys Asp Arg Gln
                275                 280                 285
Arg Gln Lys Lys Asp Lys Gly Ile Leu Leu Pro Val Ser Thr Thr Thr
            290                 295                 300
Val Glu Asp His Met Pro Pro Ile Met Gln Cys Asp Pro Pro Pro Pro
305                 310                 315                 320
Glu Ala Ala Arg Ile His Glu Val Val Pro Arg Tyr Leu Ser Glu Lys
                325                 330                 335
Leu Met Glu Gln Asn Arg Gln Lys Asn Ile Pro Pro Leu Ser Ala Asn
                340                 345                 350
Gln Lys Ser Leu Ile Ala Arg Leu Val Trp Tyr Gln Glu Gly Tyr Glu
            355                 360                 365
Gln Pro Ser Asp Glu Asp Leu Lys Arg Val Thr Gln Thr Trp Gln Ser
        370                 375                 380
Asp Glu Glu Asp Glu Glu Ser Asp Leu Pro Phe Arg Gln Ile Thr Glu
385                 390                 395                 400
Met Thr Ile Leu Thr Val Gln Leu Ile Val Glu Phe Ala Lys Gly Leu
                405                 410                 415
Pro Gly Phe Ser Lys Ile Ser Gln Ser Asp Gln Ile Thr Leu Leu Lys
                420                 425                 430
Ala Ser Ser Ser Glu Val Met Met Leu Arg Val Ala Arg Arg Tyr Asp
            435                 440                 445
Ala Ala Ser Asp Ser Val Leu Phe Ala Asn Asn Lys Ala Tyr Thr Arg
        450                 455                 460
Asp Asn Tyr Arg Gln Gly Gly Met Ala Tyr Val Ile Glu Asp Leu Leu
465                 470                 475                 480
His Phe Cys Arg Cys Met Phe Ala Met Gly Met Asp Asn Val His Phe
                485                 490                 495
Ala Leu Leu Thr Ala Ile Val Ile Phe Ser Asp Arg Pro Gly Leu Glu
                500                 505                 510
Gln Pro Ser Leu Val Glu Glu Ile Gln Arg Tyr Tyr Leu Asn Thr Leu
            515                 520                 525
Arg Ile Tyr Ile Ile Asn Gln Asn Ser Ala Ser Ser Arg Cys Ala Val
        530                 535                 540
Ile Tyr Gly Arg Ile Leu Ser Val Leu Thr Glu Leu Arg Thr Leu Gly
545                 550                 555                 560
Thr Gln Asn Ser Asn Met Cys Ile Ser Leu Lys Leu Lys Asn Arg Lys
                565                 570                 575
```

```
Leu Pro Pro Phe Leu Glu Glu Ile Trp Asp Val Ala Glu Val Ala Arg
            580                 585                 590

Arg His Pro Thr Val Leu Pro Pro Thr Asn Pro Val Val Leu
            595                 600             605

<210> SEQ ID NO 12
<211> LENGTH: 557
<212> TYPE: PRT
<213> ORGANISM: Manduca sexta

<400> SEQUENCE: 12

Met Arg Arg Arg Trp Ser Asn Asn Gly Cys Phe Pro Leu Arg Met Phe
1               5                   10                  15

Glu Glu Ser Ser Ser Glu Val Thr Ser Ser Ser Ala Phe Gly Met Pro
            20                  25                  30

Ala Ala Met Val Met Ser Pro Glu Ser Leu Ala Ser Pro Glu Tyr Gly
        35                  40                  45

Gly Leu Glu Leu Trp Ser Tyr Asp Glu Thr Met Thr Asn Tyr Pro Ala
    50                  55                  60

Gln Ser Leu Leu Gly Ala Cys Asn Ala Pro Gln Gln Gln Gln Gln Gln
65                  70                  75                  80

Gln Gln Gln Gln Pro Ser Ala Gln Pro Leu Pro Ser Met Pro Leu Pro
                85                  90                  95

Met Pro Pro Thr Thr Pro Lys Ser Glu Asn Glu Ser Met Ser Ser Gly
            100                 105                 110

Arg Glu Glu Leu Ser Pro Ala Ser Ser Ile Asn Gly Cys Ser Thr Asp
        115                 120                 125

Gly Glu Pro Arg Arg Gln Lys Lys Gly Pro Ala Pro Arg Gln Gln Glu
130                 135                 140

Glu Leu Cys Leu Val Cys Gly Asp Arg Ala Ser Gly Tyr His Tyr Asn
145                 150                 155                 160

Ala Leu Thr Cys Glu Gly Cys Lys Gly Phe Phe Arg Arg Ser Val Thr
                165                 170                 175

Lys Asn Ala Val Tyr Ile Cys Lys Phe Gly His Ala Cys Glu Met Asp
            180                 185                 190

Met Tyr Met Arg Arg Lys Cys Gln Glu Cys Arg Leu Lys Lys Cys Leu
        195                 200                 205

Ala Val Gly Met Arg Pro Glu Cys Val Val Pro Glu Ser Thr Cys Lys
    210                 215                 220

Asn Lys Arg Arg Glu Lys Glu Ala Gln Arg Glu Lys Asp Lys Leu Pro
225                 230                 235                 240

Val Ser Thr Thr Thr Val Asp Asp His Met Pro Ala Ile Met Gln Cys
                245                 250                 255

Asp Pro Pro Pro Glu Ala Ala Arg Ile His Glu Val Val Pro Arg
            260                 265                 270

Phe Leu Thr Glu Lys Leu Met Glu Gln Asn Arg Leu Lys Asn Val Thr
        275                 280                 285

Pro Leu Ser Ala Asn Gln Lys Ser Leu Leu Ile Ala Arg Leu Val Met
    290                 295                 300

Tyr Gln Glu Gly Tyr Glu Gln Pro Ser Glu Glu Asp Leu Lys Arg Val
305                 310                 315                 320

Thr Gln Thr Trp Gln Leu Glu Glu Glu Glu Glu Thr Asp Met
                325                 330                 335

Pro Phe Arg Gln Ile Thr Glu Met Thr Ile Leu Thr Val Gln Leu Ile
            340                 345                 350
```

```
Val Glu Phe Ala Lys Gly Leu Pro Gly Phe Ser Lys Ile Ser Gln Ser
    355                 360                 365

Asp Gln Ile Thr Leu Leu Lys Ala Ser Ser Glu Val Met Met Leu
    370                 375                 380

Arg Val Ala Arg Arg Tyr Asp Ala Ala Thr Asp Ser Val Leu Phe Ala
385                 390                 395                 400

Asn Asn Gln Ala Tyr Thr Arg Asp Asn Tyr Arg Lys Ala Gly Met Ser
                405                 410                 415

Tyr Val Ile Glu Asp Leu Leu His Phe Cys Arg Cys Met Tyr Ser Met
                420                 425                 430

Ser Met Asp Asn Val His Tyr Ala Leu Leu Thr Ala Ile Val Ile Phe
                435                 440                 445

Ser Asp Arg Pro Gly Leu Glu Gln Pro Leu Leu Val Glu Glu Ile Gln
                450                 455                 460

Arg Tyr Tyr Leu Lys Thr Leu Arg Val Tyr Ile Leu Asn Gln His Ser
465                 470                 475                 480

Ala Ser Pro Arg Cys Ala Val Leu Phe Gly Lys Ile Leu Gly Val Leu
                485                 490                 495

Thr Glu Leu Arg Thr Leu Gly Thr Gln Asn Ser Asn Met Cys Ile Ser
                500                 505                 510

Leu Lys Leu Lys Asn Arg Lys Leu Pro Pro Phe Leu Glu Glu Ile Trp
                515                 520                 525

Asp Val Ala Glu Val Ser Thr Thr Gln Pro Thr Pro Gly Val Ala Ala
                530                 535                 540

Gln Val Thr Pro Ile Val Val Asp Asn Pro Ala Ala Leu
545                 550                 555

<210> SEQ ID NO 13
<211> LENGTH: 536
<212> TYPE: PRT
<213> ORGANISM: Chironomus tentans

<400> SEQUENCE: 13

Met Lys Thr Glu Asn Leu Ile Val Thr Thr Val Lys Val Glu Pro Leu
1               5                   10                  15

Asn Tyr Ala Ser Gln Ser Phe Gly Asp Asn Ile Tyr Gly Gly Ala
            20                  25                  30

Thr Lys Lys Gln Arg Leu Glu Ser Asp Glu Thr Met Asn His Asn Gln
        35                  40                  45

Thr Asn Met Asn Leu Glu Ser Ser Asn Met Asn His Asn Thr Ile Ser
    50                  55                  60

Gly Phe Ser Ser Pro Asp Val Asn Tyr Glu Ala Tyr Ser Pro Asn Ser
65                  70                  75                  80

Lys Leu Asp Asp Gly Asn Met Ser Val His Met Gly Asp Gly Leu Asp
                85                  90                  95

Gly Lys Lys Ser Ser Ser Lys Lys Gly Pro Val Pro Arg Gln Gln Glu
                100                 105                 110

Glu Leu Cys Leu Val Cys Gly Asp Arg Ala Ser Gly Tyr His Tyr Asn
        115                 120                 125

Ala Leu Thr Cys Glu Gly Cys Lys Gly Phe Phe Arg Arg Ser Val Thr
    130                 135                 140

Lys Asn Ala Val Tyr Cys Cys Lys Phe Gly His Glu Cys Glu Met Asp
145                 150                 155                 160

Met Tyr Met Arg Arg Lys Cys Gln Glu Cys Arg Leu Lys Lys Cys Leu
```

165                 170                 175
Ala Val Gly Met Arg Pro Glu Cys Val Val Pro Glu Asn Gln Cys Ala
                180                 185                 190

Ile Lys Arg Lys Glu Lys Lys Ala Gln Lys Glu Lys Asp Lys Val Pro
            195                 200                 205

Gly Ile Val Gly Ser Asn Thr Ser Ser Ser Leu Leu Asn Gln Ser
        210                 215                 220

Leu Asn Asn Gly Ser Leu Lys Asn Leu Glu Ile Ser Tyr Arg Glu Glu
225                 230                 235                 240

Leu Leu Gln Gln Leu Met Lys Cys Asp Pro Pro His Pro Met Gln
                245                 250                 255

Gln Leu Leu Pro Glu Lys Leu Leu Met Glu Asn Arg Ala Lys Gly Thr
            260                 265                 270

Pro Gln Leu Thr Ala Asn Gln Val Ala Val Ile Tyr Lys Leu Ile Trp
        275                 280                 285

Tyr Gln Asp Gly Tyr Glu Gln Pro Ser Glu Glu Asp Leu Lys Arg Ile
        290                 295                 300

Thr Thr Glu Leu Glu Glu Glu Asp Gln Glu His Glu Ala Asn Phe
305                 310                 315                 320

Arg Tyr Ile Thr Glu Val Thr Ile Leu Thr Val Gln Leu Ile Val Glu
                325                 330                 335

Phe Ala Lys Gly Leu Pro Ala Phe Ile Lys Ile Pro Gln Glu Asp Gln
            340                 345                 350

Ile Thr Leu Leu Lys Ala Cys Ser Ser Glu Val Met Met Leu Arg Met
        355                 360                 365

Ala Arg Arg Tyr Asp His Asp Ser Asp Ser Ile Leu Phe Ala Asn Asn
370                 375                 380

Thr Ala Tyr Thr Lys Gln Thr Tyr Gln Leu Ala Gly Met Glu Glu Thr
385                 390                 395                 400

Ile Asp Asp Leu Leu His Phe Cys Arg Gln Met Tyr Ala Leu Ser Ile
                405                 410                 415

Asp Asn Val Glu Thr Ala Leu Leu Thr Ala Ile Val Ile Phe Ser Asp
            420                 425                 430

Arg Pro Gly Leu Glu Lys Ala Glu Met Val Asp Ile Ile Gln Ser Tyr
        435                 440                 445

Tyr Thr Glu Thr Leu Lys Val Tyr Ile Val Arg Asp His Gly Gly Glu
        450                 455                 460

Ser Arg Cys Ser Val Gln Phe Ala Lys Leu Leu Gly Ile Leu Thr Glu
465                 470                 475                 480

Leu Arg Thr Met Gly Asn Leu Asn Ser Glu Met Cys Phe Ser Leu Lys
                485                 490                 495

Leu Arg Asn Arg Lys Leu Pro Arg Phe Leu Glu Glu Val Trp Asp Val
            500                 505                 510

Gly Asp Val Asn Asn Gln Thr Thr Ala Thr Thr Asn Thr Glu Asn Ile
        515                 520                 525

Val Arg Glu Arg Ile Asn Arg Asn
        530                 535

<210> SEQ ID NO 14
<211> LENGTH: 674
<212> TYPE: PRT
<213> ORGANISM: Aedes aegypti

<400> SEQUENCE: 14

```
Met Met Lys Arg Arg Trp Ser Asn Asn Gly Gly Phe Thr Ala Leu Arg
  1               5                  10                  15

Met Leu Asp Asp Ser Ser Ser Glu Val Thr Ser Ser Ser Ala Ala Leu
             20                  25                  30

Gly Met Thr Met Ser Pro Asn Ser Leu Gly Ser Pro Asn Tyr Asp Glu
             35                  40                  45

Leu Glu Leu Trp Ser Ser Tyr Glu Asp Asn Ala Tyr Asn Gly His Ser
     50                  55                  60

Val Leu Ser Asn Gly Asn Asn Leu Gly Gly Cys Gly Ala Ala Asn
 65                  70                  75                  80

Asn Leu Leu Met Asn Gly Ile Val Gly Asn Asn Asn Leu Asn Gly Met
                 85                  90                  95

Met Asn Met Ala Ser Gln Ala Val Gln Ala Asn Ala Asn Ser Ile Gln
                100                 105                 110

His Ile Val Gly Asn Leu Ile Asn Gly Val Asn Pro Asn Gln Thr Leu
            115                 120                 125

Ile Pro Pro Leu Pro Ser Ile Ile Gln Asn Thr Leu Met Asn Thr Pro
130                 135                 140

Arg Ser Glu Ser Val Asn Ser Ile Ser Ser Gly Arg Glu Asp Leu Ser
145                 150                 155                 160

Pro Ser Ser Ser Leu Asn Gly Tyr Thr Asp Gly Ser Asp Ala Lys Lys
                165                 170                 175

Gln Lys Lys Gly Pro Thr Pro Arg Gln Gln Glu Glu Leu Cys Leu Val
            180                 185                 190

Cys Gly Asp Arg Ala Ser Gly Tyr His Tyr Asn Ala Leu Thr Cys Glu
            195                 200                 205

Gly Cys Lys Gly Phe Phe Arg Arg Ser Val Thr Lys Asn Ala Val Tyr
210                 215                 220

Cys Cys Lys Phe Gly His Ala Cys Glu Met Asp Met Tyr Met Arg Arg
225                 230                 235                 240

Lys Cys Gln Glu Cys Arg Leu Lys Lys Cys Leu Ala Val Gly Met Arg
            245                 250                 255

Pro Glu Cys Val Val Pro Glu Asn Gln Cys Ala Ile Lys Arg Lys Glu
            260                 265                 270

Lys Lys Ala Gln Lys Glu Lys Asp Lys Val Gln Thr Asn Ala Thr Val
            275                 280                 285

Ser Thr Thr Asn Ser Thr Tyr Arg Ser Glu Ile Leu Pro Ile Leu Met
            290                 295                 300

Lys Cys Asp Pro Pro His Gln Ala Ile Pro Leu Leu Pro Glu Lys
305                 310                 315                 320

Leu Leu Gln Glu Asn Arg Leu Arg Asn Ile Pro Leu Leu Thr Ala Asn
                325                 330                 335

Gln Met Ala Val Ile Tyr Lys Leu Ile Trp Tyr Gln Asp Gly Tyr Glu
            340                 345                 350

Gln Pro Ser Glu Glu Asp Leu Lys Arg Ile Met Ile Gly Ser Pro Asn
            355                 360                 365

Glu Glu Glu Asp Gln His Asp Val His Phe Arg His Ile Thr Glu Ile
            370                 375                 380

Thr Ile Leu Thr Val Gln Leu Ile Val Glu Phe Ala Lys Gly Leu Pro
385                 390                 395                 400

Ala Phe Thr Lys Ile Pro Gln Glu Asp Gln Ile Thr Leu Leu Lys Ala
            405                 410                 415

Cys Ser Ser Glu Val Met Met Leu Arg Met Ala Arg Arg Tyr Asp Ala
```

```
            420                 425                 430
Ala Thr Asp Ser Ile Leu Phe Ala Asn Asn Arg Ser Tyr Thr Arg Asp
            435                 440                 445

Ser Tyr Arg Met Ala Gly Met Ala Asp Thr Ile Glu Asp Leu Leu His
    450                 455                 460

Phe Cys Arg Gln Met Phe Ser Leu Thr Val Asp Asn Val Glu Tyr Ala
465                 470                 475                 480

Leu Leu Thr Ala Ile Val Ile Phe Ser Asp Arg Pro Gly Leu Glu Gln
                485                 490                 495

Ala Glu Leu Val Glu His Ile Gln Ser Tyr Tyr Ile Asp Thr Leu Arg
            500                 505                 510

Ile Tyr Ile Leu Asn Arg His Ala Gly Asp Pro Lys Cys Ser Val Ile
        515                 520                 525

Phe Ala Lys Leu Leu Ser Ile Leu Thr Glu Leu Arg Thr Leu Gly Asn
    530                 535                 540

Gln Asn Ser Glu Met Cys Phe Ser Leu Lys Leu Lys Asn Arg Lys Leu
545                 550                 555                 560

Pro Arg Phe Leu Glu Glu Ile Trp Asp Val Gln Asp Ile Pro Pro Ser
                565                 570                 575

Met Gln Ala Gln Met His Ser His Gly Thr Gln Ser Ser Ser Ser Ser
            580                 585                 590

Ser Ser Ser Ser Ser Ser Ser Asn Gly Ser Ser Asn Gly Asn Ser
        595                 600                 605

Ser Ser Asn Ser Asn Ser Ser Gln His Gly Pro His Pro His Pro His
    610                 615                 620

Gly Gln Gln Leu Thr Pro Asn Gln Gln Gln His Gln Gln Gln His Ser
625                 630                 635                 640

Gln Leu Gln Gln His Ala Asn Gly Ser Gly Ser Gly Gly Gly Ser Asn
                645                 650                 655

Asn Asn Ser Ser Ser Gly Gly Val Val Pro Gly Leu Gly Met Leu Asp
            660                 665                 670

Gln Val

<210> SEQ ID NO 15
<211> LENGTH: 878
<212> TYPE: PRT
<213> ORGANISM: Drosophila melanogaster

<400> SEQUENCE: 15

Met Lys Arg Arg Trp Ser Asn Asn Gly Gly Phe Met Arg Leu Pro Glu
1               5                   10                  15

Glu Ser Ser Glu Val Thr Ser Ser Ser Asn Gly Leu Val Leu Pro
            20                  25                  30

Ser Gly Val Asn Met Ser Pro Ser Ser Leu Asp Ser His Asp Tyr Cys
        35                  40                  45

Asp Asn Asp Lys Trp Leu Cys Gly Asn Glu Ser Gly Ser Phe Gly Gly
    50                  55                  60

Ser Asn Gly His Gly Leu Ser Gln Gln Gln Gln Ser Val Ile Thr Leu
65                  70                  75                  80

Ala Met His Gly Cys Ser Ser Thr Leu Pro Ala Gln Thr Thr Ile Ile
                85                  90                  95

Pro Ile Asn Gly Asn Ala Asn Gly Asn Gly Gly Ser Thr Asn Gly Gln
            100                 105                 110

Tyr Val Pro Gly Ala Thr Asn Leu Gly Ala Leu Ala Asn Gly Met Leu
```

-continued

```
              115                 120                      125
Asn Gly Gly Phe Asn Gly Met Gln Gln Gln I le Gln Asn Gly His Gly
        130                 135                 140
Leu Ile Asn Ser Thr Thr Pro Ser Thr Pro T hr Thr Pro Leu His Leu
145                 150                 155                     160
Gln Gln Asn Leu Gly Gly Ala Gly Gly G ly Ile Gly Gly Met Gly
                165                 170                 175
Ile Leu His His Ala Asn Gly Thr Pro Asn G ly Leu Ile Gly Val Val
                180                 185                 190
Gly Gly Gly Gly Val Gly Leu Gly Val G ly Gly Gly Val Gly
                195                 200                 205
Gly Leu Gly Met Gln His Thr Pro Arg Ser A sp Ser Val Asn Ser Ile
    210                 215                 220
Ser Ser Gly Arg Asp Asp Leu Ser Pro Ser S er Ser Leu Asn Gly Tyr
225                 230                 235                 240
Ser Ala Asn Glu Ser Cys Asp Ala Lys Lys S er Lys Lys Gly Pro Ala
                245                 250                 255
Pro Arg Val Gln Glu Glu Leu Cys Leu Val C ys Gly Asp Arg Ala Ser
                260                 265                 270
Gly Tyr His Tyr Asn Ala Leu Thr Cys Glu G ly Cys Lys Gly Phe Phe
        275                 280                 285
Arg Arg Ser Val Thr Lys Ser Ala Val Tyr C ys Cys Lys Phe Gly Arg
    290                 295                 300
Ala Cys Glu Met Asp Met Tyr Met Arg Arg L ys Cys Gln Glu Cys Arg
305                 310                 315                 320
Leu Lys Lys Cys Leu Ala Val Gly Met Arg P ro Gly Cys Val Val Pro
                325                 330                 335
Gly Asn Gln Cys Ala Met Lys Arg Arg Glu L ys Lys Ala Gln Lys Glu
            340                 345                 350
Lys Asp Lys Met Thr Thr Ser Pro Ser Ser G ln His Gly Gly Asn Gly
                355                 360                 365
Ser Leu Ala Ser Gly Gly Gly Gln Asp Phe V al Lys Lys Glu Ile Leu
    370                 375                 380
Asp Leu Met Thr Cys Glu Pro Pro Gln His A la Thr Ile Pro Leu Leu
385                 390                 395                 400
Pro Asp Glu Ile Leu Ala Lys Cys Gln Ala A rg Asn Ile Pro Ser Leu
                405                 410                 415
Thr Tyr Asn Gln Leu Ala Val Ile Thr Lys L eu Ile Trp Tyr Gln Asp
            420                 425                 430
Gly Tyr Glu Gln Pro Ser Glu Glu Asp Leu A rg Arg Ile Met Ser Gln
        435                 440                 445
Pro Asp Glu Asn Glu Ser Gln Thr Asp Val S er Phe Arg His Ile Thr
    450                 455                 460
Glu Ile Thr Ile Leu Thr Val Gln Leu Ile V al Glu Phe Ala Lys Gly
465                 470                 475                 480
Leu Pro Ala Phe Thr Lys Ile Pro Gln Glu A sp Gln Ile Thr Leu Leu
                485                 490                 495
Lys Ala Cys Ser Ser Glu Val Met Met Leu A rg Met Ala Arg Arg Tyr
                500                 505                 510
Asp His Ser Ser Asp Ser Ile Phe Phe Ala A sn Asn Arg Ser Tyr Thr
        515                 520                 525
Arg Asp Ser Tyr Lys Met Ala Gly Met Ala A sp Asn Ile Glu Asp Leu
    530                 535                 540
```

```
Leu His Phe Cys Arg Gln Met Phe Ser Met Lys Val Asp Asn Val Glu
545                 550                 555                 560

Tyr Ala Leu Leu Thr Ala Ile Val Ile Phe Ser Asp Arg Pro Gly Leu
                565                 570                 575

Glu Lys Ala Gln Leu Val Glu Ala Ile Gln Ser Tyr Tyr Ile Asp Thr
            580                 585                 590

Leu Arg Ile Thr Ile Leu Asn Arg His Cys Gly Asp Ser Met Ser Leu
        595                 600                 605

Val Phe Tyr Ala Lys Leu Leu Ser Ile Leu Thr Glu Leu Arg Thr Leu
    610                 615                 620

Gly Asn Gln Asn Ala Glu Met Cys Phe Ser Leu Lys Leu Lys Asn Arg
625                 630                 635                 640

Lys Leu Pro Lys Phe Leu Glu Glu Ile Trp Asp Val His Ala Ile Pro
                645                 650                 655

Pro Ser Val Gln Ser His Leu Gln Ile Thr Gln Glu Glu Asp Glu Arg
            660                 665                 670

Leu Glu Arg Ala Glu Arg Met Arg Ala Ser Val Gly Gly Ala Ile Thr
        675                 680                 685

Ala Gly Ile Asp Cys Asp Ser Ala Ser Thr Ser Ala Ala Ala Ala Ala
    690                 695                 700

Ala Gln His Gln Pro Gln Pro Gln Pro Gln Pro Gln Pro Ser Ser Leu
705                 710                 715                 720

Thr Gln Asn Asp Ser Gln His Gln Thr Gln Pro Gln Leu Gln Pro Gln
                725                 730                 735

Leu Pro Pro Gln Leu Gln Gly Gln Leu Gln Pro Gln Leu Gln Pro Gln
            740                 745                 750

Leu Gln Thr Gln Leu Gln Pro Gln Ile Gln Pro Gln Pro Gln Leu Leu
        755                 760                 765

Pro Val Ser Ala Pro Val Pro Ala Ser Val Thr Ala Pro Gly Ser Leu
    770                 775                 780

Ser Ala Val Ser Thr Ser Ser Glu Tyr Met Gly Gly Ser Ala Ala Ile
785                 790                 795                 800

Gly Pro Ile Thr Pro Ala Thr Thr Ser Ser Ile Thr Ala Ala Val Thr
                805                 810                 815

Ala Ser Ser Thr Thr Ser Ala Val Pro Met Gly Asn Gly Val Gly Val
            820                 825                 830

Gly Val Gly Val Gly Asn Val Ser Met Thr Tyr Ala Asn Ala Gln Thr
        835                 840                 845

Ala Met Ala Leu Met Gly Val Ala Leu His Ser His Gln Gln Gln Leu
    850                 855                 860

Ile Gly Gly Val Ala Val Lys Ser Glu His Ser Thr Thr Ala
865                 870                 875

<210> SEQ ID NO 16
<211> LENGTH: 314
<212> TYPE: PRT
<213> ORGANISM: Spodoptera exigua

<400> SEQUENCE: 16

Arg Pro Glu Cys Val Val Pro Glu Asn Gln Cys Ala Met Lys Arg Lys
1               5                   10                  15

Glu Lys Lys Ala Gln Arg Glu Lys Asp Lys Leu Pro Val Ser Thr Thr
            20                  25                  30

Thr Val Asp Asp His Met Pro Pro Ile Met Gln Cys Asp Pro Pro Pro
```

```
                35                  40                  45
Pro Glu Ala Ala Arg Ile His Glu Val Val Pro Arg Phe Leu Asn Glu
    50                  55                  60
Lys Leu Met Glu Arg Thr Arg Leu Arg Asn Val Pro Pro Leu Thr Ala
65                  70                  75                  80
Asn Gln Lys Ser Leu Ile Ala Arg Leu Val Trp Tyr Gln Glu Gly Tyr
                85                  90                  95
Glu Gln Pro Ser Glu Asp Leu Lys Arg Val Thr Gln Ser Asp Glu
                100                 105                 110
Asp Glu Glu Ser Asp Met Pro Phe Arg Gln Ile Thr Glu Met Thr
                115                 120                 125
Ile Leu Thr Val Gln Leu Ile Val Glu Phe Ala Lys Gly Leu Pro Ala
    130                 135                 140
Phe Ala Lys Ile Ser Gln Ser Asp Gln Ile Thr Leu Leu Lys Ala Cys
145                 150                 155                 160
Ser Ser Glu Val Met Met Leu Arg Val Ala Arg Arg Tyr Asp Ala Ala
                165                 170                 175
Thr Asp Ser Val Leu Phe Ala Asn Asn Gln Ala Tyr Thr Arg Asp Asn
                180                 185                 190
Tyr Arg Lys Ala Gly Met Ala Tyr Val Ile Glu Asp Leu Leu His Phe
                195                 200                 205
Cys Arg Cys Met Tyr Ser Met Met Met Asp Asn Val His Tyr Ala Leu
                210                 215                 220
Leu Thr Ala Ile Val Ile Phe Ser Asp Arg Pro Gly Leu Glu Leu Thr
225                 230                 235                 240
Leu Leu Val Glu Glu Ile Gln Arg Tyr Tyr Leu Asn Thr Leu Arg Val
                245                 250                 255
Tyr Ile Leu Asn Gln Asn Ser Arg Ser Pro Cys Cys Pro Val Ile Tyr
                260                 265                 270
Ala Lys Ile Leu Gly Ile Leu Thr Glu Leu Arg Thr Leu Gly Met Gln
                275                 280                 285
Asn Ser Asn Met Cys Ile Ser Leu Lys Leu Lys Asn Arg Asn Val Pro
    290                 295                 300
Pro Phe Phe Glu Asp Ile Asp Trp Asp Val
305                 310

<210> SEQ ID NO 17
<211> LENGTH: 8
<212> TYPE: PRT
<213> ORGANISM: Artificial
<220> FEATURE:
<223> OTHER INFORMATION: Synthetic peptide

<400> SEQUENCE: 17

Cys Glu Gly Cys Lys Gly Phe Phe
1               5

<210> SEQ ID NO 18
<211> LENGTH: 23
<212> TYPE: DNA
<213> ORGANISM: Artificial
<220> FEATURE:
<223> OTHER INFORMATION: Primer
<221> NAME/KEY: modified_base
<222> LOCATION: (9)..(9)
<223> OTHER INFORMATION: i
<221> NAME/KEY: modified_base
<222> LOCATION: (18)..(18)
<223> OTHER INFORMATION: i
```

```
<400> SEQUENCE: 18
tgygarggnt gyaargantt ytt                                           23

<210> SEQ ID NO 19
<211> LENGTH: 8
<212> TYPE: PRT
<213> ORGANISM: Artificial
<220> FEATURE:
<223> OTHER INFORMATION: Synthetic peptide
<221> NAME/KEY: SITE
<222> LOCATION: (3)..(3)
<223> OTHER INFORMATION: Xaa is Glu or Ser
<221> NAME/KEY: SITE
<222> LOCATION: (6)..(6)
<223> OTHER INFORMATION: Xaa is Leu or Arg

<400> SEQUENCE: 19

Cys Gln Xaa Cys Arg Xaa Lys Lys
1               5

<210> SEQ ID NO 20
<211> LENGTH: 23
<212> TYPE: DNA
<213> ORGANISM: Artificial
<220> FEATURE:
<223> OTHER INFORMATION: Primer
<221> NAME/KEY: modified_base
<222> LOCATION: (6)..(6)
<223> OTHER INFORMATION: i
<221> NAME/KEY: modified_base
<222> LOCATION: (9)..(9)
<223> OTHER INFORMATION: i

<400> SEQUENCE: 20
ttyttnagnc grcaytcytg rca                                           23

<210> SEQ ID NO 21
<211> LENGTH: 23
<212> TYPE: DNA
<213> ORGANISM: Artificial
<220> FEATURE:
<223> OTHER INFORMATION: Primer
<221> NAME/KEY: modified_base
<222> LOCATION: (6)..(6)
<223> OTHER INFORMATION: i
<221> NAME/KEY: modified_base
<222> LOCATION: (9)..(9)
<223> OTHER INFORMATION: i

<400> SEQUENCE: 21
ttyttnaanc grcaytcytg rca                                           23

<210> SEQ ID NO 22
<211> LENGTH: 23
<212> TYPE: DNA
<213> ORGANISM: Artificial
<220> FEATURE:
<223> OTHER INFORMATION: Primer
<221> NAME/KEY: modified_base
<222> LOCATION: (6)..(6)
<223> OTHER INFORMATION: i
<221> NAME/KEY: modified_base
<222> LOCATION: (9)..(9)
<223> OTHER INFORMATION: i

<400> SEQUENCE: 22
ttyttnagnc trcaytcytg rca                                           23
```

```
<210> SEQ ID NO 23
<211> LENGTH: 23
<212> TYPE: DNA
<213> ORGANISM: Artificial
<220> FEATURE:
<223> OTHER INFORMATION: Primer
<221> NAME/KEY: modified_base
<222> LOCATION: (6)..(6)
<223> OTHER INFORMATION: i
<221> NAME/KEY: modified_base
<222> LOCATION: (9)..(9)
<223> OTHER INFORMATION: i

<400> SEQUENCE: 23
ttyttnaanc trcaytcytg rca                                              23

<210> SEQ ID NO 24
<211> LENGTH: 39
<212> TYPE: DNA
<213> ORGANISM: Artificial
<220> FEATURE:
<223> OTHER INFORMATION: Primer

<400> SEQUENCE: 24
aattaagctt ccaccatgcc gttaccaatg ccaccgaca                             39

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
cttcaaccga cactcctgac                                                  20

<210> SEQ ID NO 26
<211> LENGTH: 22
<212> TYPE: DNA
<213> ORGANISM: Artificial
<220> FEATURE:
<223> OTHER INFORMATION: Primer

<400> SEQUENCE: 26
cagctccagg ccgccgatct cg                                               22

<210> SEQ ID NO 27
<211> LENGTH: 48
<212> TYPE: DNA
<213> ORGANISM: Artificial
<220> FEATURE:
<223> OTHER INFORMATION: Primer
<221> NAME/KEY: modified_base
<222> LOCATION: (36)..(36)
<223> OTHER INFORMATION: i
<221> NAME/KEY: modified_base
<222> LOCATION: (37)..(37)
<223> OTHER INFORMATION: i
<221> NAME/KEY: modified_base
<222> LOCATION: (41)..(41)
<223> OTHER INFORMATION: i
<221> NAME/KEY: modified_base
<222> LOCATION: (42)..(42)
<223> OTHER INFORMATION: i
<221> NAME/KEY: modified_base
<222> LOCATION: (46)..(46)
<223> OTHER INFORMATION: i
<221> NAME/KEY: modified_base
<222> LOCATION: (47)..(47)
<223> OTHER INFORMATION: i
```

-continued

```
<400> SEQUENCE: 27
cuacuacuac uaggccacgc gtcgactagt acgggnnggg nngggnng          48

<210> SEQ ID NO 28
<211> LENGTH: 32
<212> TYPE: DNA
<213> ORGANISM: Artificial
<220> FEATURE:
<223> OTHER INFORMATION: Primer

<400> SEQUENCE: 28
caucaucauc auggccacgc gtcgactagt ac                          32

<210> SEQ ID NO 29
<211> LENGTH: 27
<212> TYPE: DNA
<213> ORGANISM: Artificial
<220> FEATURE:
<223> OTHER INFORMATION: Primer

<400> SEQUENCE: 29
acgtcacctc agacgagctc tccattc                                27

<210> SEQ ID NO 30
<211> LENGTH: 24
<212> TYPE: DNA
<213> ORGANISM: Artificial
<220> FEATURE:
<223> OTHER INFORMATION: Primer

<400> SEQUENCE: 30
cgctggtata acaacggacc attc                                   24

<210> SEQ ID NO 31
<211> LENGTH: 39
<212> TYPE: DNA
<213> ORGANISM: Artificial
<220> FEATURE:
<223> OTHER INFORMATION: Primer

<400> SEQUENCE: 31
aattaagctt ccaccatgcc gttaccaatg ccaccgaca                   39

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
cttcaaccga cactcctgac                                        20

<210> SEQ ID NO 33
<211> LENGTH: 48
<212> TYPE: DNA
<213> ORGANISM: Artificial
<220> FEATURE:
<223> OTHER INFORMATION: Primer

<400> SEQUENCE: 33
attaagcttg ccgccatgcg ccgacgctgg tataacaacg gaccattc         48

<210> SEQ ID NO 34
<211> LENGTH: 39
```

```
<212> TYPE: DNA
<213> ORGANISM: Artificial
<220> FEATURE:
<223> OTHER INFORMATION: Primer

<400> SEQUENCE: 34
attaagcttg ccgccatgtc cctcggcgct cgtggatac                     39

<210> SEQ ID NO 35
<211> LENGTH: 137
<212> TYPE: DNA
<213> ORGANISM: Artificial
<220> FEATURE:
<223> OTHER INFORMATION: HSP27 ecdysone response element construct

<400> SEQUENCE: 35
ctagtagaca agggttcaat gcacttgtcc aataagctta gacaagggtt c aatgcactt     60 gtccaatgaa ttcagacaag ggttcaatgc acttgtccaa tctgcagaga c aagggttca   120 atgcacttgt ccaatat                                                   137

<210> SEQ ID NO 36
<211> LENGTH: 135
<212> TYPE: DNA
<213> ORGANISM: Artificial
<220> FEATURE:
<223> OTHER INFORMATION: Hsp27 ecdysone response element construct

<400> SEQUENCE: 36
cgatattgga caagtgcatt gaacccttgt ctctgcagat ggacaagtg c attgaaccc     60 ttgtctgaat tcattggaca agtgcattga acccttgtct aagcttattg g acaagtgca   120 ttgaacccct gtcta                                                     135

<210> SEQ ID NO 37
<211> LENGTH: 38
<212> TYPE: DNA
<213> ORGANISM: Artificial
<220> FEATURE:
<223> OTHER INFORMATION: Primer

<400> SEQUENCE: 37
attgaattcc accatggact ccaaagaatc attaactc                     38

<210> SEQ ID NO 38
<211> LENGTH: 42
<212> TYPE: DNA
<213> ORGANISM: Artificial
<220> FEATURE:
<223> OTHER INFORMATION: Primer

<400> SEQUENCE: 38
gagactcctg tagtggcctc gagcattcct tttattttttt tc                 42

<210> SEQ ID NO 39
<211> LENGTH: 31
<212> TYPE: DNA
<213> ORGANISM: Artificial
<220> FEATURE:
<223> OTHER INFORMATION: Primer

<400> SEQUENCE: 39
attctcgaga ttcagcaggc cactacagga g                            31

<210> SEQ ID NO 40
```

```
<211> LENGTH: 32
<212> TYPE: DNA
<213> ORGANISM: Artificial
<220> FEATURE:
<223> OTHER INFORMATION: Primer

<400> SEQUENCE: 40
attgaattca atgctatcgt aactatacag gg                           32

<210> SEQ ID NO 41
<211> LENGTH: 35
<212> TYPE: DNA
<213> ORGANISM: Artificial
<220> FEATURE:
<223> OTHER INFORMATION: Primer

<400> SEQUENCE: 41
attgtcgaca acggccggaa tggctcgtcc cggag                        35

<210> SEQ ID NO 42
<211> LENGTH: 48
<212> TYPE: DNA
<213> ORGANISM: Artificial
<220> FEATURE:
<223> OTHER INFORMATION: Primer

<400> SEQUENCE: 42
tcgggctttg ttaggatcct aagccgtggt cgaatgctcc gacttaac          48

<210> SEQ ID NO 43
<211> LENGTH: 35
<212> TYPE: DNA
<213> ORGANISM: Artificial
<220> FEATURE:
<223> OTHER INFORMATION: Primer

<400> SEQUENCE: 43
attgtcgaca aaggcccgag tgcgtggtgc cggag                        35

<210> SEQ ID NO 44
<211> LENGTH: 24
<212> TYPE: DNA
<213> ORGANISM: Artificial
<220> FEATURE:
<223> OTHER INFORMATION: Primer

<400> SEQUENCE: 44
tcacattgca tgatgggagg catg                                    24

<210> SEQ ID NO 45
<211> LENGTH: 82
<212> TYPE: DNA
<213> ORGANISM: Artificial
<220> FEATURE:
<223> OTHER INFORMATION: Glucocorticoid response e lement construct

<400> SEQUENCE: 45
agcttcgact gtacaggatg ttctagctac tcgagtagct agaacatcct g tacagtcga    60 gtagctagaa catcctgtac ag                                             82

<210> SEQ ID NO 46
<211> LENGTH: 82
<212> TYPE: DNA
<213> ORGANISM: Artificial
<220> FEATURE:
<223> OTHER INFORMATION: Glucocortocoid response e lement construct
```

<400> SEQUENCE: 46
tcgactgtac aggatgttct agctactcga ctgtacagga tgttctagct a ctcgagtcg    60 ctagaacatc ctgtacagtc ga    82

<210> SEQ ID NO 47
<211> LENGTH: 78
<212> TYPE: DNA
<213> ORGANISM: Artificial
<220> FEATURE:
<223> OTHER INFORMATION: Glucocorticoid response e lement construct

<400> SEQUENCE: 47
tcgactagct agaacatcct gtacagtcga gtagctagaa catcctgtac a gtcgagtag    60 ctagaacatc ctgtacag    78

<210> SEQ ID NO 48
<211> LENGTH: 78
<212> TYPE: DNA
<213> ORGANISM: Artificial
<220> FEATURE:
<223> OTHER INFORMATION: Glucocorticoid response e lement construct

<400> SEQUENCE: 48
gatcctgtac aggatgttct agctactcga ctgtacagga tgttctagct a ctcgactgt    60 acaggatgtt ctagctag    78

<210> SEQ ID NO 49
<211> LENGTH: 104
<212> TYPE: DNA
<213> ORGANISM: Artificial
<220> FEATURE:
<223> OTHER INFORMATION: Glucocorticoid response e lement construct

<400> SEQUENCE: 49
ctagttgtac aggatgttct agctactcga gtagctagaa catcctgtac a gtcgagtag    60 ctagaacatc ctgtacagtc gagtagctag aacatcctgt acac    104

<210> SEQ ID NO 50
<211> LENGTH: 104
<212> TYPE: DNA
<213> ORGANISM: Artificial
<220> FEATURE:
<223> OTHER INFORMATION: Glucocorticoid response e lement construct

<400> SEQUENCE: 50
ttaagtgtac aggatgttct agctactcga ctgtacagga tgttctagct a ctcgactgt    60 acaggatgtt ctagctactc gagtagctag aacatcctgt acaa    104

<210> SEQ ID NO 51
<211> LENGTH: 15
<212> TYPE: DNA
<213> ORGANISM: Artificial
<220> FEATURE:
<223> OTHER INFORMATION: Linker

<400> SEQUENCE: 51
cattggatcc ttagc    15

<210> SEQ ID NO 52
<211> LENGTH: 23
<212> TYPE: DNA

<213> ORGANISM: Artificial
<220> FEATURE:
<223> OTHER INFORMATION: Linker

<400> SEQUENCE: 52
ggccgctaag gatccaatgg gcc                                       23

<210> SEQ ID NO 53
<211> LENGTH: 29
<212> TYPE: DNA
<213> ORGANISM: Artificial
<220> FEATURE:
<223> OTHER INFORMATION: Primer

<400> SEQUENCE: 53
ctgaggtcta gagacggtgg cgggcggcc                                 29

<210> SEQ ID NO 54
<211> LENGTH: 31
<212> TYPE: DNA
<213> ORGANISM: Artificial
<220> FEATURE:
<223> OTHER INFORMATION: Primer

<400> SEQUENCE: 54
atatgaattc caccatggac tccaaagaat c                              31

<210> SEQ ID NO 55
<211> LENGTH: 36
<212> TYPE: DNA
<213> ORGANISM: Artificial
<220> FEATURE:
<223> OTHER INFORMATION: Primer

<400> SEQUENCE: 55
atatgctagc tgtgggggca gcagacacag cagtgg                         36

<210> SEQ ID NO 56
<211> LENGTH: 33
<212> TYPE: DNA
<213> ORGANISM: Artificial
<220> FEATURE:
<223> OTHER INFORMATION: Primer

<400> SEQUENCE: 56
atatgctagc tccagctcct caacagcaac aac                            33

<210> SEQ ID NO 57
<211> LENGTH: 30
<212> TYPE: DNA
<213> ORGANISM: Artificial
<220> FEATURE:
<223> OTHER INFORMATION: Primer

<400> SEQUENCE: 57
atatctcgag caattccttt tattttttc                                 30

<210> SEQ ID NO 58
<211> LENGTH: 30
<212> TYPE: DNA
<213> ORGANISM: Artificial
<220> FEATURE:
<223> OTHER INFORMATION: Primer

<400> SEQUENCE: 58
attactagtt ctgcggcccc cccgaccgat                                30

<210> SEQ ID NO 59
<211> LENGTH: 31
<212> TYPE: DNA
<213> ORGANISM: Artificial
<220> FEATURE:
<223> OTHER INFORMATION: Primer

<400> SEQUENCE: 59
aattactagt cccaccgtac tcgtcaattc c                           31

<210> SEQ ID NO 60
<211> LENGTH: 32
<212> TYPE: DNA
<213> ORGANISM: Artificial
<220> FEATURE:
<223> OTHER INFORMATION: Primer
<221> NAME/KEY: modified_base
<222> LOCATION: (15)..(15)
<223> OTHER INFORMATION: i
<221> NAME/KEY: modified_base
<222> LOCATION: (18)..(18)
<223> OTHER INFORMATION: i
<221> NAME/KEY: modified_base
<222> LOCATION: (27)..(27)
<223> OTHER INFORMATION: i
<221> NAME/KEY: modified_base
<222> LOCATION: (30)..(30)
<223> OTHER INFORMATION: i

<400> SEQUENCE: 60
attgctcgag aaagnccnga gwgcktngtn cc                          32

<210> SEQ ID NO 61
<211> LENGTH: 32
<212> TYPE: DNA
<213> ORGANISM: Artificial
<220> FEATURE:
<223> OTHER INFORMATION: Primer
<221> NAME/KEY: modified_base
<222> LOCATION: (15)..(15)
<223> OTHER INFORMATION: i
<221> NAME/KEY: modified_base
<222> LOCATION: (18)..(18)
<223> OTHER INFORMATION: i
<221> NAME/KEY: modified_base
<222> LOCATION: (27)..(27)
<223> OTHER INFORMATION: i
<221> NAME/KEY: modified_base
<222> LOCATION: (30)..(30)
<223> OTHER INFORMATION: i

<400> SEQUENCE: 61
attgctcgag aacgnccnga gwgtstngtn cc                          32

<210> SEQ ID NO 62
<211> LENGTH: 33
<212> TYPE: DNA
<213> ORGANISM: Artificial
<220> FEATURE:
<223> OTHER INFORMATION: Primer
<221> NAME/KEY: modified_base
<222> LOCATION: (10)..(10)
<223> OTHER INFORMATION: i
<221> NAME/KEY: modified_base
<222> LOCATION: (19)..(19)
<223> OTHER INFORMATION: i
<221> NAME/KEY: modified_base
<222> LOCATION: (28)..(28)
<223> OTHER INFORMATION: i

<400> SEQUENCE: 62

```
ttactcgagn acgwcccana tctctycnag gaa                    33
```

<210> SEQ ID NO 63
<211> LENGTH: 33
<212> TYPE: DNA
<213> ORGANISM: Artificial
<220> FEATURE:
<223> OTHER INFORMATION: Primer
<221> NAME/KEY: modified_base
<222> LOCATION: (10)..(10)
<223> OTHER INFORMATION: i
<221> NAME/KEY: modified_base
<222> LOCATION: (19)..(19)
<223> OTHER INFORMATION: i
<221> NAME/KEY: modified_base
<222> LOCATION: (28)..(28)
<223> OTHER INFORMATION: i

<400> SEQUENCE: 63

```
ttactcgagn acgwcccana tctcctynaa gaa                    33
```

<210> SEQ ID NO 64
<211> LENGTH: 948
<212> TYPE: DNA
<213> ORGANISM: Spodoptera exigua

<400> SEQUENCE: 64

```
ttttactcga ggacgtccca gatatcctcg aagaacggcg gcacgttcct g ttcttcagc    60
gttagtgaga tgcacatgtt ggagttctgc atgcccaggt tccgcagctc c gtcaggatg   120
ccgaggatct tagcgtagat gacagggcag cacggcgacc gactgttctg g ttcaggatg   180
tacacccgca gcgtgttcag gtaatatctc tggatctcct ccaccaacag g gttagctca   240
agcccgggtc ggtctgagaa aatgacgatg gcagtgagca gtgcatagtg g acgttatcc   300
atcatcatgg agtacatgca ccggcagaag tgcagcaggt cctcgatgac g taggccatg   360
cctgccttgc ggtagttgtc gcgggtgtac gcctggttgt tggcgaacaa c acgctgtct   420
gtcgccgcgt cgtaccgccg agctactcgc aacatcatca cctcactcga a caggccttt   480
aataatgtga tctgatccga ctgtgagatc tttgcgaacg ctggtaggcc c ttagcgaat   540
tcaacaatga gctgcactgt gaggatcgtc atctcggtga tctgacggaa c ggcatgtcc   600
gactcttctt cgtcttcatc cgactgtgtg actcttttta gatcctcttc t gatggctgt   660
tcatagcctt cttggtacca gaccagcctc gctattaagg acttctggtt g gcagtgagg   720
gggcacattc ttgagccttg tcctgtccat tagcttttca ttcaggaatc g tggcaccac   780
ctcgtgaatt cttgcggcct ctggaggcgg tggatcacag tccataatgg g aggcatgtg   840
atcatccact gtcgttgtac tgactggcaa cttgtctttt tcccttgtgtg c cttttctc   900
tttccttttc attgcacact ggttttctgg caccacgcac tccggcct          948
```

<210> SEQ ID NO 65
<211> LENGTH: 32
<212> TYPE: DNA
<213> ORGANISM: Artificial
<220> FEATURE:
<223> OTHER INFORMATION: Primer

<400> SEQUENCE: 65

```
aattccatgg tacgacgaca gtagacgatc ac                     32
```

What is claimed is:

1. An isolated or synthetic DNA sequence encoding a polypeptide selected from the group consisting of
   (a) the *Heliothis virescens* ecdysone steroid receptor shown in SEQ ID NO: 5;
   (b) the transactivation domain of the *Heliothis virescens* ecdysone steroid receptor shown in amino acids 1–162 of SEQ ID NO: 5;
   (c) the DNA binding domain of the *Heliothis virescens* ecdysone steroid receptor shown in amino acids 163–228 of SEQ ID NO: 5;
   (d) the hinge domain of the *Heliothis virescens* ecdysone steroid receptor shown in amino acids 229–326 of SEQ ID NO: 5;
   e) the ligand binding domain of the *Heliothis virescens* ecdysone steroid receptor shown in amino acids 327–545 of SEQ ID NO: 5;
   (f) the carboxy terminus of the *Heliothis virescens* ecdysone steroid receptor shown in amino acids 546–577 of SEQ ID NO: 5; and
   (g) the hinge and ligand binding domains of the *Spodoptera exigua* ecdysone steroid receptor shown in SEQ ID NO: 7.

2. The DNA sequence of claim 1 wherein said sequence encodes the *Heliothis virescens* ecdysone steroid receptor shown in SEQ ID NO: 5.

3. The DNA sequence of claim 2 wherein said sequence is SEQ ID NO: 2.

4. The DNA sequence of claim 2 wherein said sequence comprises the sequence depicted in SEQ ID NO: 3.

5. The DNA sequence of claim 2 wherein said sequence comprises the sequence depicted in SEQ ID NO: 4.

6. The DNA sequence of claim 1 wherein said sequence encodes the transactivation domain of the *Heliothis virescens* ecdysone steroid receptor shown in amino acids 1–162 of SEQ ID NO: 5.

7. The DNA sequence of claim 1 wherein said sequence encodes the DNA binding domain of the *Heliothis virescens* ecdysone steroid receptor shown in amino acids 163–228 of SEQ ID NO: 5.

8. The DNA sequence of claim 1 wherein said sequence encodes the hinge domain of the *Heliothis virescens* ecdysone steroid receptor shown in amino acids 229–326 of SEQ ID NO: 5.

9. The DNA sequence of claim 1 wherein said sequence encodes the ligand binding domain of the *Heliothis virescens* steroid receptor shown in amino acids 327–545 of SEQ ID NO:5.

10. The DNA sequence of claim 1 wherein said sequence encodes the carboxy terminus of the *Heliothis virescens* steroid receptor shown in amino acids 546–577 of SEQ ID NO: 5.

11. The DNA sequence of claim 1 wherein said sequence encodes the hinge and ligand binding domains of the *Spodoptera exigua* shown in SEQ ID NO: 7.

12. The DNA sequence of claim 11 wherein said sequence comprises SEQ ID NO: 6.

13. An isolated cell transformed with the DNA of claim 1.

14. The isolated cell of claim 13 wherein said isolated cell is a plant, fungal or mammalian cell.

* * * * *